United States Patent
Csiky

(10) Patent No.: US 10,702,254 B2
(45) Date of Patent: Jul. 7, 2020

(54) SURGICAL DEVICE AND ACCESSORIES

(71) Applicant: Laszlo Csiky, Urom (HU)

(72) Inventor: Laszlo Csiky, Urom (HU)

(*) Notice: Subject to any disclaimer, the term of this patent is extended or adjusted under 35 U.S.C. 154(b) by 241 days.

(21) Appl. No.: 15/833,250

(22) Filed: Dec. 6, 2017

(65) Prior Publication Data

US 2018/0092635 A1 Apr. 5, 2018

Related U.S. Application Data

(63) Continuation-in-part of application No. 13/393,884, filed as application No. PCT/HU2010/000095 on Sep. 2, 2010, now Pat. No. 9,877,794.

(30) Foreign Application Priority Data

Sep. 2, 2009 (HU) .................................. 0900538

(51) Int. Cl.
 *A61B 17/00* (2006.01)
 *A61B 34/00* (2016.01)
 (Continued)

(52) U.S. Cl.
 CPC .... *A61B 17/00234* (2013.01); *A61B 1/00128* (2013.01); *A61B 1/00135* (2013.01); *A61B 1/015* (2013.01); *A61B 1/018* (2013.01); *A61B 17/072* (2013.01); *A61B 17/29* (2013.01); *A61B 17/3421* (2013.01); *A61B 17/3423* (2013.01); *A61B 17/4241* (2013.01); *A61B 90/50* (2016.02); *A61B 17/0281* (2013.01); *A61B 17/12013* (2013.01); *A61B 18/1492* (2013.01); *A61B 90/361* (2016.02); *A61B 2017/003* (2013.01); *A61B 2017/00269* (2013.01); *A61B 2017/00278* (2013.01); *A61B 2017/00283* (2013.01); *A61B 2017/00314* (2013.01); *A61B 2017/00327* (2013.01); *A61B 2017/00336* (2013.01); *A61B 2017/00575* (2013.01); *A61B 2017/00637* (2013.01);
(Continued)

(58) Field of Classification Search
 CPC .............. A61B 17/00234; A61B 90/50; A61B 1/00128; A61B 2017/00336; A61B 2017/2908; A61B 2017/00991; A61B 2017/2937; A61B 2017/00327; A61B 2017/00314; A61B 2017/003; A61B 2034/302
See application file for complete search history.

(56) References Cited

U.S. PATENT DOCUMENTS

| 2003/0045900 | A1* | 3/2003 | Hahnen | ............. | A61B 17/07207 606/205 |
| 2004/0138525 | A1* | 7/2004 | Saadat | ................. | A61B 1/0055 600/104 |

(Continued)

*Primary Examiner* — Anh T Dang
(74) *Attorney, Agent, or Firm* — Olson & Cepuritis, Ltd.

(57) ABSTRACT

A device for surgical interventions comprises (i) an inner end (1) guidable/steerable to an operation field, (ii) an outer end (3) operated by user and (iii) a middle part (2) which connects both ends (1, 3) together. Force transmission units extend between the outer end (3) and the inner end (1). The force transmission units, the outer and the inner ends and the middle part (2) transfer movements of the outer end (3) to the inner end (1) in an identical measure, as if the inner end (1) was a straight continuation of the outer end (3).

8 Claims, 29 Drawing Sheets

(51) Int. Cl.
  *A61B 17/42* (2006.01)
  *A61B 1/018* (2006.01)
  *A61B 1/00* (2006.01)
  *A61B 17/34* (2006.01)
  *A61B 1/015* (2006.01)
  *A61B 17/29* (2006.01)
  *A61B 90/50* (2016.01)
  *A61B 17/072* (2006.01)
  *A61B 17/12* (2006.01)
  *A61B 34/30* (2016.01)
  *A61B 18/00* (2006.01)
  *A61B 18/14* (2006.01)
  *A61B 17/02* (2006.01)
  *A61B 17/04* (2006.01)
  *A61B 90/00* (2016.01)

(52) U.S. Cl.
  CPC ............ *A61B 2017/00663* (2013.01); *A61B 2017/00818* (2013.01); *A61B 2017/00823* (2013.01); *A61B 2017/00991* (2013.01); *A61B 2017/0409* (2013.01); *A61B 2017/0417* (2013.01); *A61B 2017/0464* (2013.01); *A61B 2017/07214* (2013.01); *A61B 2017/2906* (2013.01); *A61B 2017/2908* (2013.01); *A61B 2017/2925* (2013.01); *A61B 2017/2927* (2013.01); *A61B 2017/2937* (2013.01); *A61B 2017/2946* (2013.01); *A61B 2017/3425* (2013.01); *A61B 2017/3447* (2013.01); *A61B 2017/3452* (2013.01); *A61B 2018/00482* (2013.01); *A61B 2018/00589* (2013.01); *A61B 2018/00601* (2013.01); *A61B 2034/301* (2016.02); *A61B 2034/302* (2016.02); *A61B 2090/08021* (2016.02)

(56) References Cited

U.S. PATENT DOCUMENTS

| | | | |
|---|---|---|---|
| 2005/0085691 A1* | 4/2005 | Nakao | A61B 1/00071 600/128 |
| 2010/0106161 A1* | 4/2010 | Tabbara | A61M 39/0247 606/108 |

* cited by examiner

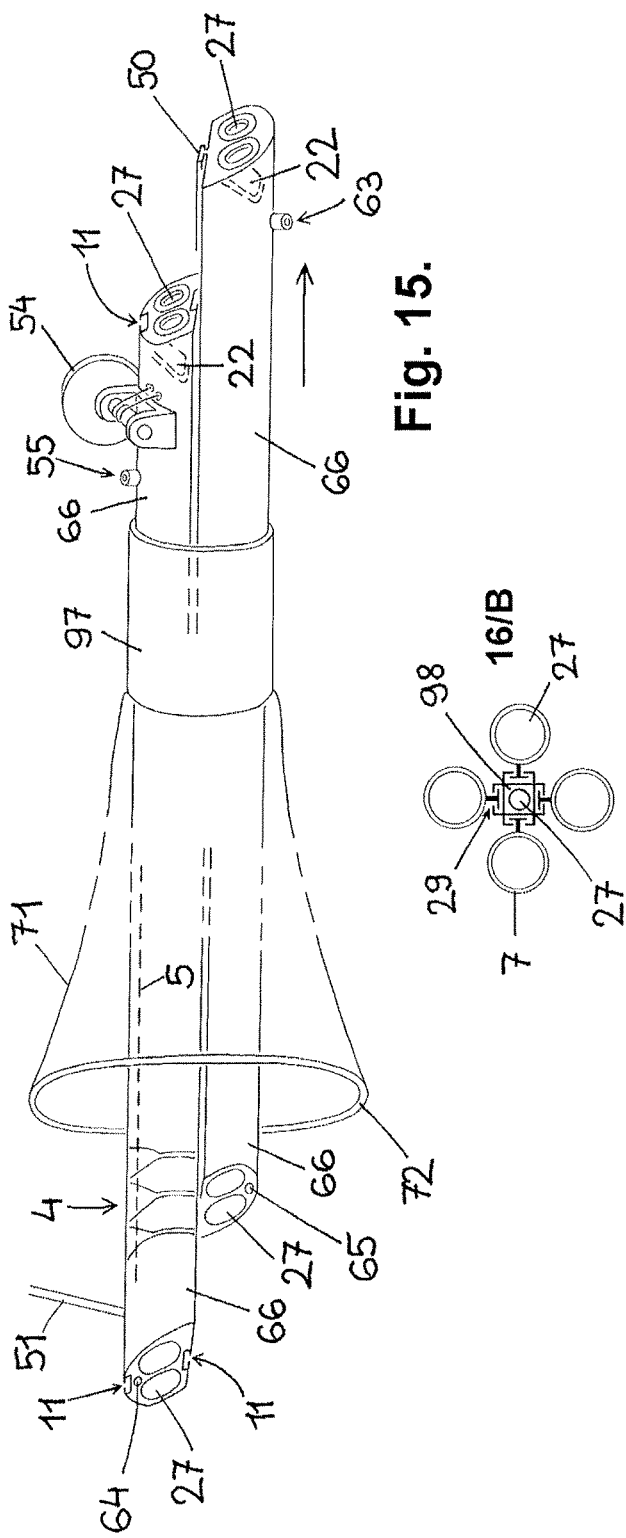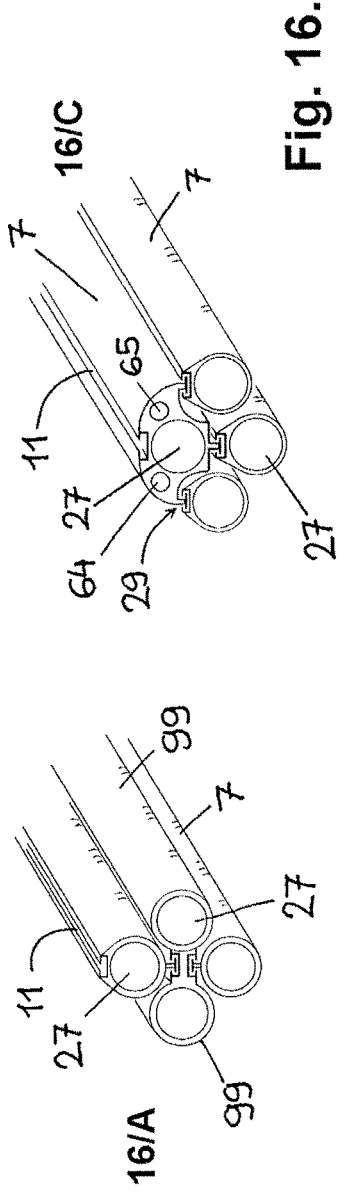

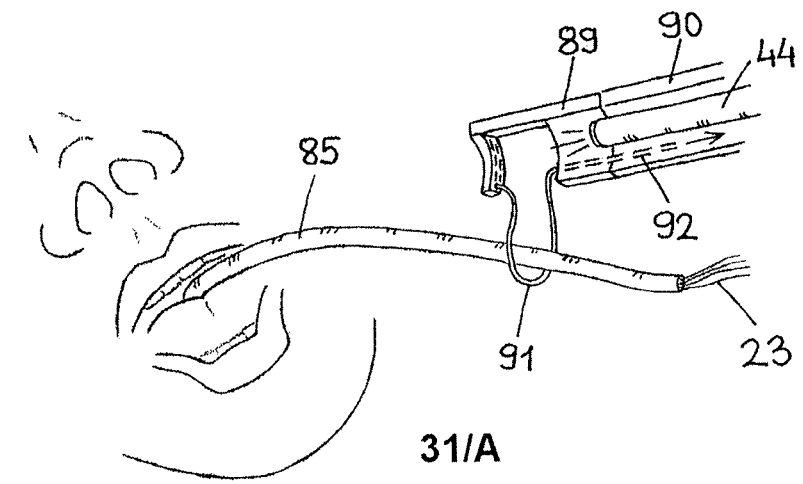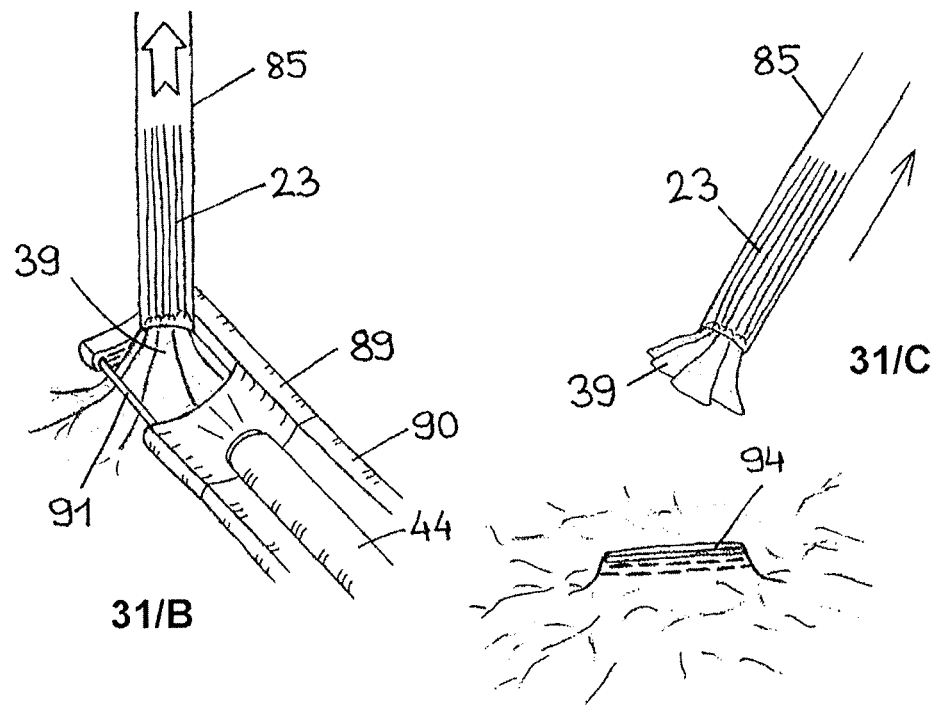
Fig. 31.

SURGICAL DEVICE AND ACCESSORIES

CROSS REFERENCE TO RELATED APPLICATIONS

This application is a continuation-in-part of U.S. Ser. No. 13/393,884 filed on May 17, 2012, which application is a 371 U.S. National Stage of PCT/HU2010/000095 filed on Sep. 2, 2010, which claims priority of Hungarian Patent Application No. P0900538 filed on Sep. 2, 2009, each of which is incorporated herein by reference.

FIELD OF INVENTION

This invention relates to surgical devices, more particularly to devices suitable for minimal invasive surgery.

BACKGROUND OF INVENTION

Within the last few years the marriage of the so-called minimal invasive surgery (i.e. laparoscopic surgery, characteristically using straight thin and rigid instruments) and endoscopy (i.e. interventions inside the hollow organs through the natural orifices characteristically with flexible instruments) has resulted in the birth of the NOTES (Natural Orifice Translumenal Endoscopic Surgery) technique, which has been recently applied mainly in experimental surgery. The desired advantage of the NOTES comparing to laparoscopic surgery (surgery through small abdominal incisions) includes the further minimization of surgical intervention and operative risk in the treatment of certain diseases. However, to perform NOTES intraabdominal interventions (e.g. removal of the gall bladder, appendix, ligation of the ovarian tubes, etc.) it is necessary (i) to insert a flexible endoscopic system e.g. through the mouth, vagina or the rectum into the abdominal cavity via the hollow organ's wall, (ii) to perform the surgical intervention with the device in the abdominal cavity, (iii) to remove the necessary tissues or organs out of the body, (iv) to safely close the artificially created opening on the hollow organ's wall at the end of the procedure, and (v) to remove the device-system through the natural orifice.

According to current research there is no device or device-system available, which would be able to perform alone all steps of the aforementioned interventions (i.e. the whole NOTES or SPLS). It must be noted that the currently available devices, which can perform only a single part of the whole procedure, are still not enough reliable, and in most of the cases their usages are difficult and awkward. It is still a challenging problem to have these instruments fixed inside the abdominal cavity, to have them arranged in a triangular pattern (the so-called triangulation) to achieve their better coordination and cooperation, and to safely close the artificially created opening on the hollow organ's wall, respectively. The above mentioned difficulties may lead to severe, occasionally to life threatening complications, e.g. injury of vital organs, bleeding or peritonitis.

There are plenty of various devices developed for the NOTES interventions. Their properties usually evolve as a result of the various combinations of laparoscopic and endoscopic features.

One of the most promising recent solutions is described in the US/2007/086079 patent application. According to this description, the flexible instruments are inserted into the abdominal cavity through the working channels of an endoscopic tube like device. The inner end of this endoscopic device is controlled by its outer end, utilizing traditional technical solutions. The inner ends of the instruments inserted into the endoscopic tube-like device are also controllable by a bulky device, which is attached to the outer end of the endoscopic tube-like device. However, the disadvantage of this solution is that the fixation of the inner ends of the instruments and the endoscopic tube-like device, and the proper triangulation of the instruments remain unsolved. Another drawback is that the device controlling the inner ends of the instruments is relatively bulky, and in case of a new instrument insertion it requires additional assembling, and furthermore because of its relatively large size it needs extended room when more than two instruments are inserted. Additionally, this solution does not follow the well prepared and reliable laparoscopic maneuvers but requires new kind of maneuvers. Its main problem is not concerned with the necessity to learn a new technique but with the fact that when any complication occurs during a procedure, it is advantageous to solve it with the laparoscopic technique. The two different techniques may disturb each other when they are used simultaneously.

Another innovative idea is described in the WO/2008/131046 patent application. This instrument is a simple modification of the traditional laparoscopic instruments: both the head and the handle of the instrument are bendable simultaneously toward each other. The bending of the handle controls the synchronous bending of the head by wires. In fact, this instrument was developed primarily for the SPLS (Single Port Laparoscopic Surgery), where usually the navel is used to enter the abdominal cavity. This new SPLS method is considered to be an alternative to the NOTES technique. Actually the SPLS is a variation of laparoscopy. A major drawback of this solution is that the movements of the inner and outer ends of the cited instrument are contrariwise as compared to the conventional laparoscopic instrument, and this is really difficult to learn. The relative congestion of the instruments in the above mentioned ideas is another disadvantage, which could jeopardize the effectiveness and safety of these procedures.

SUMMARY OF INVENTION

The present invention is a surgical device system developed for the new types of surgical procedures, which is—advantageously similarly to the laparoscopic technique—able to accomplish all steps (access, surgical intervention, closure) of NOTES (Natural Orifice Transluminal Endoscopic Surgery), SPLS (Single Port Laparoscopic Surgery) and IE (Interventional Endoscopy) procedures, and said device system—according to an advantageous embodiment—comprises laparo-endoscopic instruments, trocar sleeves, a tube or an endoscopic device, and further attachable accessories.

It is clear from the above that there is a need for the development of such a laparo-endoscopic system, with which all steps of the NOTES, SPLS or IE procedures can be reliably completed through the natural orifices, similarly to the well proved and developed laparoscopic technique.

The object of the present invention is to develop a device-system to reduce the possible complications due to the immature solutions or unsolved problems of NOTES, SPLS or IE, which allows easier, faster and safer completion of all steps of the NOTES, SPLS or IE procedures through the natural orifices similarly to the reliable and well developed laparoscopic technique.

The present invention is based on the recognition that (i) the complex inner and outer ends of the device-system—acting as the continuation of each other—are considered as a unit having laparoscopic features, while the middle part—connecting the inner and outer ends together—is rather regarded as a unit with flexible endoscopic features, and that (ii) the movements of the inner and outer ends of the device—introduced with the help of a flexible endoscope-like device through the natural orifices—are synchronized to move at the same time and degree as they both were the inner and outer parts of a traditional laparoscopic instrument, and that (iii) an appropriately modified endoscopic stapler is used with the help of accessory devices attached to the device-system, will make it possible to perform all steps of NOTES, SPLS or IE procedures easier, faster and safer.

Based upon the above recognition, the aforementioned problem will be solved by the application of devices designed for surgical interventions, which comprise inner ends guidable to the operation field, outer ends operated by the user and middle parts connecting the inner and the outer ends together. The main idea of the invention is that it contains force transmission units extended between the inner and outer ends, and the force transmission units, the inner and outer ends and the middle part are constructed in such a manner, that any movements of the actuated outer end are transferred in an equivalent degree to the inner end, as if the inner end were the straight continuation of the outer end.

Advantageously there is a channel inside the device, and the force transmission unit comprises a first force transmission unit that allows bending of the outer and the inner ends simultaneously in the same rotational angle and in the same rotational direction relative to the middle part, and a second transmission unit that transfers the longitudinal/axial movements of the outer and the inner ends to each other simultaneously with the same degree but in the opposite direction, respectively.

The outer and the inner ends and the middle part of the device are advantageously the components of an instrument or a trocar sleeve. Advantageously the outer and the inner ends are connected to the middle part by articulations. Advantageously both the outer and the inner ends are telescopic. The first and the second force transmission units could be integrated in one device, i.e. either in the surgical instrument or in the trocar sleeve, however according to another possible embodiment one of the two force transmission units is incorporated in the surgical instrument and the other force transmission unit in the trocar sleeve that contains the surgical instrument inside.

Furthermore the object of the present invention is a tube or an endoscopic device capable to receive one or more surgical instruments and/or trocar sleeves, and the tube or the endoscopic device is designed to be able to deliver the inner ends of the instruments and/or the trocar sleeves to the operation field, and also the inner end of the tube or the endoscopic device is shaped to enable the proper fixation and triangulation of the surgical instruments and/or trocar sleeves.

Furthermore the object of the present invention is a wound closure device-system, that according to its main concept contains an implanting tube attachable to other devices and an implanting sheath, there are locking elements and an implanting rod—that implanting rod is operable through its outer end and serves to release these locking elements out of the sheath—inside the implanting sheath, and there are threads connecting to each locking elements, and the threads are delivered through the longitudinal split of the sheath and the outer end of the tube, and advantageously the implanting tube, the sheath and the implanting rod are flexible.

Furthermore another object of the present invention is an endoscopic stapler, which has a body portion and a head portion that are connected together advantageously with articulation, and also has opposed stapling surfaces on the head portion with a control thread—that allows tension or relaxation—extending between their free ends, and said thread is advantageously placed within a longitudinal channel formed inside the head and the body portions of the stapler.

Furthermore another object of the present invention is a protective sheath attachable to the outer surface of one or more surgical instruments or one or more trocar sleeves or to the outer surface of a tube or an endoscopic device that contains one or more surgical instruments or trocar sleeves.

Furthermore another object of the present invention is an endoscopic balloon tube, which has two inflatable balloon rings located in an appropriate distance from each other, and has also at least one gas tube that allows to inflate the balloons, and said endoscopic balloon tube could be arranged on the inner region of one or more surgical instruments or one or more trocar sleeves or on the inner region of a tube or an endoscopic device that contains one or more surgical instruments or trocar sleeves.

Furthermore another object of the present invention is a catheter that can be inserted into the working channel of a trocar sleeve, tube or endoscopic device, and said catheter has an electric unit—which is able to cut or coagulate tissues—mounted on the inner end advantageously on the tip of the catheter, said electric unit has an electrical wiring extending along the catheter, and said electrical wiring is connectable to an electric power supply.

According to an advantageous embodiment hereof, the surgical instrument is inserted into the trocar sleeve, and the trocar sleeves are inserted into the partially or totally flexible tube or endoscopic device. Advantageously the connections between the tube or the endoscopic device and the trocar sleeves and the surgical instruments allow both axial and rotational movements to each other. If required, further accessory devices (e.g. protector sheath, wound closure device, endoscopic stapler, etc.) could be attached to their inner or outer surfaces. Advantageously all connections allow longitudinal movement or sliding along the longitudinal axis and rotation around the longitudinal axis, respectively.

According to an advantageous embodiment of the surgical instruments, the surgical instrument advantageously consists of three parts: the partially flexible middle part and the two telescopically extendable rigid inner and outer ends, and said inner and outer ends are connected to the middle part through joint-like articulations. Advantageously the segments of the middle part adjacent to the articulations are also rigid. The cross section of the instrument is advantageously circular.

Advantageously the outer and the inner ends of the instrument are simultaneously bendable at the articulations relative to the middle part in the same rotational angle and in the same rotational direction (when the middle part is in straight position, the rotational axes of the outer and inner ends at the articulations are parallel with each other), as if the outer and the inner ends were the components of one traditional laparoscopic instrument. The bending of the inner and the outer ends are executed advantageously only in one common plane (in case the middle part is in straight position) and advantageously through a pair of antagonistic wires, and said wires extend from the inner end throughout the articulations and the middle part to the outer end opposite to each other. Of course, other embodiments make it possible that the articulations are bendable in more than one common plane utilizing more than one pair of antagonistic wires. It is obvious that any recent technical solution is also acceptable to achieve the above described bending mechanism. Such possible solution could be a flexible or rigid pusher rod that is placed within the middle part and is connected to both the outer and the inner ends.

Of course any recent solutions concerning the construction of the articulations can offer the benefits referred above. The articulations that connect together the outer and the inner ends with the middle part may have more than one component.

There is a releasable ratchet locker located at the articulation that connects the middle part and the outer part together. The ratchet mechanism with the locker can fix the desired angle between the middle part and the outer and the inner ends transiently or permanently. The locker function is activated or deactivated upon request.

The telescopic ends consist of rigid straight tubes, which are insertable into one another. The head of the surgical instrument is located on the inner telescopic end, and advantageously is constructed similarly as the head of any recently used laparoscopic instruments, including the camera as well. The handle is situated on the outer telescopic end of the surgical instrument, and advantageously it is also constructed similarly as the handle of any recently used laparoscopic instruments, including the camera as well. The opening and the closing movements of the handle of the instrument control the function of the head with the help of a motive wire that extends from the outer end through the middle part to the inner end. The functions of the instrument, according to the present invention, also offer the same functions as any current instruments designed for any kind of energy transmission (e.g. electric, ultrasonic, etc.) on the field of surgery.

In spite of the fact that the outer and the inner telescopic ends are separated from each other by the middle part, they move together simultaneously, as if they were the straight continuation of each other, similarly to the movements of the inner and outer ends of a straight traditional laparoscopic instrument. When, for example, the outer telescopic end is pushed to some extent, that is, its length is reduced, the length of the inner telescopic end becomes simultaneously elongated with the same extent, and this works vice versa of course. This movement is directed by the force transmission unit situated inside the surgical instrument.

According to an advantageous embodiment this force transmission unit is located inside the channel of the instrument and advantageously consists of ball shaped force transmission particles. The channel extends from the inner telescopic end through the middle part to the outer telescopic end. The full length of the channel is filled up with balls. The diameter of the ball is somewhat smaller than the inner diameter of the channel. Advantageously there are holes in the middle of the balls, and the motive wire travels through these holes from the handle to the head. Advantageously the channel is provided with antifriction material. Advantageously the ball like force transmission particles are able to pass easily through the channels at the articulations. When the handle of the instrument is pushed forward, the handle push the last ball in the channel of the outer telescopic end. The adjacent balls transfer this pushing force to one another, and at last the first ball in the channel of the inner end pushes forward the head of the instrument, resulting in the elongation of the inner telescopic end. To execute the movement in the opposite direction that is to reduce the length of the inner telescopic end, it is advantageous to utilize a wire that connects the two telescopic ends together, and for this purpose the motive wire is also acceptable. When pulling the handle of the instrument, the outer telescopic end becomes elongated and the wire—fixed to the handle—simultaneously pull in the inner telescopic end. If the free transmission is guaranteed, any other form distinct from the ball shape is suitable. The bendable connections among the force transmission particles, which are threaded by the motive wire, are designed to resist their compression along the longitudinal axis and to resist their torsion to each other around the longitudinal axis.

According to another advantageous embodiment the force transmission unit is a hydraulic unit advantageously with elastic capsule, and said hydraulic unit is located inside the channel described above. According to an advantageous embodiment, the hydraulic unit has three parts: the inner and the outer ends and the middle part. The three parts of the hydraulic unit communicate with one another and they form together one common cavity. This hydraulic unit is a closed system and the hydraulic fluid does not communicate with the outer environment, it only flows through the three parts of the common cavity. The middle part of the hydraulic unit is located advantageously in the channel of the middle part of the instrument, and their lengths are equal, and said middle part of the hydraulic unit is fixed to the channel in order to avoid shifting. The inner and the outer ends of the hydraulic unit are located inside the channels of the inner and the outer telescopic ends of the instrument. The inner and the outer ends of the hydraulic unit are advantageously designed to allow only longitudinal expansion or reduction along their longitudinal axis without any change in their diameter. The capsules of the ends of the hydraulic unit are advantageously able to move within the channels of the ends of the instrument along its longitudinal axis. One possible advantageous solution regarding the ends of the hydraulic unit would be the accordion like folding of the walls of both ends. When the outer telescopic end is compressed longitudinally because the handle of the instrument is pushed, the accordion shaped outer end of the hydraulic unit becomes simultaneously compressed along its longitudinal axis. Thereby the elevated pressure within the outer end of the hydraulic unit is transferred through the fixed hydraulic middle part to the inner hydraulic end resulting in the longitudinal expansion of the accordion folded inner hydraulic end that leads to the elongation of the telescopic inner end as well. Advantageously the extent of the elongation and the extent of the shortening are equal. Along with the accordion folded design, a similar result can be achieved, if the wall of the hydraulic unit is made of appropriately elastic material. To execute the movement in the opposite direction in order to reduce the length of the inner telescopic end, it is advantageous to utilize a wire that connects the two telescopic ends together, and for this purpose the motive wire is also acceptable. When pulling the handle of the instrument, the outer telescopic end becomes elongated and the wire— fixed to the handle—simultaneously pulls in the inner telescopic end.

Yet another possible design of the force transmission unit is a flexible sheath placed within the channel of the instrument, which, according to an advantageous solution, is a coiled spring or a plastic tube. The motive wire is inside the flexible sheath. Advantageously the flexible sheath has insulating properties. Advantageously the flexible sheath resists compression along the longitudinal axis and also resists torsion around the longitudinal axis.

The head situated on the inner end of the instrument can be rotated around the longitudinal axis. The rotation of the head is controlled by the rotation of the outer end of the instrument, advantageously without the need to rotate the handle. The rotation of the handle advantageously is independent from the rotation of the head. Advantageously the head located on the inner end and the outer end rotates with the same degree. The rotation of the head and the inner end by the outer end is executed via the connected force transmission particles—said connections among the particles resist to the torsion effects around the longitudinal axis as described before, or is executed via the flexible sheath that also resists to the torsion effects around the longitudinal axis. Of course any other known solutions are acceptable with regard to the rotation of the head.

On the middle part of the instrument at least one connecting ring is placed advantageously to connect between the tube and the instrument. The instrument is easily rotatable within the ring. There is a connecting groove formed on the outer surface of the ring. According to another advantageous solution, a thread with needle is connected to the ring which helps to fix of the middle part of the instrument to any part of the abdominal wall.

According to another advantageous embodiment the instrument is attachable to the tube through a simple trocar sleeve. There is a sliding connection between the tube and the trocar sleeve, and the middle part of the instrument is located in the trocar sleeve. The middle part of the instrument is advantageously longer than the trocar sleeve. The instrument is rotatable and forth and back slidable within the trocar sleeve. Advantageously there is a valve and an airtight ring on the outer end of the trocar sleeve.

According to another advantageous embodiment the instrument has three main components: the partially flexible middle part and the rigid telescopically extendable outer and inner ends which are connected to the middle part through joint-like articulations. The force transmission system is the same as described above. The instrument has no wire to execute the bending of the telescopic ends. According to this solution the instrument is connected to the tube with such a trocar sleeve which has a partially or totally flexible middle part, and rigid outer and inner ends that are connected to the middle part through articulations. The bending of the outer and the inner ends are executed by the antagonistic wires located within the trocar sleeve. Advantageously the ratchet mechanism is mounted on the outer articulation. There is advantageously a valve and an airtight ring located on the outer end of the trocar sleeve.

The length of the middle part of the trocar sleeve is advantageously longer than the length of the tube. There is a sliding connection between the trocar sleeve and the tube. The length of the middle part of the instrument is advantageously longer than the length of the middle part of the trocar sleeve. The instrument within the trocar sleeve is easily moveable along the longitudinal axis and also rotateable around the longitudinal axis.

According to another advantageous embodiment the instrument consists of three main parts: the flexible middle part and the non-telescopic rigid outer and inner ends. The motive wire is situated inside the instrument. There is no additional force transmission unit within the instrument, as this transmission function is executed by the middle part and the two rigid ends.

An instrument constructed this way is connected to the tube advantageously through a trocar sleeve which has a partially or totally flexible middle part and with articulations connected rigid telescopic outer and inner ends. The simultaneous bendings of the articulations as described earlier are executed by the antagonistic wires situated within the wall of the trocar sleeve. Similarly, the ratchet mechanism could be formed on the outer articulation. The simultaneous elongation and shortening of the telescopic ends of the trocar sleeve are the results of the forward or backward movements of the instrument within the trocar sleeve. Advantageously there is a sliding connection between the trocar sleeve and the tube, which allows free movements along the longitudinal axis. Advantageously the sliding connection is accomplished by at least one connecting ring situated on the middle part of the trocar sleeve, and said ring is freely rotateable around the middle part. Advantageously the ring has a connecting groove that is connected with the rail mounted on the inner surface of the tube. There is an airtight valve and a ring on the outer end of the trocar sleeve.

According to an advantageous embodiment the trocar sleeves are connected to one another through sliding connections mounted longitudinally on their outer surfaces, and each trocar sleeve is connected with the two adjacent trocar sleeves to form a cylindrical arrangement. Advantageously four connected trocar sleeves are sufficient to perform most surgical interventions. In this case the cross section of each connected trocar sleeve is advantageously a quarter sector, and they together make a full circle, thereby the common outer cylindrical form makes a gentler intervention possible (e.g. when penetrating through the gastric wall). The sliding connections (a groove or a rail fitting to one another) are situated on the flat superficia of the trocar sleeves, and said sliding connections allow the longitudinal movements of the trocar sleeves relative to each other. This kind of trocar sleeve has two flat superficia, one of them has the groove and the other has the rail that fits to the groove. The cross sections of the working channels of the trocar sleeves are advantageously rounded. This kind of trocar sleeves could be partially or totally flexible or rigid. The inner end of the trocar sleeves may have an oblique plane allowing easier penetration through the stomach wall.

According to this possible solution, to the trocar sleeves with sector cross sections, rigid outer and inner telescopic ends are advantageously attached through articulations. Advantageously the cross sections of the telescopic ends are round, and said ends are rotatable relative to the middle part around the longitudinal axis. In this case there is no force transmission unit to actuate the telescopic ends. This telescopic function is executed by the surgical instrument located within the working channel of the telescopic trocar sleeve, and said instrument has a flexible middle part and rigid outer and inner ends, and is able to move longitudinally forth and back in the working channel. The simultaneous bending of the telescopic ends at their articulations are advantageously directed by a pair of antagonistic wires located within the trocar sleeve. At the outer end of the trocar sleeve there is an airtight valve and a sealing ring.

There are several other possible solutions to connect the trocar sleeves together. According to an advantageous embodiment, the additional trocar sleeves are connected to the outer surface of a double trocar sleeve through sliding connections. Advantageously the trocar sleeves are attached to the junction part of the double trocar sleeve. In addition further connecting grooves or rails could be formed on the outer surfaces of the double trocar sleeve or on the additionally attached trocar sleeves to connect them e.g. with a thread, stick or rod to ensure their fixation to the abdominal wall.

According to another advantageous embodiment, the trocar sleeves are connected to the outer surface of a trocar guide through sliding connections. The connecting grooves or rails are mounted on the outer surface of the trocar guide.

Inside the trocar guide a smaller diameter working channel could be situated, which could be used to insert e.g. a ballooned access catheter. The inner end of the trocar guide is advantageously sharp. According to a further advantageous embodiment the additional trocar sleeves are attached to a central trocar sleeve through sliding connections. Advantageously the outer cross section of the central trocar sleeve is optional, while the cross section of the working channel inside the central trocar sleeve is round. Advantageously there could be further channels located inside the central trocar sleeve, e.g. gas or suction-irrigation channels. The connecting grooves or the rails are mounted on the outer surface of the central trocar sleeve.

A tube is not necessary to introduce the trocar sleeves if they are connected together. The trocar sleeves could be fixed to the abdominal wall transiently or permanently with a ring located advantageously near to the inner end of the middle part. The fixation is possible with a thread with a needle, or with a rigid stick or with a control rod. The connected trocar sleeves within the ring are free to move along and to rotate around the longitudinal axis, respectively. In case no tube is used, advantageously there could be connecting grooves or rails formed on the outer surfaces of the trocar sleeves to allow the connection of other endoscopic devices.

The trocar sleeves connected together by sliding connections are also insertable into the abdominal cavity or fixable to the abdominal wall with the help of a partially or totally flexible simple tube. In this case there is no groove or rail formed inside the tube, they are formed only on the outer surface of the tube. The inner end of the tube may have a normal (i.e. flat), oblique or step-form shape. There may be a thread, stick or rod connected to the outer surface of the inner end of the tube, each of them allows fixing the tube to the abdominal wall. The stick may have a connecting foot that fits into the advantageously longitudinally situated connecting groove on the outer surface of the tube, and said connecting foot is slidable within the groove. In this case the inner end of the tube, which is fixed to the abdominal wall with the stick, is slidable back and forth by the help of the connecting foot, thereby allowing the proper adjustment of the inner end over the designated operating field. At the same time by the help of the rigid stick or rod the inner end of the tube is easily maneuverable to any desired part of the intraabdominal cavity, or is fixable in any desired location and position, respectively. Of course several other outer endoscopic devices (e.g. wound closure device, camera, forceps, etc.) could be connected to the groove located on the outer surface of the tube.

In the following part hereof, the tubes and the endoscopic devices containing surgical instruments and/or trocar sleeves will be discussed with their possible advantageous embodiments.

The tube refers to a solution, which has a long cylindrical body with one single lumen inside, and into this lumen surgical instruments, trocar sleeves or other accessory devices could be inserted. In the context of the present invention an endoscopic device is a tube having more than one lumen.

According to the simplest advantageous solution both ends of the tube are normal (i.e. straight). Advantageously the outer and the inner ends of the tube could be rigid and the middle part could be flexible. The inner diameter of the tube makes it possible to insert more than one—advantageously four—trocar sleeves. The inner surface of the tube could be completely smooth, or according to an advantageous embodiment, may have longitudinal connecting grooves or rails on the inner surface. Advantageously there could be longitudinal connecting grooves or rails also on the outer surface of the tube. A thread, a stick or a rod could be attached to the outer surface of the tube advantageously at the inner end region. There is advantageously a joint-like articulation between the inner end and the middle part of the tube. The inner end is bendable at the articulation relative to the middle part by the help of a pair of wires that extend longitudinally throughout the tube, and an articulating device mounted on the outer end of the tube.

The opening of the inner end of the tube could be normal (i.e. straight), oblique or step-form. The inner opening is straight if the plane of the inner opening is perpendicular to the longitudinal axis of the tube. The inner opening is oblique if the plane of the inner opening is not perpendicular to the longitudinal axis of the tube. The inner opening is step-form, if the straight or oblique opening is combined together with an opening located on the side of the inner end of the tube (the plane of the side opening is advantageously parallel with the longitudinal axis). The step-form opening has the advantage of significantly expanding the size of the interventional area and assuring easier maneuvers while the middle part of the instruments and/or trocar sleeves remain at least partly surrounded by the tube. The greater the size of the opening of the inner end facing toward the operation field, the greater is the freedom of movements of the instruments. This opening area could be readily enlarged to the desired size by additionally increasing the size of the side opening component.

The enlarged diameter of the inner opening makes it possible to arbitrary increase the distance between the inner articulations of the instruments and/or trocar sleeves without exiting the tube by pushing the instruments relative to one another along their longitudinal axis. The possible extent of the instruments dislocation is determined advantageously by the largest diameter of the inner opening. According to an advantageous solution, the direction of the largest diameter of the inner opening corresponds to the direction of the longitudinal axis of the device.

During laparoscopic surgery the intervention could be performed optimally only in case the operation field and the two operating instruments form a triangle with an appropriate wide base (this is the so called triangulation), and said base of the triangle is determined by the distance between the two instruments inserted into the abdominal cavity. In case of laparoscopic surgery the size of the triangle base—i.e. the distance between the two operating instruments—is alterable only if one of the instruments is removed and then reinserted through another location—i.e. new wound—into the abdominal cavity across the abdominal wall.

According to the present invention the size of the triangulation base can be altered (increased or decreased) without the need to create additional openings across the abdominal wall by displacing the instruments and/or trocar sleeves along each other so as to increase the distance between the inner articulations of the instruments and/or trocar sleeves. Such displacement is possible in the case of a straight tube inner end; however, it is more advantageous to use an oblique or step-form opening at the inner tube end, in order to maintain all the inner articulations of the instruments and/or trocar sleeves within the tube. In case of a tube or endoscopic device with a normal (straight) end at least one of the instruments' or trocar sleeves' inner articulation has to be moved out of the tube in order to ensure sufficiently large triangle base (see e.g. FIG. 22).

In case of oblique or step-form openings the size of the triangle base that can be ensured without any of the inner articulations exiting the tube is determined by the largest diameter of the inner opening (see FIG. 23). The distance between the inner articulations of the instruments (i.e. the size of the triangle base) is optionally alterable (can be enlarged or reduced) by the relative shifts of the instruments and/or trocar sleeves along their longitudinal axis, depending on the largest diameter of the inner opening. In addition the step-form opening is more advantageous than the oblique opening because it ensures the reliable connections—said connections allow movements along the longitudinal axis and rotation around the longitudinal axis—of at least two instruments or trocar sleeves to the tube or to the endoscopic device within the entire extent of the inner opening. The reliable connection between the instrument or the trocar sleeve and the inner end of the tube or the endoscopic device guarantees the appropriate stability to the inner end of the instrument or the trocar sleeve in order to perform the surgical intervention with safe maneuvers.

It is a remarkable advantage of the present invention that it allows the optional and stable alteration of the size of the triangle base without creating additional wounds, and furthermore allows the optional change in the position of the inner end of the tube or the endoscopic device (e.g. with a control rod) and the fixation of the inner end in the new position to ensure the optimal access to any operation field. For all these results the adjustable telescopic ends are also necessary, of course.

The ability to arbitrary change the size and/or the position of the triangulation base without the need to create additional wounds is considered to be a significant advantage over the recently used modern laparoscopic technique.

An independent opening could be situated also on the wall of the middle part of the tube. Advantageously there is an articulating device, a gas connection, and an arbitrary detachable or attachable airproof cap, closing the outer opening, mounted on the outer end of the tube. The cap is attached to the outer end by means of screw-threads or by any other known airproof connections. There are cap openings with valves on the cap.

In case of the SPLS procedures advantageously the whole tube is rigid.

In case of either solution referred above an optional external fixateur device could be attached to the outer end of any instrument, trocar sleeve, tube or endoscopic device, and said external fixateur device is able to fix the outer end transiently or permanently in a desired position.

In case of either solution above the inner end of any instrument, trocar sleeve, tube or endoscopic device could be fixed via a thread, or a stick or a control rod, being attached to the inner end, to the abdominal wall and/or to an external fixateur device.

The endoscopic device refers to a solution, which has a long cylindrical body advantageously with more than one working channels inside. Advantageously there could be connecting grooves or rails formed on the outer surface of either type of endoscopic device in order to establish additional external connections (e.g. with a thread, stick, control rod, stomach closure device, etc.). According to an advantageous embodiment there could be an articulation formed at the inner end of either type of endoscopic device, and said articulation is bent by a pair of wires and an articulating device. This pair of wires extends through the entire endoscopic device and is connected to the articulating device located at the outer end of the endoscopic device. The inner and the outer ends of either type of endoscopic device are advantageously rigid and the middle part could be flexible or rigid. Either endoscopic device may have optionally a gas channel and a suction-irrigation channel.

According to a possible advantageous solution the endoscopic device is divided. In this case the endoscopic device is partially or totally divided into two parts (upper and lower parts) by a plane that is advantageously parallel with the longitudinal axis. The two parts are connected together by sliding connection, and they are optionally movable back and forth along their longitudinal axis relative to each other. The dividing plane may divide the working channel inside the endoscopic device into two complementary divided working channels. When the two divided parts of the endoscopic device are shifted longitudinally relative to each other, the divided working channels become free at their inner ends. The instruments bent at their inner articulations are easily movable back and forth within the free part of the divided working channels with or without the trocar sleeves. The free part of the divided working channel is advantageous because it allows the telescopic inner end and head of the instrument—i.e. the part that is distal to the inner articulation—to exit from the divided working channel along the full length of its free part in order to reach the interventional area. The length of the free parts of the divided working channels could be changed optionally (increase or decrease) by shifting the two divided endoscopic parts longitudinally relative to one another. According to and advantageous arrangement of the four working channels, the plane dividing the endoscopic device into two longitudinal parts also divides longitudinally two opposite working channels. The other two working channels—advantageously the upper and the lower channels—remain intact. The normal or oblique inner ends of the divided endoscopic device could be transformed into a step-form inner end by the longitudinal shift of the two parts (advantageously only the upper part or only the inner part) relative to one another.

According to a possible advantageous embodiment the outer end of the divided endoscopic device is rigid. The rigid end of the upper part of the device is completed to a full cylinder, in such a way, that the rigid end of the slidable lower part is also inside the cylinder The outer end completed to a full cylinder is airtight and has advantageously four air proof openings with valves, and said openings are the inlet openings of the intact or divided working channels situated within the endoscopic device. The airtight closure of the cylindrical common end may be also achieved by an optionally securable cap with airtight inlet openings and valves.

Advantageously the trocar shaft—i.e. the rigid tube-like continuation of the lower part—exits the common cylindrical end through the lower outer opening. The trocar shaft—provided with a valve—is the external continuation of the intact working channel located inside the lower endoscopic part, and said trocar shaft, which extends through the lower outer opening, has an ear-like handle at the outer end that helps to move the lower endoscopic part longitudinally back and forth. Advantageously the trocar shaft is shifted in and out through the lower outer opening of the common cylindrical end by the help of the ear-like handle, which consequently means the longitudinal back and forth movement of the inner end of the lower endoscopic part. Thereby the size of the step-form inner opening—and consequently the size of the interventional area—is optionally adjustable.

According to another possible solution, the plane dividing the endoscopic device parallel with the longitudinal axis does not divide any of the working channels. Advantageously both the upper and the lower endoscopic parts contain two intact working channels. In this case the shape of the outer end of the endoscopic device could be a common cylinder similarly to the previous solution, except that now two rigid trocar shafts, which are the external continuation of the two working channels of the lower endoscopic part, exit trough the two lower outer openings of the common cylindrical end.

According to another possible solution, the outer ends of the divided endoscopic device are similarly divided as the inner ends, and both outer ends are hermetically sealed. The upper and lower outer ends have airtight outer openings with valves. In this case either endoscopic part—the upper and the lower endoscopic parts are connected together by sliding connection—could be removed from the patient and could be replaced with a larger instrument (e.g. an endoscopic stapler), or through the space of the removed endoscopic part also tissue or organ specimens could be removed.

According to another advantageous embodiment the endoscopic device is solid and undivided. The opening of the inner end of the device could be normal, or oblique or step-form. In case the inner end has a step-form opening there could be one or more working channels divided partially advantageously only at the inner end region, in order to achieve the above detailed advantages. Advantageously the upper and the lower working channels are intact (i.e. undivided) while the other working channels on both sides are divided at their inner ends. Of course a pair of intact (i.e. undivided) upper and a pair of intact lower working channels arrangement is also possible. The outer end of the undivided endoscopic device is hermetically sealed and there are airtight outer openings with valves, and said outer openings are the inlets of the working channels.

Inside the divided working channels of any type of endoscopic device there are sliding connections (e.g. sliding rim, connecting groove or rail) allowing the proper attachment and fixation, and the longitudinal back and forth movement of the inserted trocar sleeve or instrument. This connecting components (e.g. sliding rim, connecting groove or rail) are connected to the connecting components of the instruments or the trocar sleeves.

The outer end of any type of tube or endoscopic device may have a cone shape. This is advantageous because it allows the easier handling of the outer ends of the instruments.

Any type of the previously mentioned instruments, trocar sleeves, tubes or endoscopic devices could be combined to perform the NOTES/SPLS procedures appropriately.

Advantageously any type of tube or endoscopic device may have a protective sheath. The protective sheath is advantageously cone shaped and is made of a strong clingfilm-like material, that on the outer end has a connecting ring or tube—able to connect airtight to the outer end of a tube or an endoscopic device—, and on the inner end it has an expandable ring. The protective sheath covers the tube or the endoscopic device. The protective sheath is inserted via a natural orifice into the abdominal cavity through the wound on the wall of a hollow organ advantageously in a rolled position over the tube or the endoscopic device. When the protective sheath enters the abdominal cavity, the expanding cone shaped inner end with the expandable ring and the contracting wound around the protective sheath prevent to escape the gas from the insufflated abdominal cavity. In addition the protective sheath protects the wall of the hollow organs and the adjacent area against the injuries caused by the moving instruments, and prevents the contact with the contaminated secretions, or with the diseased tissues or organs. The cone shaped inner end (i.e. the inner end has a larger circumference) allows to remove the tissues or organs easier. Of course any other shape of the protective sheath could be among the possible solutions.

According to another solution an independently inflatable endoscopic balloon tube could be placed advantageously on the inner end region of the tube or endoscopic device. This device is placed into the wound on the wall of a hollow organ, in order to prevent gas leakage. When the endoscopic balloon tube is already inserted the air ducts of the balloons extend over the natural orifice.

In any of the previously described instrument—trocar sleeve—tube or endoscopic device system, or instrument—trocar sleeve system, or instrument—tube or endoscopic device system the inserted instruments are able to reliably reproduce all three-dimensional laparoscopic maneuvers by the help of bandings, rotations and telescopic movements.

Any type of the previously described instruments, trocar sleeves, tubes or endoscopic devices may have a disposable or a reusable design.

Any type of the previously described instruments, trocar sleeves, tubes or endoscopic devices may have a design allowing their disassembling, cleansing and reassembling.

The invention further relates to the following accessory devices.

One of such accessory instrument is the access catheter, which enables to create a wound opening on the wall of a hollow organ (e.g. the stomach) during the access phase. The catheter could be inserted into any suitable working channels. There is an electric unit—that is able to cut or coagulate tissues—mounted on the inner end advantageously on the tip of the catheter, said electric unit has an electrical wiring extending along the catheter, and said electrical wiring is connectable to an electric power supply. The electric unit is slightly recessed within the tip of the catheter in order to avoid the direct contact with extended tissue areas. There are two consecutive balloons on the catheter. The one closer to the inner end has advantageously an umbrella-like shape characteristically with a diameter—that is perpendicular to the longitudinal axis—larger than that of the tube or the endoscopic device. The next one is the dilating balloon that has advantageously a cylinder-like shape and its diameter is smaller than that of the tube or the endoscopic device. The balloons are independently inflatable or deflatable, and their air ducts extend over the outer end of the tube or the endoscopic device.

Another such an accessory device is the wound closure device allowing the closure of a wound created on the wall of a hollow organ. According to an advantageous embodiment the wound closure device consists of an implanting tube, an implanting sheath, locking elements, threads and an implanting rod. The groove or rail on the outer surface of the implanting tube could be connected with sliding connection to the rail or groove on the outer surface of the trocar sleeve, tube or endoscopic device. There are locking elements on the inner end of each thread and there is one fixing knob on their outer ends. The locking elements are inside the implanting sheath, and the sheath with the threads is inside the implanting tube. The inner end of the implanting sheath is sharp and there is a longitudinal split on the side of the sheath, and there is an implanting rod located above the locking elements. The locking elements, the implanting rod, the implanting sheath, the threads and the implanting tube are moveable to each other or to a trocar sleeve, tube or endoscopic device, respectively. The implanting rod, the implanting sheath and the implanting tube are advantageously flexible.

The third accessory device is advantageously assembled by rigid components, and allows the optional fixation of the outer and the inner ends of a trocar sleeve, tube or endoscopic device. One end of this fixateur device is fixed independently from the patient, e.g. to the operating table. One type of the external fixateur device could be suitable to fix the thread, or stick or rod connected to the outer surface of the inner ends, while another type of the device is suitable to fix the outer ends. The shape, the angle and the position of the fixateur device is optionally fixable or changeable.

The fourth accessory device could be a modified endoscopic stapler. Advantageously the head of the stapler is rigid and the body is partially or totally flexible. The head and the body are connected together advantageously by an articulation. The stapling surface of the head is advantageously perpendicular or parallel to the longitudinal axis of the device, but any other inclination angle is possible. There is a control thread located between the free ends of the stapling surfaces, and said control thread could be optionally tensioned or relaxed. The thread is situated within the channel that extends throughout the head and the body of the device. The end of the thread extends over the outer end of the stapler. When the control thread is tensioned the desired part of the tissue is directed among the stapling surfaces. Under full tension the thread supports the parallel closure of the mobile jaw of the stapler head. Advantageously there may be a working channel inside, or a groove or rail on the outer surface of the body of the stapler and said groove or rail allows the connection of an accessory device (e.g. a trocar sleeve, a camera, a forceps, etc.). The stapling surfaces may have straight, curved, wavy or any other recently known shape. The diameter of the stapler is preferably smaller than the inner diameter of the tube.

Any further advantageous embodiments are detailed in the subclaims.

In the following part hereof, the invention will be described in detail with reference to the drawings attached hereto showing the advantageous embodiments of the instrument.

BRIEF DESCRIPTION OF THE DRAWINGS

In the drawings,

FIG. 15 shows the already shifted upper and lower parts of the divided endoscopic device with oblique inner ends, each endoscopic parts containing two intact (non divided) working channels that are hermetically sealed at their outer ends, and the two independent parts are connected together by a longitudinal sliding connection, FIGS. 16/A, B and C show additional advantageous embodiments of the connections of the trocar sleeves, FIG. 17/A shows the non divided endoscopic device with an opened inner end being both oblique and step-form, FIG. 17/B shows the cross section of the device according to FIG. 17/A, FIG. 17/C shows a non divided endoscopic device with oblique inner end, FIGS. 18/A to 18/E show a device able to close a wound on a wall of a hollow organ.

DESCRIPTION OF PREFERRED EMBODIMENTS

Figure 1:
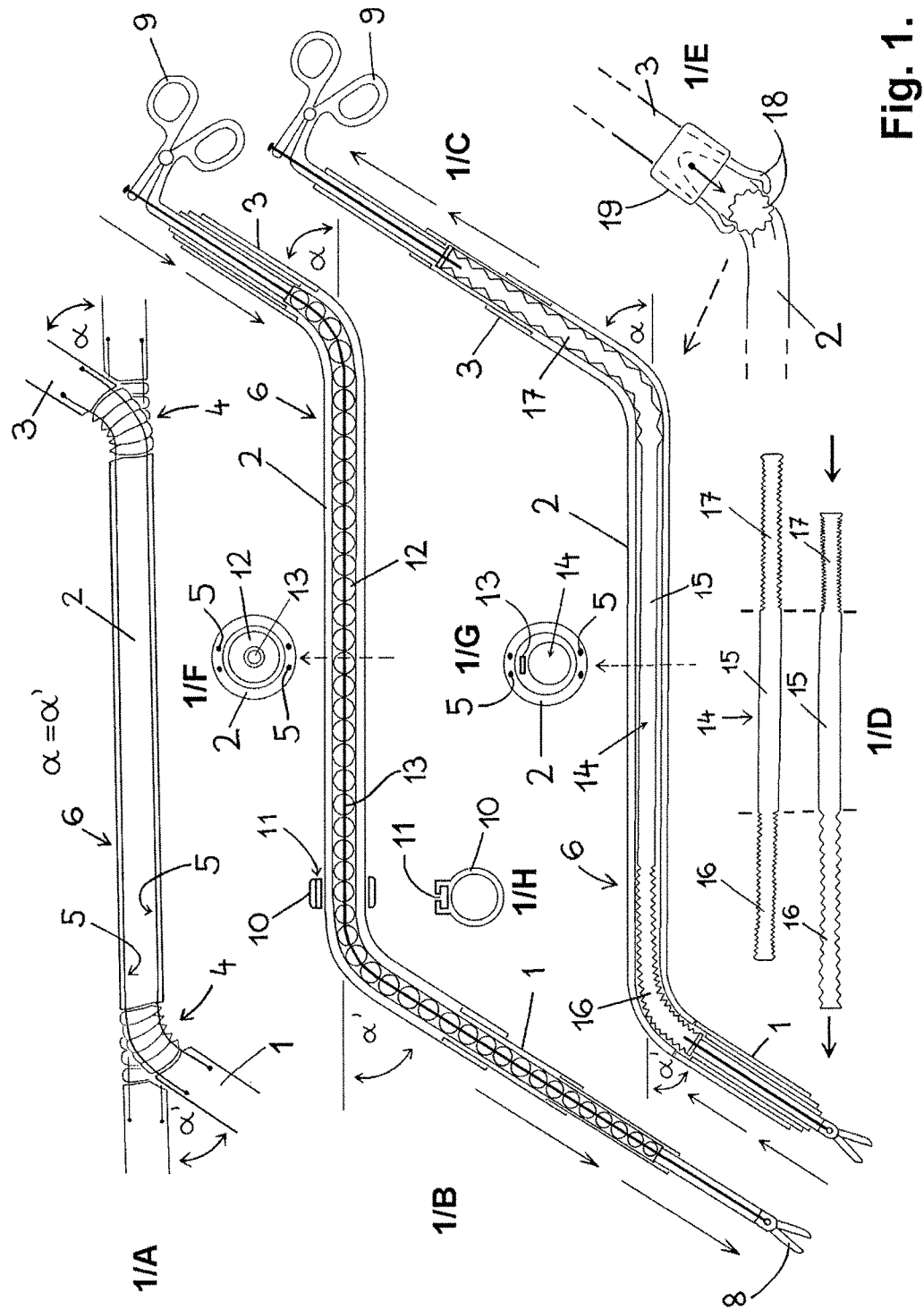
FIG. 1/A shows an exemplary embodiment of a joint-like articulation and its bending system according to the present invention, FIG. 1/B shows an exemplary embodiment of a telescopic instrument with ball-like force transmission particles according to the present invention, FIG. 1/C shows an exemplary embodiment of the telescopic instrument with a hydraulic force transmission unit according to the present invention, FIG. 1/D shows an exemplary embodiment of the advantageously closed hydraulic unit, FIG. 1/E shows an exemplary embodiment of a ratcheting mechanism located at a region of the outer articulation, FIG. 1/F shows the cross section of the instrument with the ball-like force transmission particles according to the present invention, FIG. 1/G shows the cross section of the instrument with the hydraulic unit according to the present invention, FIG. 1/H shows a connecting ring attachable to the instrument according to the present invention, FIG. 1/I (on the drawing page 2/29) shows the longitudinal section of the instrument with a flexible sheath according to the present invention, FIG. 2/A shows an exemplary embodiment of a trocar sleeve according to the present invention, FIG. 2/B shows an exemplary embodiment of the telescopic instrument according to the present invention, FIGS. 2/C and D show a ring with a connecting groove, thread and needle that is attachable to the telescopic instrument according to the present invention, FIG. 2/E shows a ratcheting mechanism located at the outer articulation, FIGS. 3/A and B show an exemplary embodiment of the telescopic trocar sleeve according to the present invention, FIG. 3/C shows an exemplary embodiment of the instrument with flexible middle part according to the present invention, FIG. 3/D shows the ring attachable to the telescopic trocar sleeve according to the present invention, FIG. 3/E shows the ratcheting mechanism mounted on the outer articulation, FIG. 4/A shows an exemplary embodiment of a tube with straight inner end according to the present invention, FIG. 4/B shows an exemplary embodiment of trocar sleeves with sector-like cross sections that are connected together through sliding connections according to the present invention, FIGS. 4/C, D and E show an exemplary embodiment of the inner ends of the telescopic trocar sleeves—with sector-like cross sections—that are connected together through sliding connections according to the present invention, FIG. 4/F shows the cross section of the trocar sleeves (having sector-like cross sections) within the tube according to an exemplary embodiment present invention, FIG. 4/G shows the cross section of the trocar sleeves (having sector-like cross sections) that are connected together through sliding connections according to an exemplary embodiment present invention.

FIG. 1 depicts an advantageous embodiment of a surgical instrument

The surgical instrument 6 (e.g. FIG. 1/B) is inserted into a trocar sleeve 7, and more than one such trocar sleeves 7 (e.g. FIGS. 3/A and B) are inserted into a partially or totally flexible tube 28 (FIG. 9/A) or endoscopic device 66, 103 (FIG. 15, 17). Advantageously the connections between the tube 28 or the endoscopic device 66, 103 and the trocar sleeves 7 and the surgical instruments 6 allow both longitudinal and rotational movements (e.g. FIG. 11). If required further accessory devices (e.g. protector sheath 71—e.g. FIG. 15, wound closure device—FIG. 18, endoscopic stapler 88—e.g. FIG. 30) could be attached to their inner or outer surfaces. Advantageously all connections allow longitudinal movement or sliding along the longitudinal axis and rotation around the longitudinal axis, respectively.

As the FIGS. 1/B and 1/C show, the surgical instrument 6 has three parts: the partially flexible middle part 2 and the two telescopically extendable rigid inner 1 and outer 3 ends. The inner end 1 and the outer end 3 preferably each comprise at least two rigid tubular elements with different diameters adapted to move axially within each other and preventing bending movement of the inner and outer ends 1, 3. The inner and outer ends 1, 3 are connected to the middle part 2 through joint-like inner and outer articulations 4, respectively. Advantageously the portions of the middle part 2 adjacent to the articulations 4 are also rigid. The cross section of the instrument 6 is advantageously circular.

Advantageously the outer end 3 and the inner end 1 of the instrument 6 are simultaneously rotatable relative to the middle part 2 at the articulations 4 by the same rotational angle and in the same rotational direction (when the middle part 2 is in straight position the rotational axes of the outer end 3 and inner end 1 at the articulations 4 are parallel with each other), as if the outer end 3 and the inner end 1 were the components of one traditional laparoscopic instrument. By ensuring simultaneous rotation of the outer end 3 and of the inner end 1 by the same angle and in the same direction the articulation angle at the inner articulation 4 always remains the same as the articulation angle at the outer articulation 4.

A first force transmission unit is provided for maintaining the same articulation angle at the first articulation 4 and at the second articulation 4 by rotating the trocar inner end 1 with respect to the trocar middle part 2 by the same rotational angle and in the same rotational direction as the trocar outer end 3 is rotated relative to the trocar middle part 2.

The rotation of the inner 1 and the outer 3 ends are executed advantageously only in one common plane (in case the middle part 2 is in straight position) and advantageously through a pair of antagonistic wires 5. Said wires extend opposite to one another from the inner end 1 throughout the articulations 4 and the middle part 2 to the outer end 3. According to another embodiment the articulations 4 could be bendable in more than one common plane utilizing more than one pair of antagonistic wires 5. Any other known technical solutions are also acceptable to achieve the above described rotating mechanism. Such possible solution could be a flexible or rigid pusher rod that is placed within the middle part 2 and is connected to both the outer 3 and the inner 1 ends. In fact the instrument 6 (FIG. 3/C) inside a trocar sleeve 7 may have a function similar to the pushing rod, if the instrument 6 is resistant against compression.

Preferably there is a releasable ratchet mechanism 18 (FIG. 1/E) located at the articulation 4 that connects together the middle part 2 and the outer end 3. The ratchet mechanism 18 has a lock 19 that allows the temporary or permanent fixation of the desired angle between the middle part 2 and the outer end 3 and thereby between the middle part 2 and the inner end 1.

The telescopic ends 1, 3 preferably are rigid straight tubes of different diameter. The tubes are insertable into one another. The surgical instrument 6 has a head 8, which is located on the inner telescopic end 1, and advantageously it is constructed similarly as the head of any laparoscopic instrument known in the art (including the camera as well). A handle 9 is provided on the outer telescopic end 3 of the surgical instrument 6, and advantageously it is also constructed similarly as the handle of any laparoscopic instrument known in the art (including the camera as well). The opening and the closing movements of the handle 9 of the instrument 6 control the function of the head 8 in a known way with the help of a motive wire 13 that extends from the outer end 3 through the middle part 2 to the inner end 1.

Figure 5:
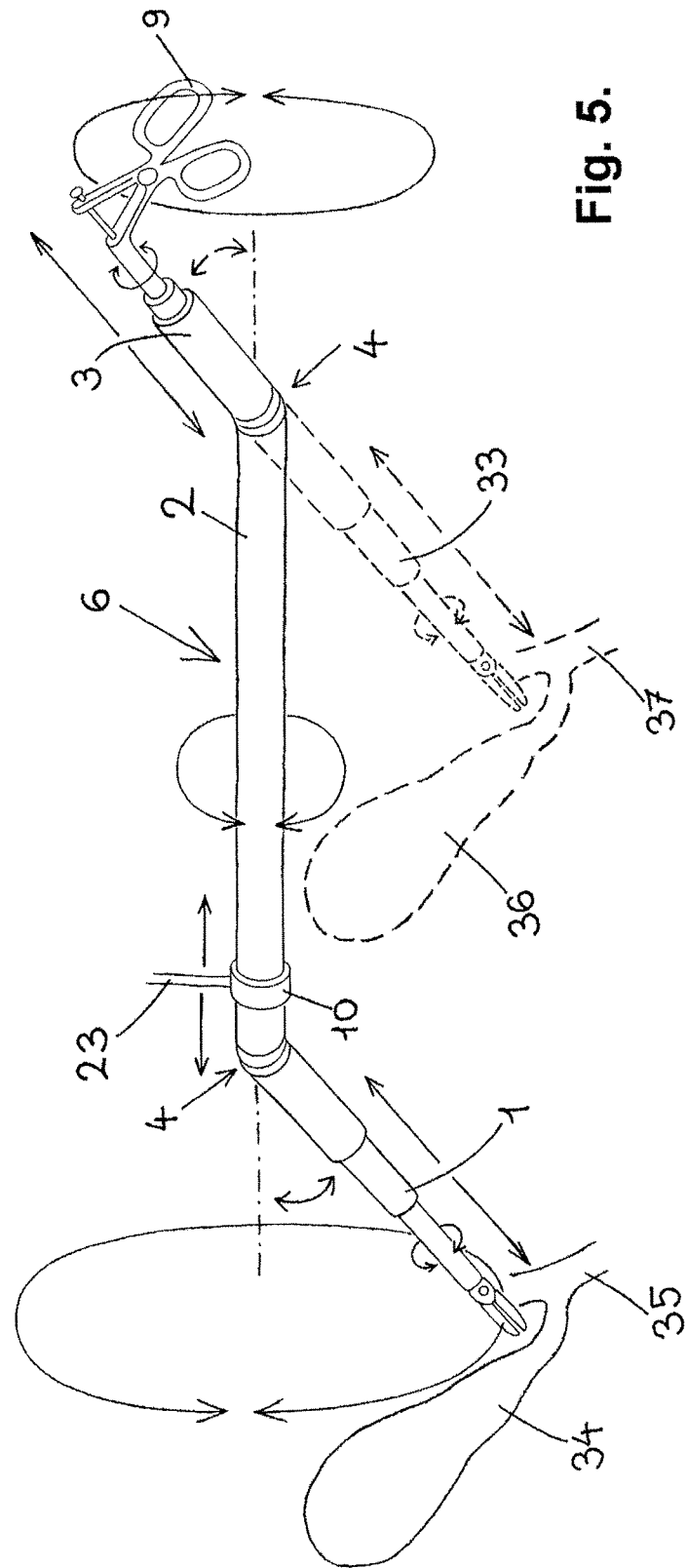
FIG. 5 shows the possible movements of the instrument and its similarity to the movements of a traditional laparoscopic device by illustrating the inner virtual end (dashed line) as the straight continuation of the outer end, FIGS. 6/A, B, C, D, E and F show the possible movements of the instrument according to the present invention.
Figure 6:
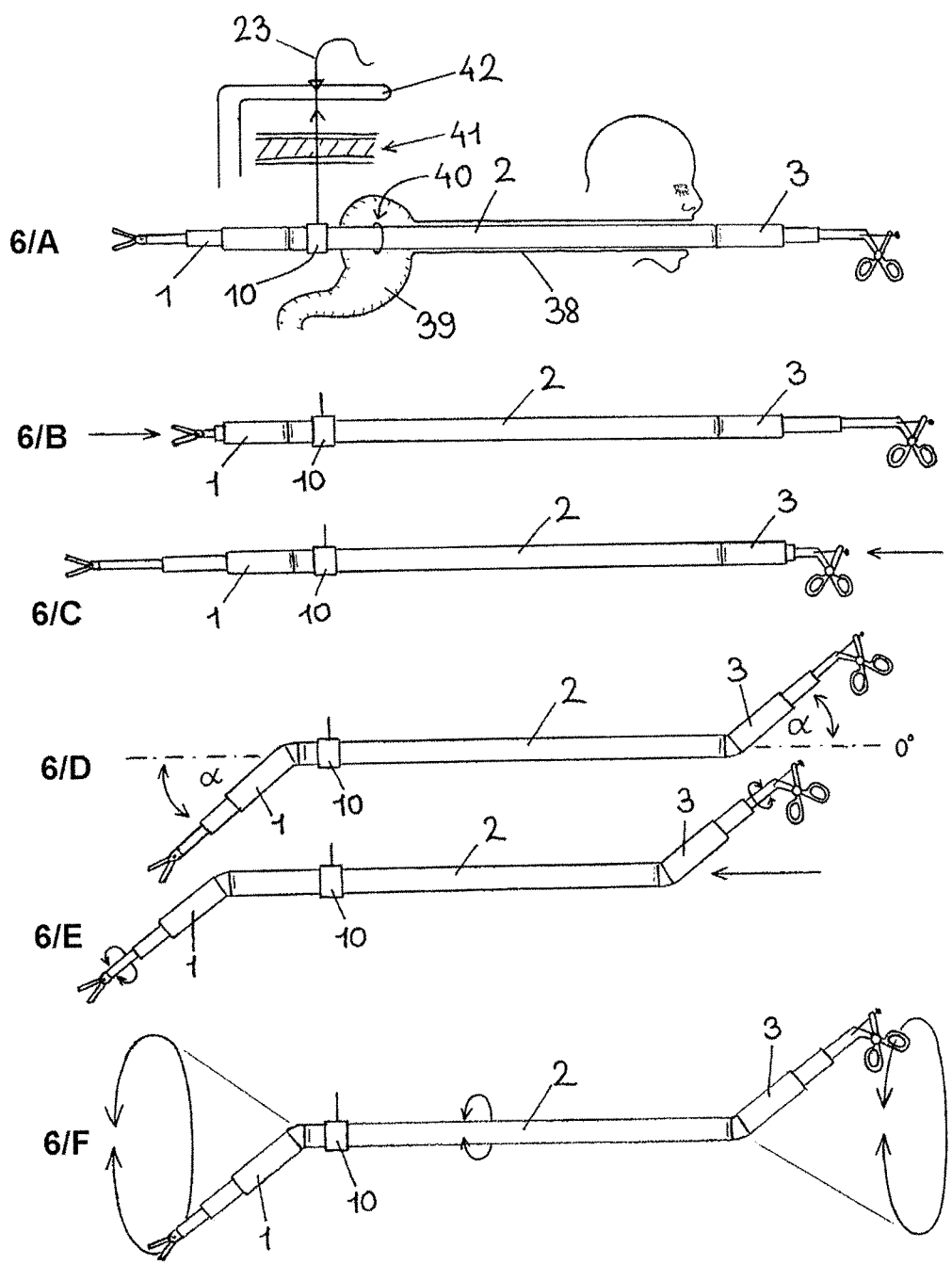

The head 8 situated on the inner end 1 of the instrument 6 is rotatable around the longitudinal axis (FIGS. 5 and 6/E). The rotation of the head 8 is controlled by the rotation of the outer end 3 of the instrument 6, advantageously without the need to rotate the handle 9. The rotation of the handle 9 advantageously is independent from the rotation of the head 8. Advantageously the head 8 located on the inner end 1 and the outer end 3 rotates with the same degree. According to a preferred embodiment the rotation of the head 8 and the inner end 1 by the outer end 3 is executed via the connected force transmission particles 12—said connections among the particles 12 resist torsion around the longitudinal axis as described before. According to another preferred embodiment the rotation of the head 8 is executed via the flexible sheath 108 that also resists torsion around the longitudinal axis. Of course any other known solutions can be used that allow rotation of the head 8.

In spite of the fact that the outer and the inner telescopic ends 3, 1 are separated from each other by the middle part 2, they move together simultaneously, as if they were the straight continuation of each other, similarly to the movements of the inner and outer ends of a straight traditional laparoscopic instrument. When, for example, the outer telescopic end 3 is pushed to some extent, that is, its length is reduced, the length of the inner telescopic end 1 becomes simultaneously elongated with the same extent, and vice versa. This movement is directed by a second force transmission unit situated inside the surgical instrument 6.

According to an advantageous embodiment this second force transmission unit is located inside a channel of the instrument 6 and advantageously consists of ball shaped force transmission particles 12 (FIG. 1/B). The channel extends from the inner telescopic end 3 through the middle part 2 to the outer telescopic end 3. The full length of the channel is filled up with balls 12. The diameter of the ball is somewhat smaller than the inner diameter of the channel. Advantageously there are holes in the middle of the balls 12, and the motive wire 13 travels through these holes from the handle 9 to the head 8. Advantageously the channel is provided with antifriction material. Advantageously the ball like force transmission particles 12 are able to pass easily through the channels at the articulations 4. When the handle 9 of the instrument 6 is pushed forward, the handle 9 pushes the last ball 12 in the channel of the outer telescopic end 3. The adjacent balls 12 transfer this pushing force to one another, and finally the first ball in the channel of the inner end 1 pushes forward the head 8 of the instrument 6, resulting in the elongation of the inner telescopic end 3. To execute the movement in the opposite direction, that is to reduce the length of the inner telescopic end 1, it is advantageous to utilize a wire that connects the two telescopic ends 1, 3 together, which may correspond with the motive wire 13. When pulling the handle 9 of the instrument 6, the outer telescopic end 3 becomes elongated and the wire 13—fixed to the handle 9—simultaneously pulls the inner telescopic end 1. If the free transmission is guaranteed, any other form distinct from the ball shape is suitable. The bendable connections among the force transmission particles 12, which are threaded by the motive wire 13, are designed to resist their compression along the longitudinal axis and to resist their torsion to each other around the longitudinal axis.

According to another advantageous embodiment the force transmission unit is a hydraulic unit 14 advantageously with an elastic capsule, and said hydraulic unit 14 is located inside the channel described above (FIG. 1/D). According to an advantageous embodiment, the hydraulic unit 14 has three parts: inner end 16, outer end 17 and middle part 15. The three parts of the hydraulic unit 14 communicate with one another and they form together one common cavity. This hydraulic unit 14 is a closed system and the hydraulic fluid does not communicate with the outer environment, it only flows through the three parts of the common cavity. The middle part 15 of the hydraulic unit is located advantageously in the channel of the middle part 2 of the instrument 6, and their lengths are equal, and said middle part 15 of the hydraulic unit 14 is fixed to the channel in order to avoid shifting. The inner and the outer ends 16, 17 of the hydraulic unit 14 are located inside the channels of the inner 1 and the outer 3 telescopic ends of the instrument 6. The inner 16 and the outer 17 ends of the hydraulic unit 14 are advantageously designed to allow only longitudinal expansion or reduction along their longitudinal axis without any change in their diameter. The capsules of the ends 16, 17 of the hydraulic unit 14 are advantageously able to move within the channels of the ends 1, 3 of the instrument 6 along its longitudinal axis. One possible advantageous solution regarding the ends 16, 17 of the hydraulic unit 14 would be the accordion like folding of the walls of both ends 16, 17. When the outer telescopic end 3 is compressed longitudinally because the handle 9 of the instrument 6 is pushed, the accordion shaped outer end 17 of the hydraulic unit 14 becomes simultaneously compressed along its longitudinal axis. Thereby the elevated pressure within the outer end 17 of the hydraulic unit 14 is transferred through the fixed hydraulic middle part 15 to the inner hydraulic end 16 resulting in the longitudinal expansion of the accordion folded inner hydraulic end 16 that leads to the elongation of the telescopic inner end 1 as well. Advantageously the extent of the elongation and the extent of the shortening are equal. Along with the accordion folded design, a similar result can be achieved, if the wall of the hydraulic unit 14 is made of appropriately elastic material. To execute the movement in the opposite direction in order to reduce the length of the inner telescopic end 1, it is advantageous to utilize a wire that connects the two telescopic ends 1, 3 together, and for this purpose the motive wire 13 is also acceptable. When pulling the handle 9 of the instrument, the outer telescopic end 3 becomes elongated and the wire 13—fixed to the handle 9—simultaneously pulls in the inner telescopic end 1.

Yet another possible design of the force transmission unit is a flexible sheath 108 placed within the channel of the instrument 6, which, according to an advantageous solution, is a coiled spring or a plastic tube (FIG. 1/I on drawing page 2/29). Advantageously the flexible sheath 108 resists compression along the longitudinal axis and also resists torsion around the longitudinal axis. Advantageously the flexible sheath 108 has insulating properties. The flexible sheath 108 is back and forth slidable within the channel of the instrument 6, thereby the telescopic movements of the outer 3 and the inner 1 ends could be executed simultaneously, and because of the flexibility of the sheath 108 it moves easily through the articulations 4 as well. The motive wire 13 is inside the flexible sheath 108.

On the middle part 2 of the instrument at least one connecting ring 10 (FIG. 1/H) is placed advantageously to allow connection between the tube 28 and the instrument 6. The instrument 6 is easily rotatable within the ring 10. There is a connecting groove 11 formed on the outer surface of the ring 10. According to another advantageous embodiment, a thread 23 with needle 24 is connected to the ring 10 which helps to fix of the middle part 2 of the instrument 6 to any part of the abdominal wall 41 (FIGS. 2/D and 8).

Figure 4:
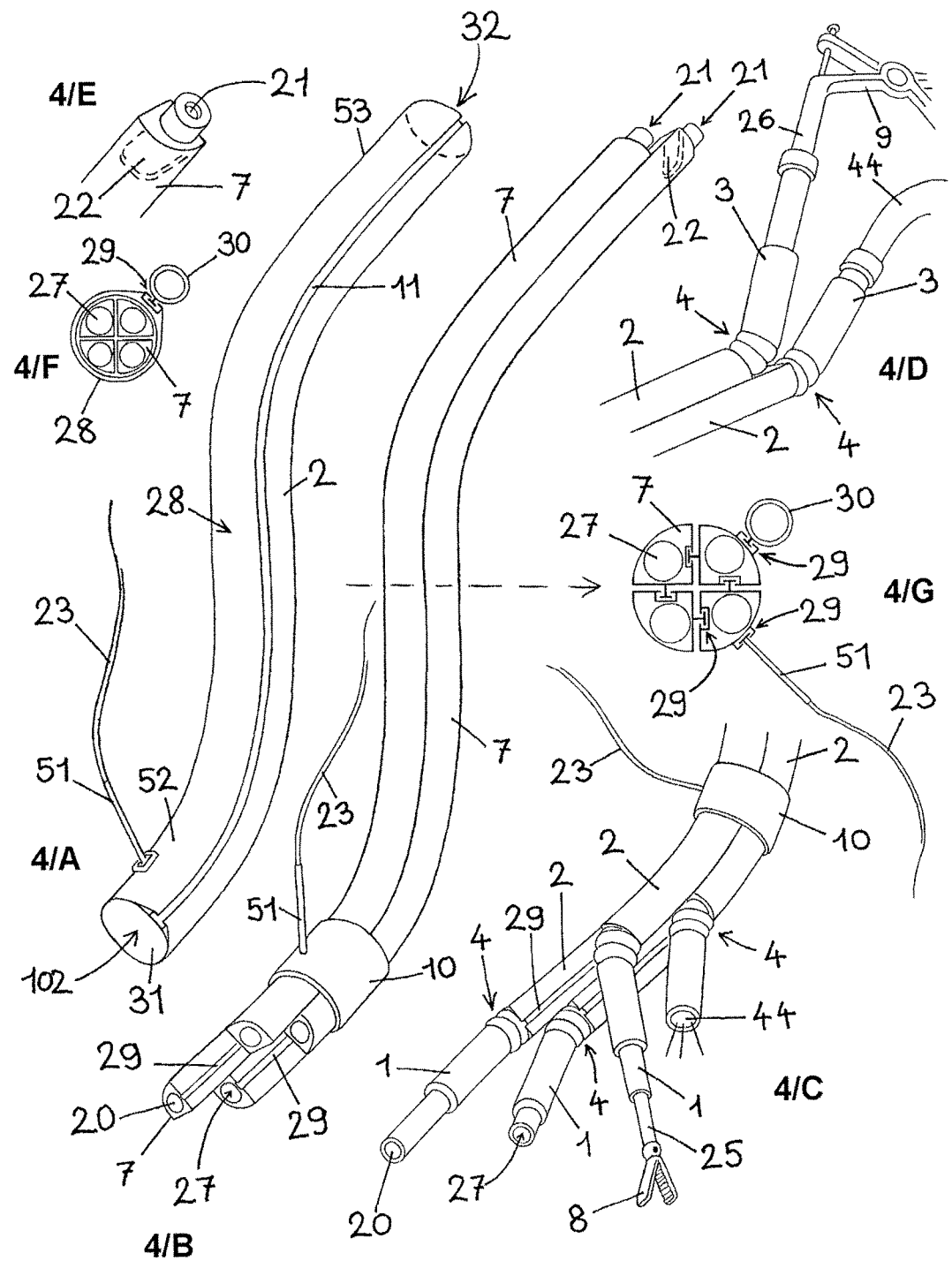

According to another advantageous embodiment the instrument 6 is arranged within a simple trocar sleeve 7 (FIG. 4/A). Preferably the trocar sleeve 7 can be inserted in the tube 28 such that there is a sliding connection 29 between the tube 28 and the trocar sleeve 7, and the middle part 2 of the instrument 6 is located within the trocar sleeve 7. The middle part 2 of the instrument 6 is advantageously longer than the trocar sleeve 7, whereby the articulations 4 and the inner and outer ends 1, 3 of the instrument 6 are outside of the trocar sleeve 7. The instrument 6 is rotatable and slidable back and forth within the trocar sleeve 7. Advantageously there is a valve 22 and an airtight ring 21 on the outer end 3 of the trocar sleeve 7 (FIG. 4/E). Preferably, a plurality of trocar sleeves 7 may be connected to each other, each trocar sleeve 7 being adapted to receive an instrument 6 within its working channel 27. In this case the cross section of the trocar sleeves 7 could have a sector-like form, e.g., four trocar sleeves 7 with a quarter sector cross-section may be connected to each other as illustrated in FIGS. 4/B and 4/F. The trocar sleeves 7 could be rigid or flexible.

Figure 2:
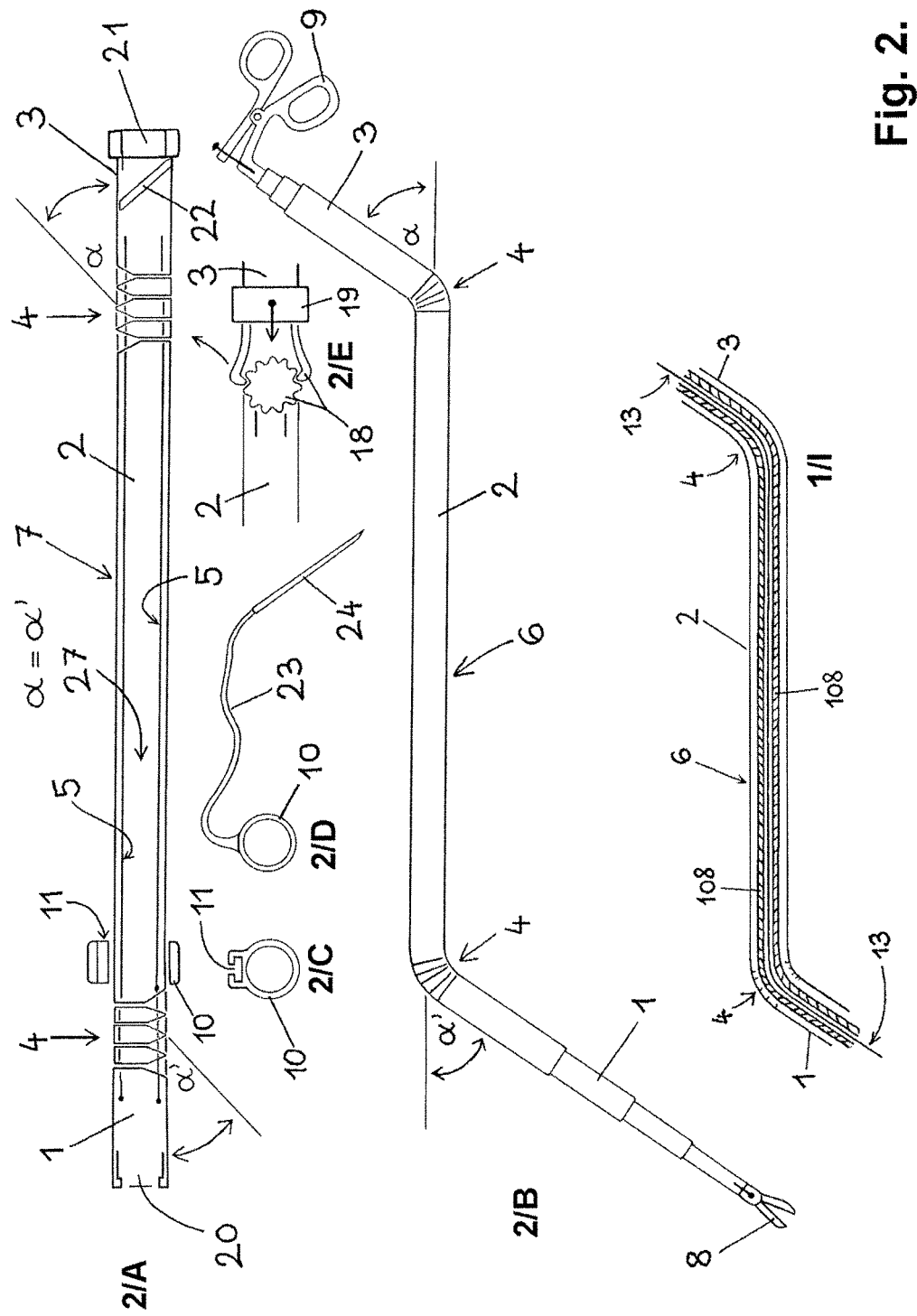

According to another advantageous embodiment the instrument 6 has three main components: the partially flexible middle part 2 and the rigid telescopically extendable outer and inner ends 3, 1 which are connected to the middle part 2 through outer and inner joint-like articulations 4 (FIG. 2/B). According to this solution the instrument 6 is received within a trocar sleeve 7 which has a partially or totally flexible middle part 2, and rigid outer and inner ends 3, 1 that are connected to the middle part 2 through outer and inner articulations 4 (FIG. 2/A). The second force transmission system of the instrument 6 can be the same as described above. However, according to this embodiment the instrument 6 has no wire to execute the rotation of the telescopic ends 1, 3, Instead the trocar sleeve 7 is provided with the first force transmission system. According to the present embodiment the rotation of the outer and the inner ends 3, 1 are executed by the antagonistic wires 5 located within the trocar sleeve 7. Advantageously the ratchet mechanism 18 is mounted on the outer articulation 4. There is advantageously a valve 22 and an airtight ring 21 located on the outer end 3 of the trocar sleeve 7.

Preferably the trocar sleeve 7 is inserted in a tube 28. The length of the middle part 2 of the trocar sleeve 7 is advantageously longer than the length of the tube 28. Preferably there is a sliding connection 29 between the trocar sleeve 7 and the tube 28. The length of the middle part 2 of the instrument 6 is advantageously longer than the length of the middle part 2 of the trocar sleeve 7. The instrument 6 within the trocar sleeve 7 is easily moveable along the longitudinal axis and also rotateable around the longitudinal axis.

Figure 3:
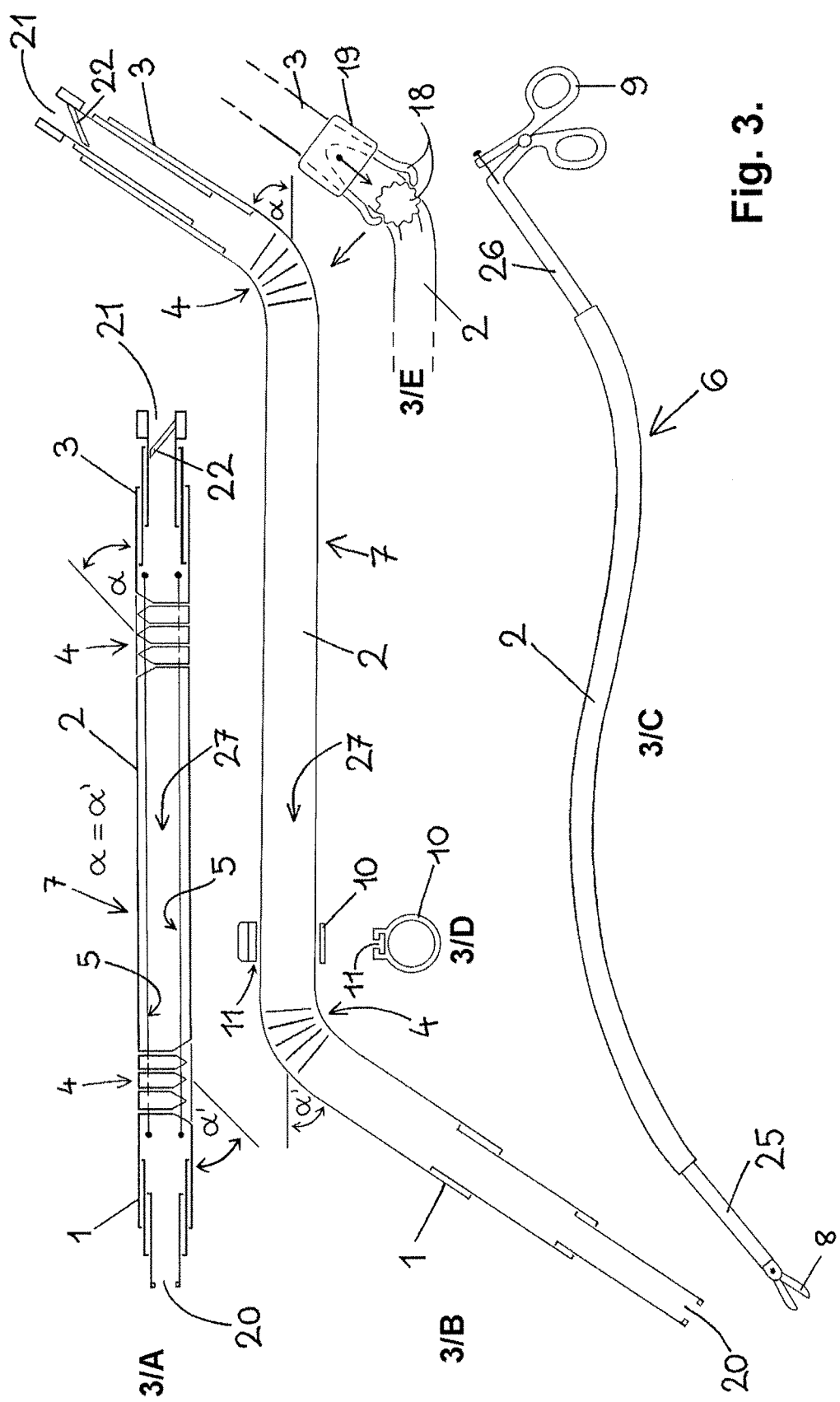

According to another advantageous embodiment, the instrument 6 has three main parts: the flexible middle part 2 and non-telescopic rigid outer end 26 and inner end 25 (FIG. 3/C). The motive wire 13 is situated inside the instrument 6. There is no additional force transmission unit within the instrument 6.

Preferably the instrument 6 constructed this way is arranged within a trocar sleeve 7 which has a partially or totally flexible middle part 2 and rigid telescopic outer and inner ends 3, 1, which are connected to the middle part 2 through outer and inner articulations 4 (FIGS. 3/A and 3/B). The simultaneous bending of the outer and inner articulations 4 are executed by the first force transmission system. The first force transmission unit maintains the same articulation angle at the first articulation 4 and at the second articulation 4 by rotating the trocar inner end 1 with respect to the trocar middle part 2 by the same rotational angle and in the same rotational direction as the trocar outer end 3 is rotated relative to the trocar middle part 1. According to the present embodiment the first force transmission system comprises antagonistic wires 5 situated within the wall of the trocar sleeve 7.

According to this embodiment, the second force transmission system is the instrument 6 arranged within the trocar sleeve 7. The instrument 6 is dimensioned such as to transfer axial movement of the trocar outer end 3 to the trocar inner end 1 relative to the trocar middle part 2 by the same extent but in the opposite direction (when the outer end 3 moves in the direction of the middle part 2, the inner end 1 moves away from it and vice versa). This is achieved by displacing the instrument 6 within the trocar sleeve 7. Upon advancing the instrument 6 the telescopic trocar inner end 1 is elongated as the telescopic trocar outer end 3 is compressed, and upon retraction of the instrument 6 the telescopic trocar inner end 1 is contracted as the telescopic trocar outer end 3 is elongated. Accordingly, the simultaneous elongation and shortening of the telescopic ends 1, 3 of the trocar sleeve 7 are the results of the forward or backward movements of the instrument 6 within the trocar sleeve 7.

Similarly to the previously disclosed embodiments, the ratchet mechanism 18 could be formed on the outer articulation 4 (FIG. 3/E). Advantageously, the trocar sleeve 7 is inserted within a tube 28 and there is a sliding connection 29 between the trocar sleeve 7 and the tube 28, which allows free movements along the longitudinal axis. Advantageously the sliding connection 29 is accomplished by at least one connecting ring 10 situated on the middle part 2 of the trocar sleeve 7, and said ring 10 is freely rotateable around the middle part 2 (FIG. 3/D). Advantageously the ring 10 has a connecting groove 11 that is connected with a rail 50 mounted on the inner surface of the tube 28 (e.g. FIG. 10). Preferably, there is an airtight valve 22 and a ring 21 on the outer end 3 of the trocar sleeve 7 (FIGS. 3/A and 3/B).

According to an advantageous embodiment, a plurality of the trocar sleeves 7 according to the invention are connected to one another through sliding connections 29 mounted longitudinally on their outer surfaces, and each trocar sleeve 7 is connected with the two adjacent trocar sleeves 7 to form a cylindrical arrangement (FIG. 4/B). Advantageously, four connected trocar sleeves 7 are sufficient to perform most surgical interventions. In this case the cross section of each connected trocar sleeve 7 is advantageously a quarter sector, and they together form a full circle (FIG. 4/G), thereby the common outer cylindrical form makes a gentler intervention possible (e.g. when penetrating through the gastric wall 39 of a patient). The sliding connections 29 (a groove 11 or a rail 50 fitting to one another) are situated on the flat superficia of the trocar sleeves 7, and said sliding connections 29 allow the longitudinal movements of the trocar sleeves 7 relative to each other. This kind of trocar sleeve 7 has two flat superficia, one of them is provided with the groove 11 and the other one is provided with the rail 50 that fits into the groove 11 of a neighbouring trocar sleeve 7. The cross sections of the working channels 27 of the trocar sleeves 7 are advantageously rounded. This kind of trocar sleeves 7 could be partially or totally flexible or rigid. The inner end 3 of the trocar sleeves 7 may have an oblique plane which makes the penetration through the stomach wall 39 easier (e.g. as in case of the surgery illustrated in FIG. 19/A).

The trocar sleeves 7 attached to each other in this manner may be of the type illustrated in FIGS. 3/A and 3/B, having rigid telescopic outer and inner ends 3, 1 which are attached to the middle part 2 through articulations 4 (FIGS. 4/C and 4/D). Advantageously the cross sections of the telescopic ends 1, 3 are round, and said ends 1, 3 are rotatable relative to the middle part 2 around the longitudinal axis. In this case there is no separate second force transmission unit to actuate the telescopic ends 1, 3. This telescopic function is executed by the surgical instrument 6 located within the working channel 27 of the telescopic trocar sleeve 7. The instrument 6 has a flexible middle part 6 and rigid outer 26 and inner ends 25 (FIG. 3/C), and is able to move longitudinally forth and back within the working channel 27. The simultaneous rotation of the telescopic ends 1, 3 at their articulations 4 are advantageously ensured by a pair of antagonistic wires 5 located within the trocar sleeve 7, which act as the first force transmission system. At the outer end 3 of the trocar sleeve 7 preferably there is an airtight valve 22 and a sealing ring 21.

The skilled person will appreciate that there are several other possible ways to connect the trocar sleeves 7 to each other.

Figures 7, 8:
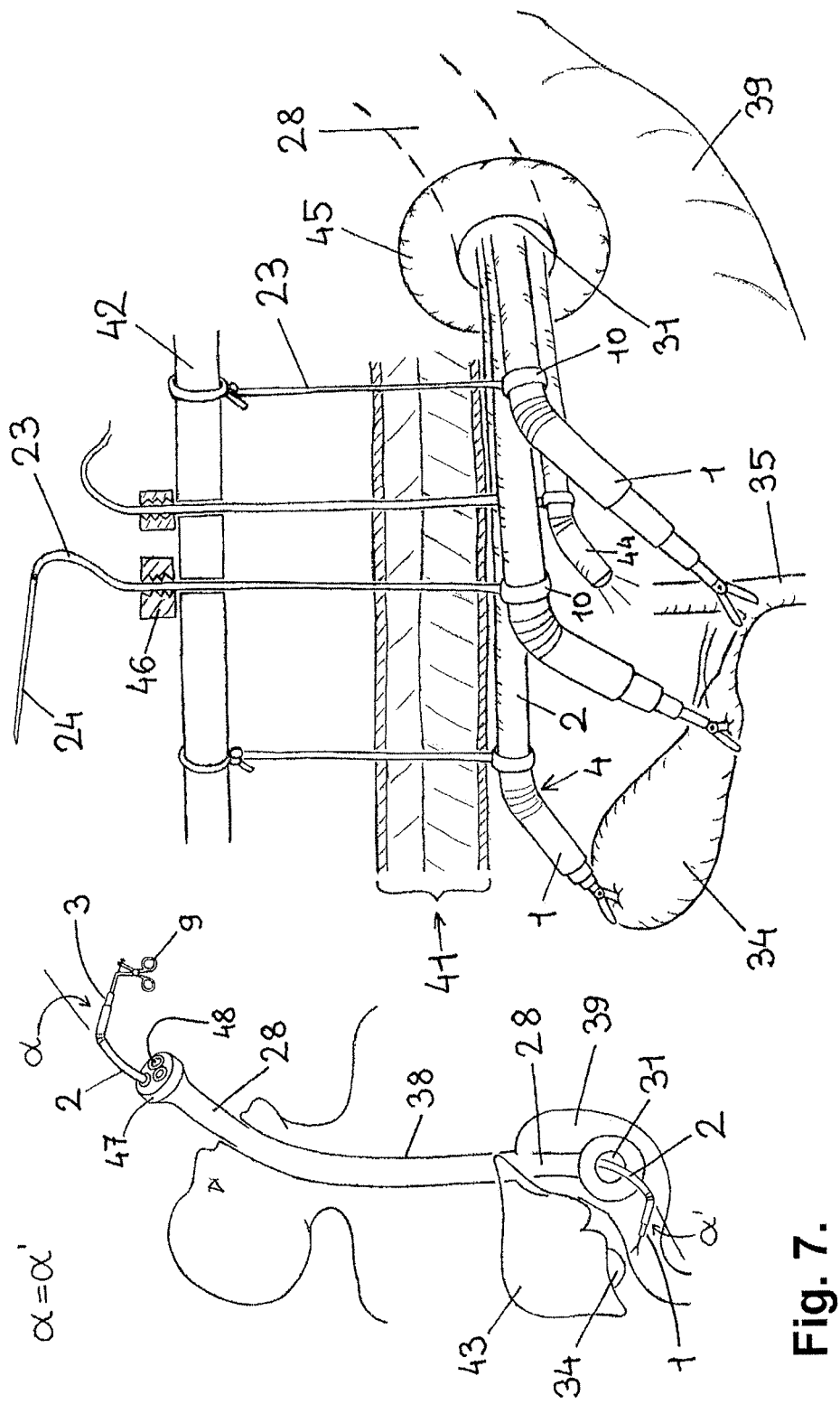
FIG. 7 shows a possible position of a laparo-endoscopic system according to the present invention inserted into a patient.
FIG. 8 shows one possible position of the laparo-endoscopic system according to the present invention arranged to perform the removal of the gall bladder, FIG. 9/A shows preferred embodiment of the tube with a step-form opened inner end according to the present invention, FIG. 9/B shows the oblique opened inner end of the tube according to the present invention, FIG. 9/C shows an exemplary embodiment of the tube, wherein the opened inner end is both oblique and step-form at the same time, FIG. 9/D shows an endoscopic balloon tube that could be pulled over the tube according to the present invention, FIG. 9/E shows an exemplary embodiment of a cup according to the present invention that is able to hermetically seal the outer end of the tube, FIG. 9/F shows two possible cross sections of the tube according to the present invention.

For example, according to an advantageous embodiment, additional trocar sleeves 7 are connected to the outer surface of a double trocar sleeve 99 through sliding connections 29 (FIG. 16/A). Advantageously the trocar sleeves 7 are attached to the junction part of the double trocar sleeve 99. In addition further connecting grooves 11 or rails 50 could be formed on the outer surfaces of the double trocar sleeve 99 or on the additionally attached trocar sleeves 7 to connect them e.g. with a thread 23, stick 51 or rod 61 to ensure their fixation to the abdominal wall 41 (similar to FIGS. 8 and 11).

Figure 20:
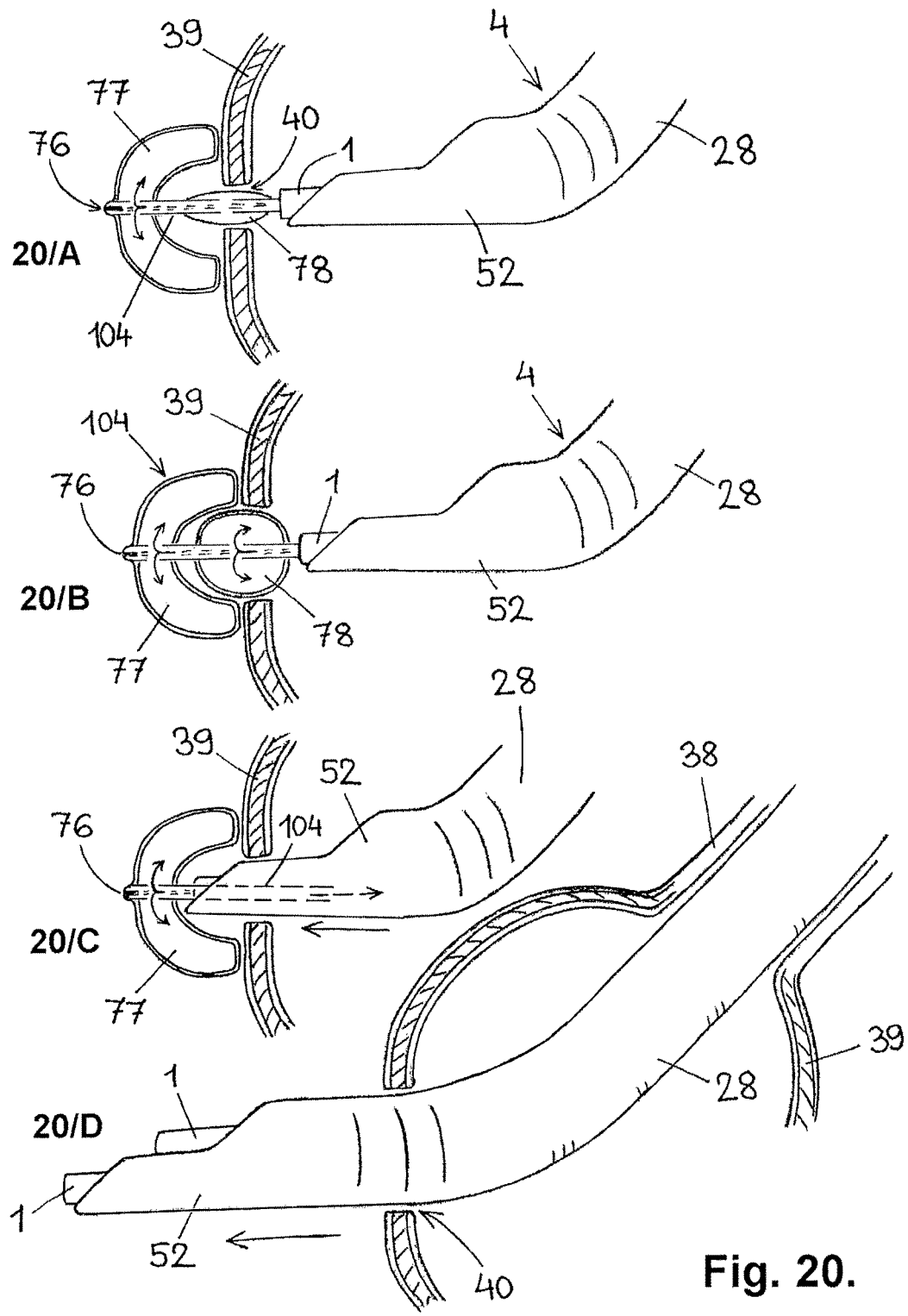

According to another advantageous embodiment, the trocar sleeves 7 are connected to the outer surface of a trocar guide 98 through sliding connections 29 (FIG. 16/B). The connecting grooves 11 or rails 50 are mounted on the outer surface of the trocar guide 98. Inside the trocar guide 98 a smaller diameter working channel 27 could be situated, which could be used to insert e.g. a ballooned access catheter 104 (FIGS. 20/A, 20/B and 20/C). The inner end of the trocar guide 98 is advantageously sharp.

According to a further advantageous embodiment the additional trocar sleeves 7 are attached to a central trocar sleeve 7 through sliding connections 29 (FIG. 16/C). Advantageously the outer cross section of the central trocar sleeve 7 is optional, while the cross section of the working channel 27 inside the central trocar sleeve 7 is round. Advantageously there could be further channels located inside the central trocar sleeve 7, e.g. gas 64 or suction-irrigation 65 channels. The connecting grooves 11 or the rails 50 are mounted on the outer surface of the central trocar sleeve 7.

A tube 28 is not necessary to introduce the connected trocar sleeves 7. The trocar sleeves 7 could be fixed to the abdominal wall 41 transiently or permanently with a ring 10 located advantageously near to the inner end 1 of the middle part 2 (e.g. similar to FIG. 8). The fixation is possible with a thread 23 with a needle 24, or with a rigid stick 51 or with a control rod 61 (e.g. FIG. 2/D or 11). The connected trocar sleeves 7 within the ring 10 are free to move along and to rotate around the longitudinal axis, respectively. In case no tube 28 is used, advantageously there could be connecting grooves 11 or rails 50 formed on the outer surfaces of the trocar sleeves 7 to allow the connection of other endoscopic devices 30.

Figure 10:
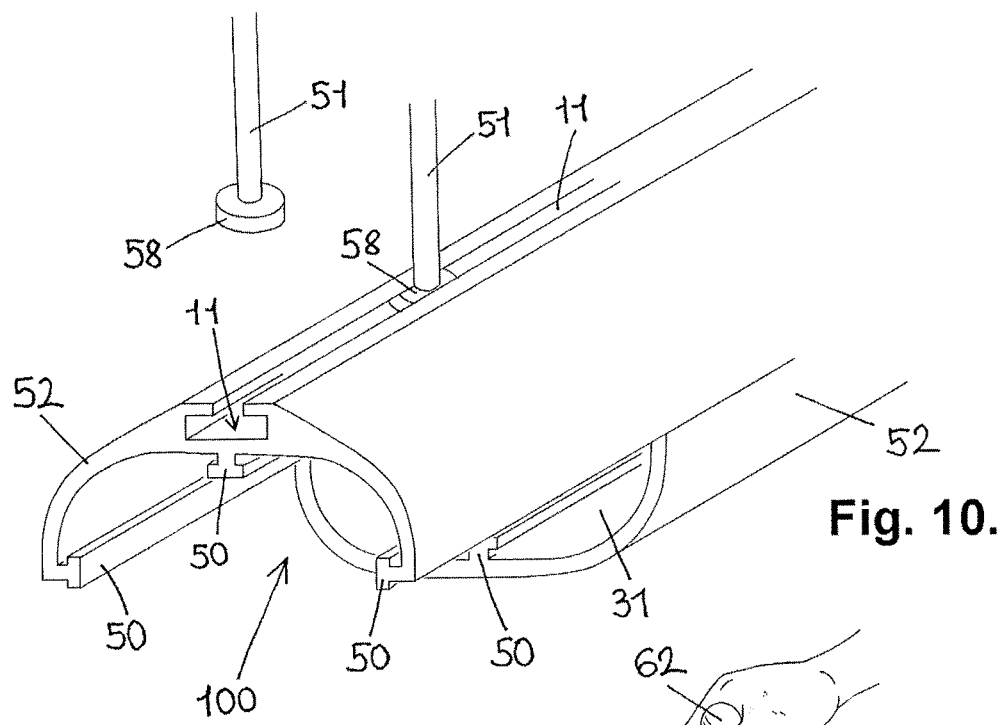
FIG. 10 shows an advantageous embodiment of the step-form opened inner end of the tube according to the present invention.
Figure 11:
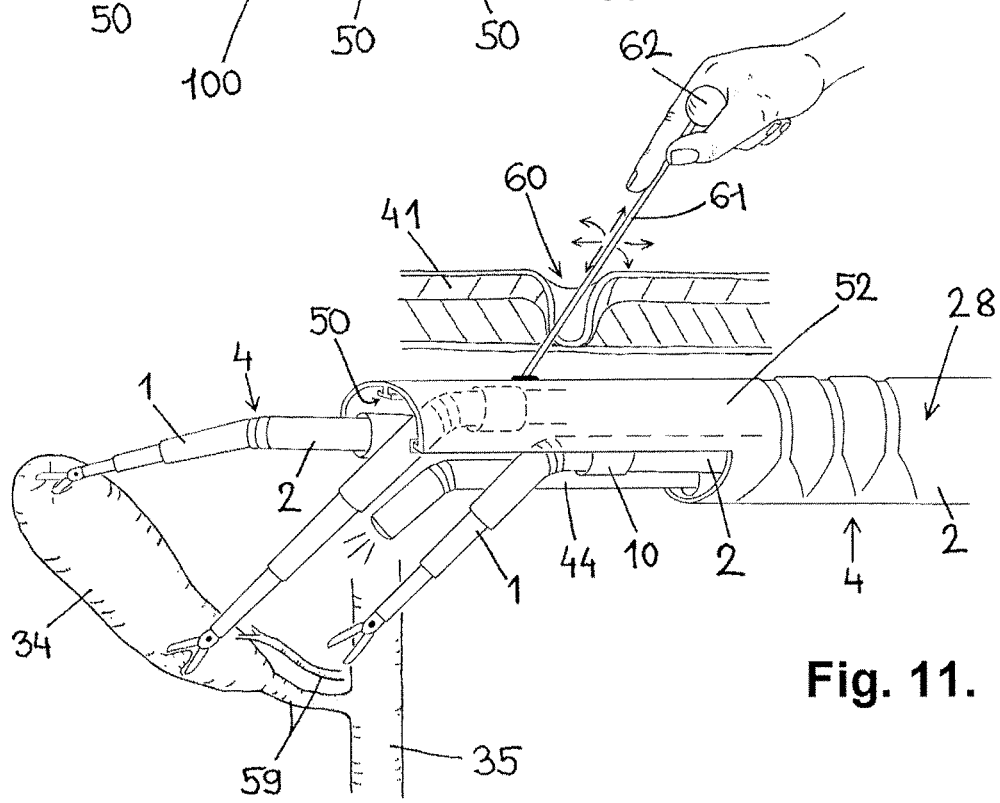
FIG. 11 shows a preferred position of the laparo-endoscopic system with step-form opened inner end during gall bladder surgery, and the advantageous use of the control rod, respectively, FIG. 12/A shows an advantageous embodiment of the divided endoscopic device according to the present invention with normal (straight) inner ends and a protective sheath, FIG. 12/B shows the longitudinal sliding of the parts of the previous endoscopic device and the trocar shaft and the protective sheath, FIGS. 12/C and D show the advantageously oblique inner ends of the divided endoscopic device according to the present invention in normal and in shifted positions, respectively, FIG. 12/E shows the possible elliptical cross section of the endoscopic device according to the present invention, FIGS. 13/A and B show the longitudinal sections of the divided endoscopic device advantageously with oblique inner ends in normal and in shifted positions, respectively, FIGS. 13/C and D show the advantageous cross sections of the divided endoscopic device according to the present invention, FIG. 13/E shows the cross sections of the instrument with a trocar sleeve or a connected ring that are insertable into the working channel of an endoscopic device according to the present invention, FIGS. 14/A and B show the normal and the shifted positions of the normal (straight) inner ends of the upper and lower endoscopic parts according to the present invention each containing two intact working channels inside, FIG. 14/C shows the common cylindrical end of the previous endoscopic device with two trocar shafts and with the articulating device.
Figure 27:
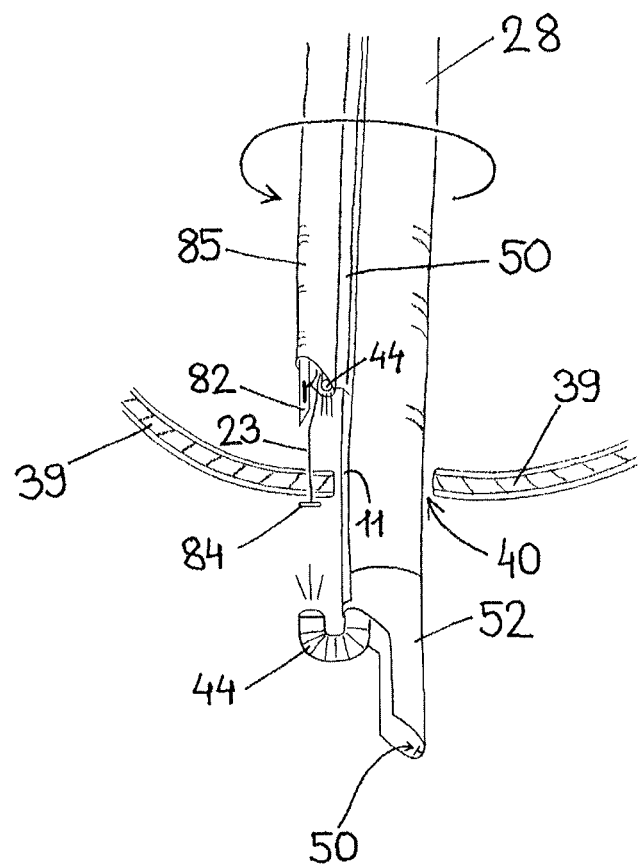
FIG. 27 shows the closure procedure of the wound on the wall of a hollow organ by the help of a tube according to the invention having step-form opened inner end and a camera, and by the help of the wound closure device according to the invention attached to the tube.

The trocar sleeves 7 connected together by sliding connections 29 (FIGS. 4/B, C, D and G) are also insertable into the abdominal cavity or fixable to the abdominal wall 41 by the help of a partially or totally flexible simple tube 28 (FIG. 4/A). In this case there is no groove 11 or rail 50 formed inside the tube 28, they are formed only on the outer surface of the tube 28 (FIG. 4/F). The inner end opening 31 of the tube 28 may have a normal 102 (i.e. flat), oblique 101 or step-form 100 shape (FIGS. 4/A and 9/A, B and C). There may be a thread 23 (FIG. 2/D), stick 51 (FIG. 4/A) or rod 61 (FIG. 11) connected to the outer surface of the inner end 52 of the tube, each of them allowing to fix the tube 28 to the abdominal wall 41. The stick 51 may have a connecting foot 58 that fits into the advantageously longitudinally situated connecting groove 11 on the outer surface of the tube 28, and said connecting foot 58 is slidable within the groove 11 (FIG. 10). In this case the inner end 52 of the tube 28, which is fixed to the abdominal wall 41 with the stick 51, is slidable back and forth by the help of the connecting foot 58, thereby allowing the proper adjustment of the inner end 52 over the designated operating field. At the same time by the help of the rigid stick 51 or rod 61 the inner end 52 of the tube 28 is easily maneuverable to any desired part of the intraabdominal cavity, or is fixable in any desired location and position, respectively (FIG. 11). Of course several other outer endoscopic devices 30 (e.g. wound closure device, camera 44, forceps, etc.) could be connected to the groove 11 located on the outer surface of the tube 28 (e.g. FIG. 27).

In the following part hereof, the tubes 28 and the endoscopic devices 66, 103 housing surgical instruments 6 and/or trocar sleeves 7 will be discussed with their possible advantageous embodiments.

The tube 28 refers to a solution, which has a long cylindrical body advantageously with one single lumen inside, and into this lumen surgical instruments 6, trocar sleeves 7 or other accessory devices could be inserted (FIGS. 4/A and 9/A).

Figure 9:
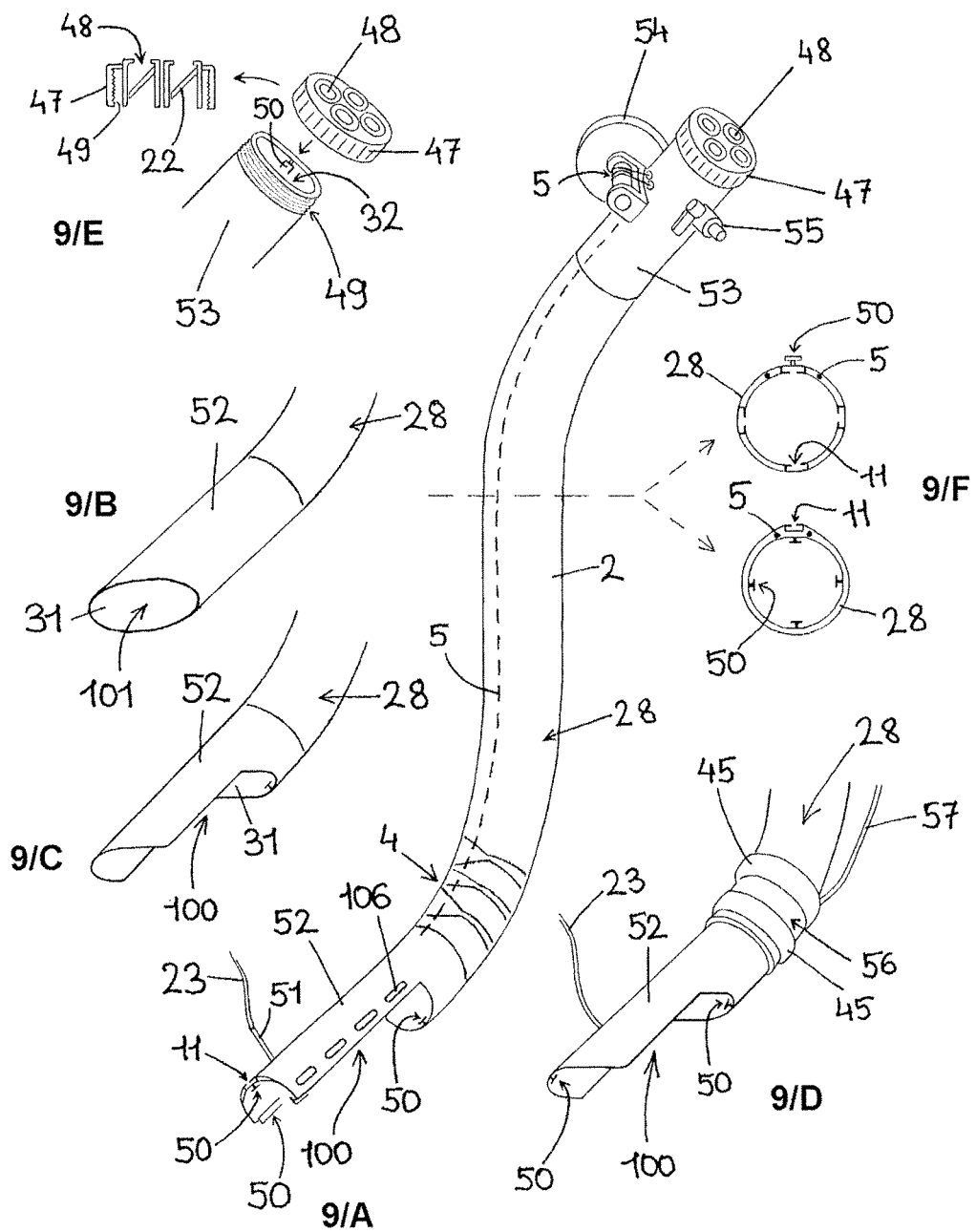

According to the simplest advantageous solution both ends 52, 53 of the tube 28 are normal (i.e. straight) 102, and its cross section is round or elliptical (FIG. 4/A). Advantageously the outer 53 and the inner ends 52 of the tube 28 could be rigid and the middle part 2 could be flexible or could be rigid (similar to FIG. 23) if required. The inner diameter of the tube 28 makes it possible to insert more than one—advantageously four—trocar sleeves 7. The inner surface of the tube 28 could be completely smooth, or according to an advantageous embodiment, may have longitudinal connecting grooves 11 or rails 50 on the inner surface (FIG. 9/F). Advantageously there could be longitudinal connecting grooves 11 or rails 50 also on the outer surface of the tube 28. A thread 23 (FIG. 2/D), a stick 51 (FIG. 4/A) or a rod 61 (FIG. 11) could be attached to the outer surface of the tube 28 advantageously at the inner end 52 region. There is advantageously a joint-like articulation 4 between the inner end 52 and the middle part 2 of the tube 28 (FIG. 9/A). The inner end 52 is bendable at the articulation 4 relative to the middle part 2 by the help of a pair of wires 5 that extend longitudinally throughout the tube 28, and an articulating device 54 mounted on the outer 53 end of the tube 28. The opening 31 of the inner end 52 of the tube 28 could be normal 102 (i.e. straight) FIG. 4/A, oblique 101 (FIG. 9/B) or step-form 100 (FIGS. 9/A and C). The inner opening 31 is straight 102 if the plane of the inner opening 31 is perpendicular to the longitudinal axis of the tube 28. The inner opening 31 is oblique 101 if the plane of the inner opening 31 is not perpendicular to the longitudinal axis of the tube 28. The inner opening 31 is step-form 100, if the straight 102 or oblique 101 opening is combined together with an opening located on the side of the inner end 52 of the tube 28 (the plane of the side opening is advantageously parallel with the longitudinal axis). The step-form opening 100 has a greater advantage because it significantly expands the size of the interventional area and assures the easier maneuvers.

The greater the size of the opening 31 of the inner end 52 facing toward the operation field, the greater is the freedom of movements/maneuvers of the instruments 6. This opening 31 area could be readily enlarged to the desired size by additionally increasing the size of the side opening component. An independent opening could be situated also on the wall of the middle part 2 of the tube 28. Advantageously there are an articulating device 54, a gas connection 55, and an arbitrary detachable or attachable airproof cap 47, closing the outer opening 32, mounted on the outer end 53 of the tube 28 (FIGS. 9/A and E). The cap 47 is attached to the outer end 53 by means of screw-threads or by any other known airproof connections. There are cap openings 48 with valves 22 on the cap 47.

Figure 23:
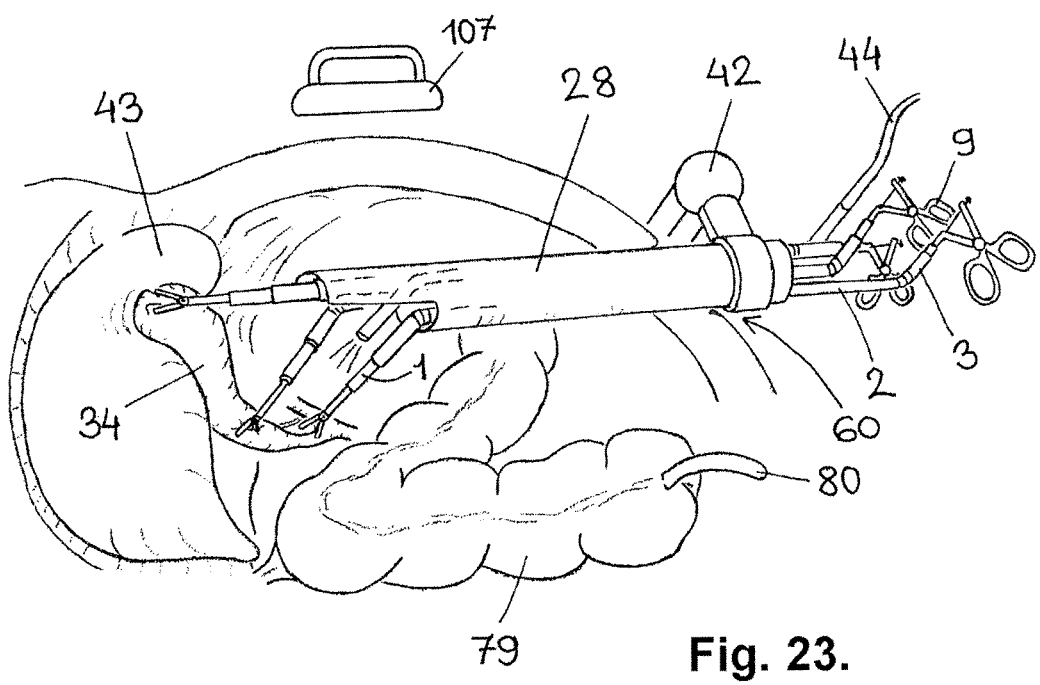
FIG. 23 shows a SPLS (Single Port Laparoscopic Surgery) gall bladder operation performed with a laparo-endoscopic system according to the invention having a rigid tube with step-form opened inner end, FIG. 24/A shows the laparo-endoscopic system according to the invention with an oblique and step-form opened inner end and with a protective sheath according to the invention that is introduced into the patient through a natural orifice, FIG. 24/B shows the removal of the gall bladder by the help of the laparo-endoscopic system according to the invention through the protective sheath according to the invention.

In case of the SPLS procedures advantageously the whole tube 28 is rigid (FIG. 23).

In case of either solution referred above an optional external fixateur device 42 could be attached (e.g. FIG. 21, 23 or 25) to the outer end of any instrument 6, trocar sleeve 7, tube 28 (e.g. FIGS. 4/A and 9/A) or endoscopic device 66, 103 (e.g. FIG. 15 or 17/A), and said external fixateur device 42 is able to fix the outer end transiently or permanently in a desired position.

In case of either solution above the inner end of any instrument 6, trocar sleeve 7, tube 28 or endoscopic device 66, 103 could be fixed via a thread 23 (FIG. 2/D), or a stick 51 (FIG. 4/A) or a control rod 61 (FIG. 11), being attached to the inner end, to the abdominal wall and/or to an external fixateur device 42.

The endoscopic device 66, 103 refers to a solution, which has a long cylindrical body advantageously with round or elliptical cross section and with more than one working channels 27 inside (FIGS. 12, 13, 14, 15 and 17). The elliptical cross section is advantageous, because the distance between the two lateral working channels 27 could be larger (FIG. 12/E) which allows easier maneuvers to the instruments 6 within these two working channels 27. Advantageously there could be connecting grooves 11 or rails 50 formed on the outer surface of either type of endoscopic device 66, 103 in order to establish additional external connections (e.g. with a thread 23, stick 51, control rod 61, stomach closure device, etc.). According to an advantageous embodiment there could be an articulation 4 formed at the inner end of either type of endoscopic device 66, 103, and said articulation 4 is bent by a pair of wires 5 and an articulating device 54. This pair of wires 5 extends through the entire endoscopic device 66, 103 and is connected to the articulating device 54 located at the outer end of the endoscopic device 66, 103. The inner and the outer ends of either type of endoscopic device 66, 103 are advantageously rigid and the middle part could be flexible or rigid. Either endoscopic device 66, 103 may have optionally a gas channel 64 and a suction-irrigation channel 65.

Figure 12:
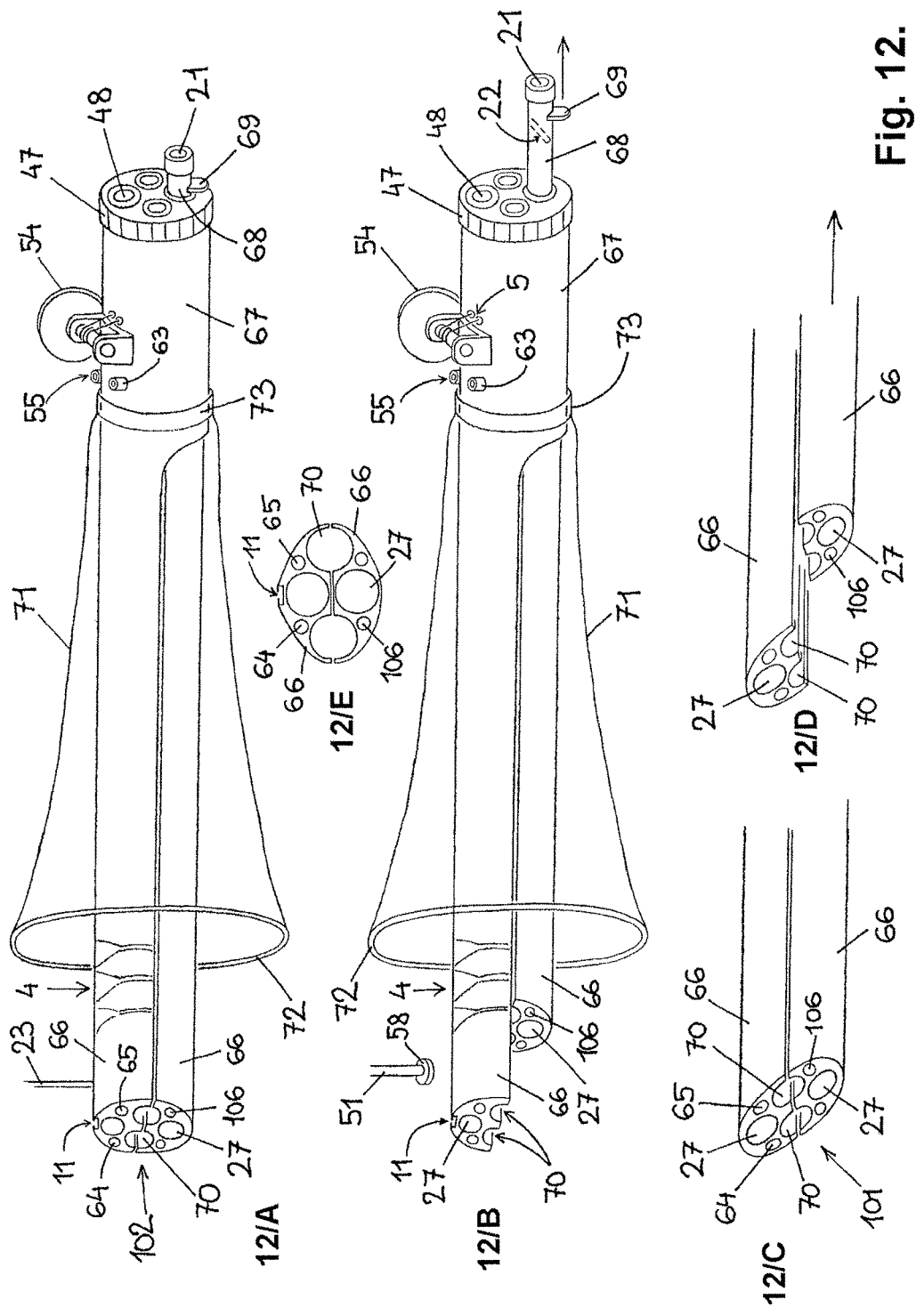

According to a possible advantageous solution the endoscopic device 66 is divided (FIGS. 12 and 15). In this case the endoscopic device 66 is partially or totally divided into two parts (upper and lower parts) by a plane that is advantageously parallel with the longitudinal axis. The two parts are connected together by sliding connection 29, and they are optionally movable back and forth along their longitudinal axis relative to each other. The dividing plane may divide the working channel 27 inside the endoscopic device 66 into two complementary divided working channels 70 (FIG. 12). When the two divided parts of the endoscopic device 66 are shifted longitudinally relative to each other, the divided working channels 70 become free at their inner ends. The instruments 6 bent at their inner articulations 4 are easily movable back and forth within the free part of the divided working channels 70 with or without the trocar sleeves 7. The free part of the divided working channel 70 is advantageous because it allows the telescopic inner end 1 and head 8 of the instrument 6—i.e. the part that is distal to the inner articulation 4—to exit from the free part of the divided working channel 70 along its full length in order to reach the interventional area. The length of the free parts of the divided working channels 70 could be changed optionally (increase or decrease) by shifting the two divided endoscopic parts longitudinally relative to one another (FIG. 12). According to and advantageous arrangement of the four working channels 27, the plane dividing the endoscopic device 66 into two longitudinal parts also divides longitudinally two opposite working channels 70. The other two working channels 27—advantageously the upper and the lower channels—remain intact. The normal 102 (FIG. 12/A) or oblique 101 (FIG. 12/C) inner ends of the divided endoscopic device 66 could be transformed into a step-form 100 (FIGS. 12/B and D) inner end by the longitudinal shift of the two parts (advantageously only the upper part or only the inner part) relative to one another, in order to achieve the advantages discussed above.

According to a possible advantageous embodiment the outer end of the divided endoscopic device 66 is rigid. The rigid end of the upper part of the device 66 is completed to a full cylinder, in such a way, that the rigid end of the slidable lower part is also inside the cylinder (FIG. 12/A). The outer end completed to a full cylinder is airtight and has advantageously four air proof openings 48 with valves 22, and said openings 48 are the inlet openings of the intact 27 or divided 70 working channels situated within the endoscopic device 66. The airtight closure of the cylindrical common end 67 may be also achieved by an optionally securable cap 47 with airtight inlet openings 48 and valves 22 (e.g. similar to FIG. 9/E).

Figure 13:
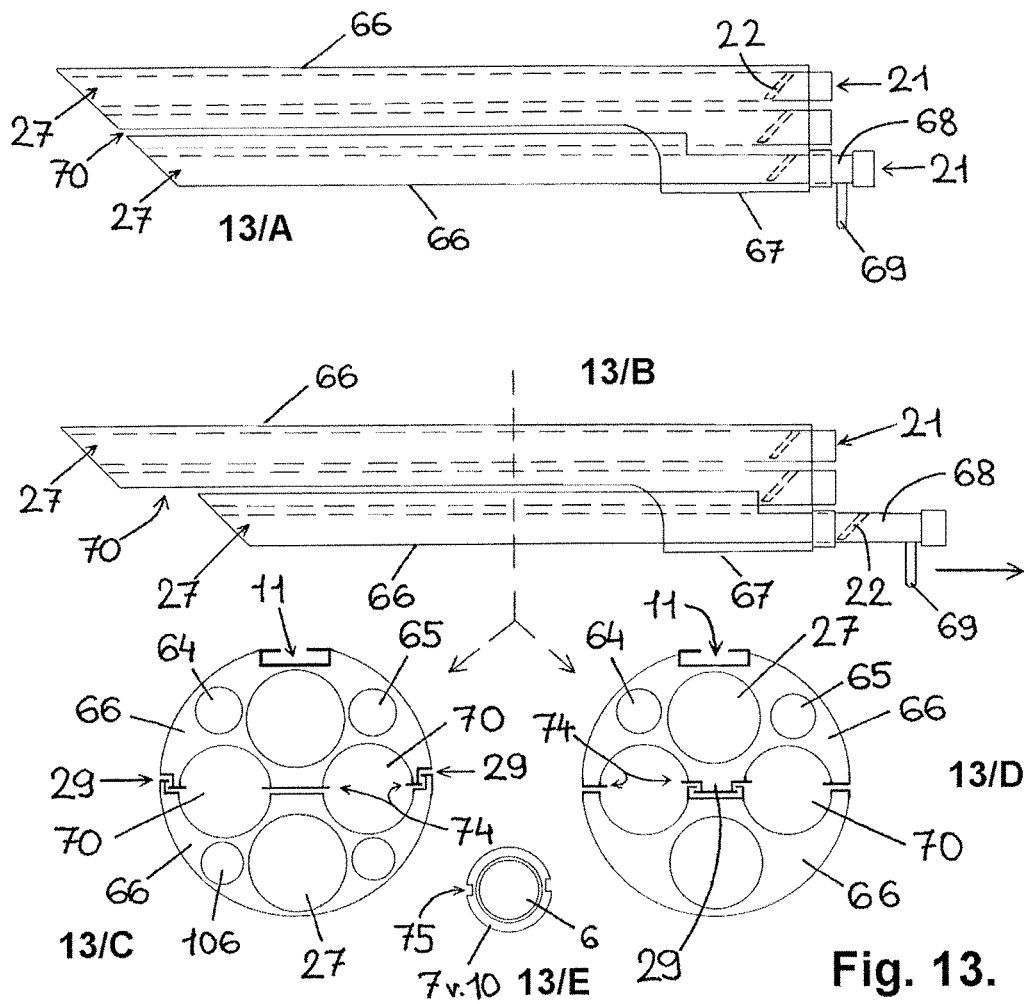

Advantageously the trocar shaft 68—i.e. the rigid tube-like continuation of the lower part—exits the common cylindrical end 67 through the lower outer opening 48 (FIGS. 13/A and B). The trocar shaft 68—provided with a valve 22—is the external continuation of the intact working channel 27 located inside the lower endoscopic part, and said trocar shaft 68, which extends through the lower outer opening 48, has an ear-like handle 69 at the outer end that helps to move the lower endoscopic part longitudinally back and forth. Advantageously the trocar shaft 68 is shifted in and out through the lower outer opening 48 of the common cylindrical end 67 by the help of the ear-like handle 69, which consequently means the longitudinal back and forth movement of the inner end of the lower endoscopic part. Thereby the size of the step-form inner opening 100—and consequently the size of the interventional area—is optionally adjustable.

Figure 14:
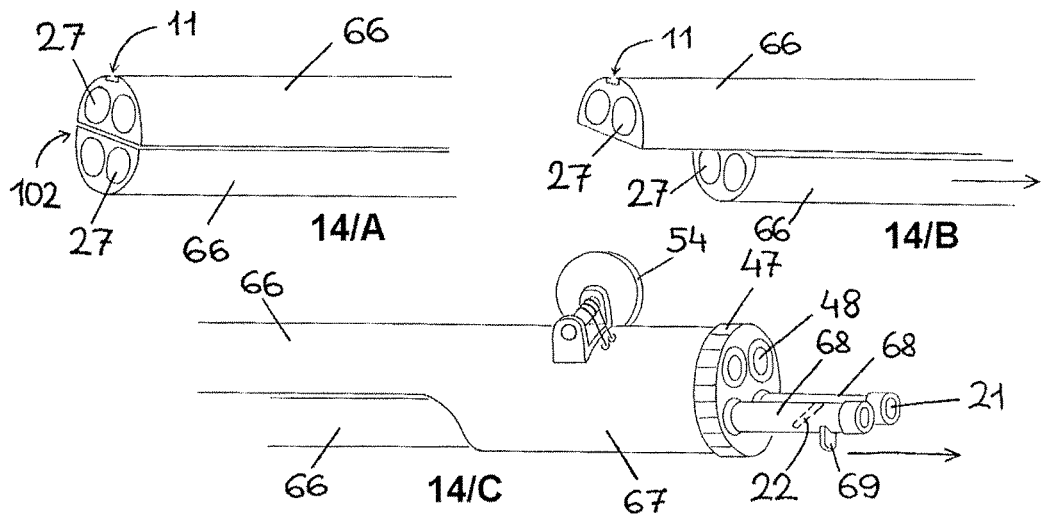

According to another possible solution, the plane dividing the endoscopic device 66 parallel with the longitudinal axis does not divide any of the working channels 27. Advantageously both the upper and the lower endoscopic parts contain two intact working channels 27 (FIG. 14). In this case the shape of the outer end of the endoscopic device could be a common cylinder 67 similarly to the previous solution, except that now two rigid trocar shafts 68, which are the external continuation of the two working channels 27 of the lower endoscopic part, exit trough the two lower outer openings 48 of the common cylindrical end 67.

According to another possible solution, the outer ends of the divided endoscopic device 66 are similarly divided as the inner ends, and both outer ends are hermetically sealed (FIG. 15). The upper and lower outer ends have airtight outer openings with valves 22. In this case either endoscopic part—the upper and the lower endoscopic parts are connected together by sliding connection 29—could be removed from the patient and could be replaced by a larger endoscopic tool (e.g. an endoscopic stapler 88 similarly to FIG. 26/A), or through the space of the removed endoscopic part tissue or organ specimens could be removed as well.

Figure 17:
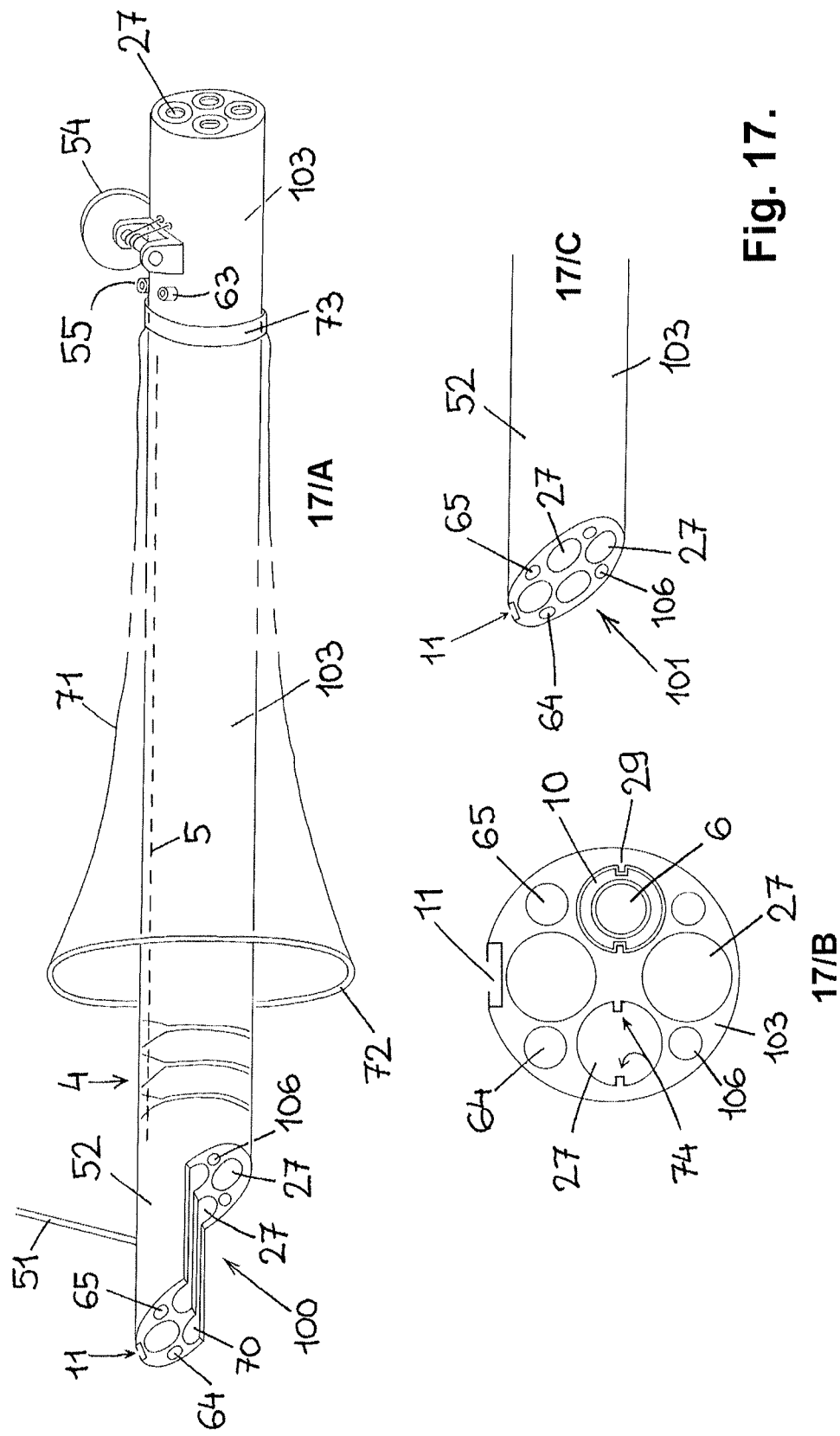

According to another advantageous embodiment the endoscopic device 103 is solid and undivided (FIG. 17). The opening of the inner end of the device could be normal 102, or oblique 101 or step-form 100. In case the inner end has a step-form opening 100 there could be one or more working channels divided 70 partially advantageously only at the inner end region, in order to achieve the above detailed advantages. Advantageously the upper and the lower working channels 27 are intact (i.e. undivided) while the other working channels 70 on both sides are divided at their inner ends. Of course a pair of intact (i.e. undivided) upper and a pair of intact lower working channels 27 arrangement is also possible. The outer end of the undivided endoscopic device 103 is hermetically sealed and there are airtight outer openings with valves 22, and said outer openings are the inlets of the working channels 27, 70.

Inside the divided working channels 70 of any type of endoscopic device 66, 103 there are sliding connections 29 (e.g. sliding rim 74, connecting groove 11 or rail 50) allowing the proper attachment and fixation, and the longitudinal back and forth movement of the inserted trocar sleeve 7 or instrument 6 (e.g. FIGS. 13/C, D and 17/B). This connecting components (e.g. sliding rim 74, connecting groove 11 or rail 50) are connected to the connecting components (e.g. groove 75 on FIG. 13/E) of the instruments 6 or the trocar sleeves 7.

Figure 21:
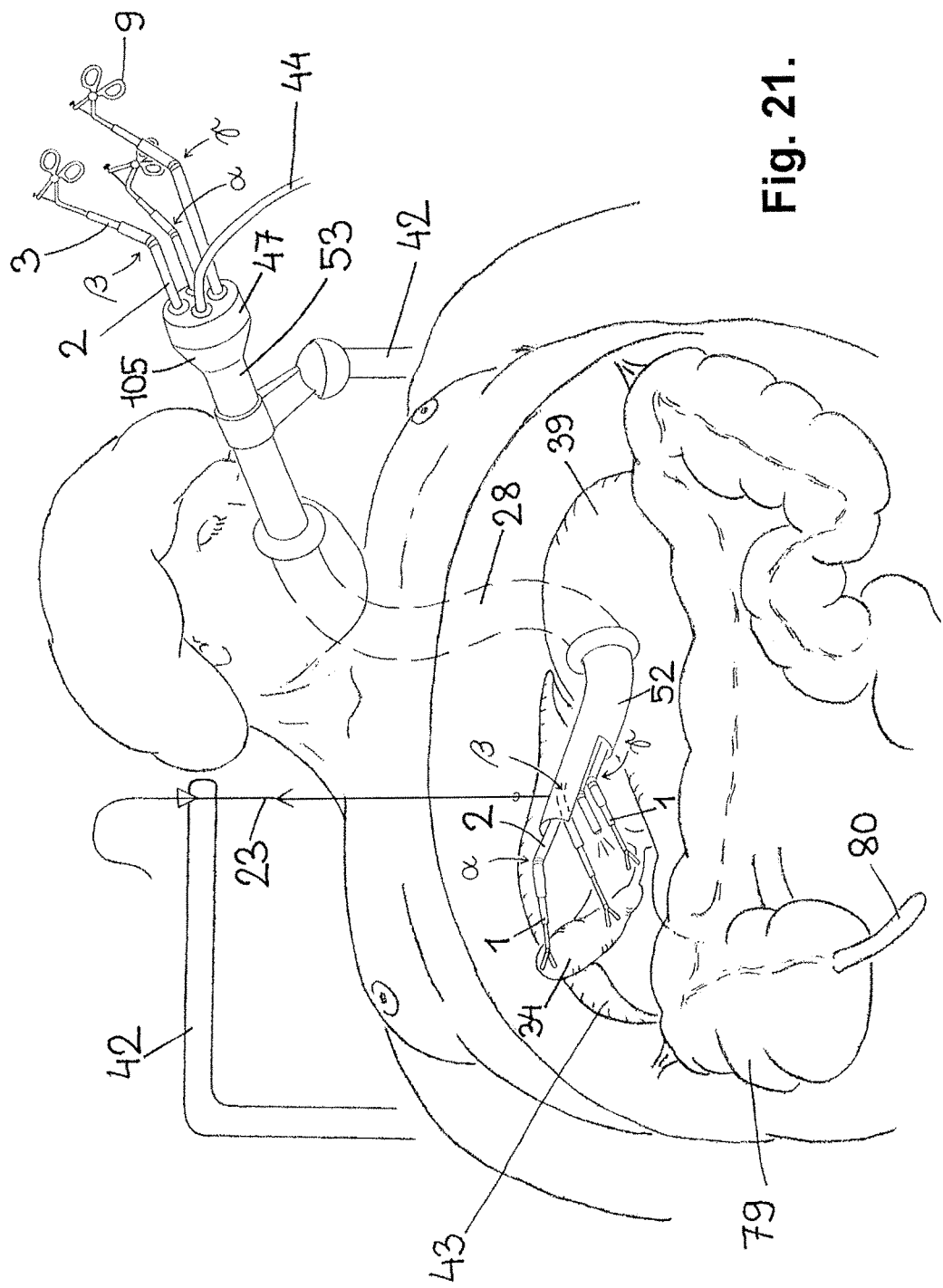
FIG. 21 shows a gall bladder operation by a laparo-endoscopic system having a step-form opened inner end, illustrating the fixation possibilities of the inner and the outer ends of the system, and the anatomical landmarks.
Figure 25:
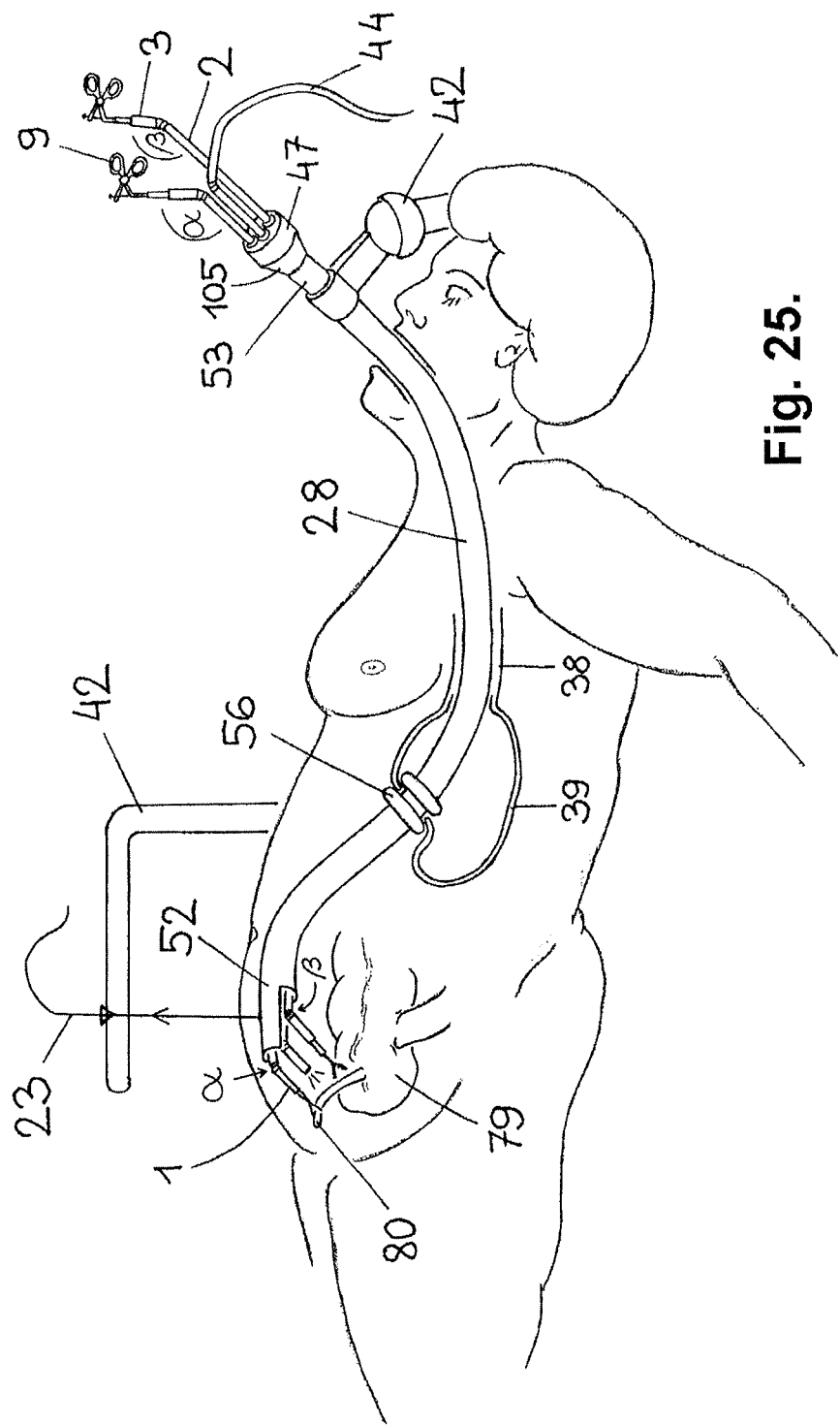
FIG. 25 shows an appendectomy operation by a laparo-endoscopic system according to the invention having a step-form opened inner end, the fixation possibilities of the inner and the outer ends of the system, and the anatomical landmarks, FIGS. 26/A and B show an appendectomy operation performed with a laparo-endoscopic system according to the invention having an oblique and step-form opened inner end and with an endoscopic stapler according to the invention, and the removal of the appendix throughout the protective sheath according to the invention.

The outer end of any type of tube 28 or endoscopic device 66, 103 may have a cone shape 105 (FIGS. 21 and 25). This is advantageous because it allows the easier handling of the outer ends 3 of the instruments 6

Any type of the previously mentioned instruments 6, trocar sleeves 7, tubes 28 or endoscopic devices 66, 103 may have light sources 106, e.g. LEDs advantageously on their inner ends (FIG. 9/A). More light sources 106 result in better illumination of the operating field.

Figure 34:
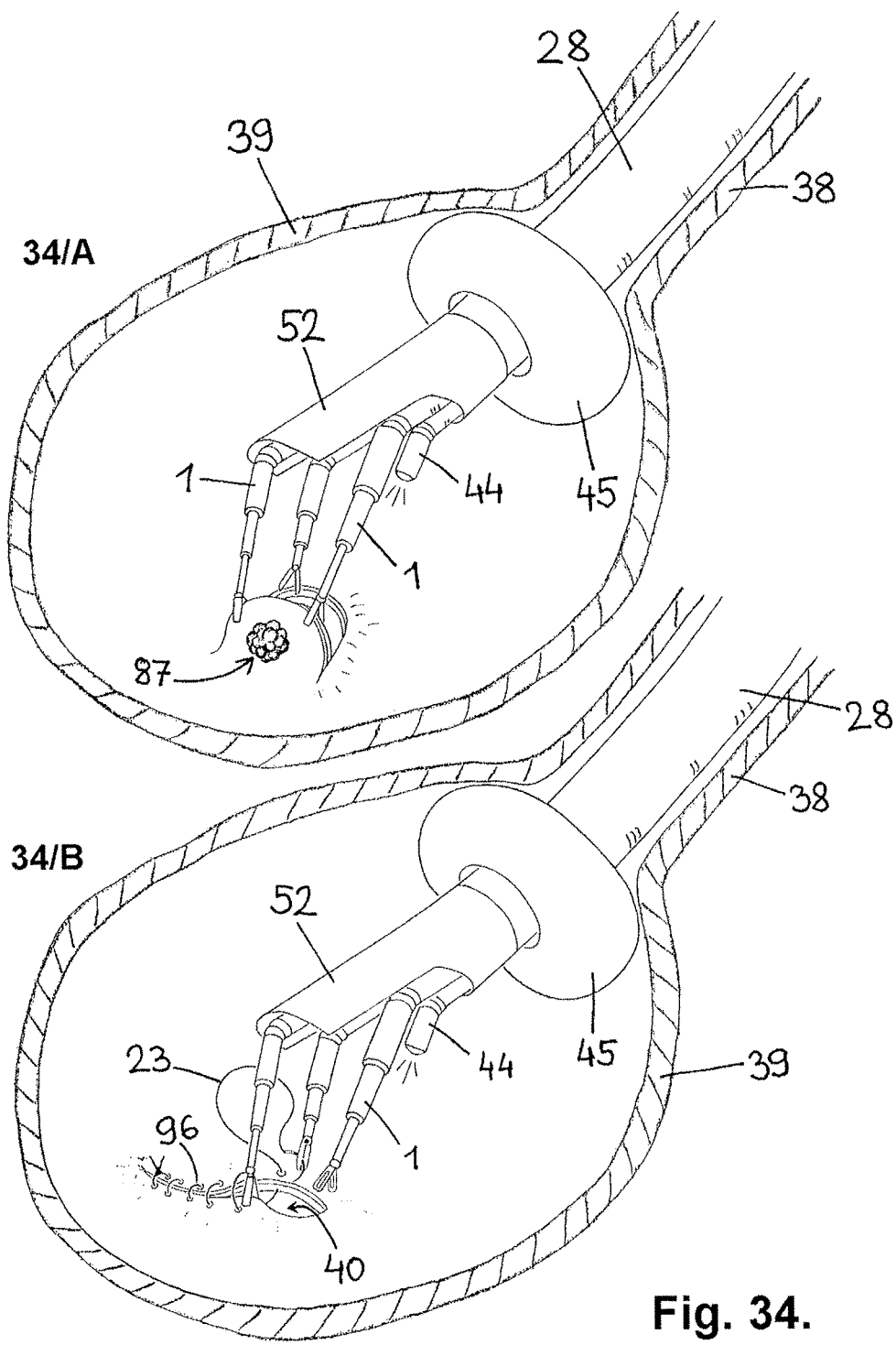

Any kind of combination of the previously mentioned laparo-endoscopic system could be able to perform surgical interventions inside the hollow organs lumen (e.g. excision of pathological lesions, wound closure, feeding tube insertion). In this case an inflatable balloon 45 helps to secure the device (e.g. instrument 6, trocar sleeve 7, tube 28 or endoscopic device 66, 103), which is placed at the inner end region of the device (FIG. 34). Advantageously the balloon is slidable on the device, and its outer diameter is larger than the diameter of the esophagus 38 or other hollow organ 39, respectively.

In any of the previously described instrument 6—trocar sleeve 7—tube 28 or endoscopic device 66, 103 system, or instrument 6—trocar sleeve 7 system, or instrument 6—tube 28 or endoscopic device 66, 103 system the inserted instruments 6 are able to reliably reproduce all three-dimensional laparoscopic maneuvers by the help of bandings, rotations and telescopic movements.

Any type of the previously described instruments 6, trocar sleeves 7, tubes 28 or endoscopic devices 66, 103 may have a disposable or a reusable design.

Any type of the previously described instruments 6, trocar sleeves 7, tubes 28 or endoscopic devices 66, 103 may have a design allowing their disassembling, cleansing and reassembling.

The following description relates to suitable accessory devices.

The first such accessory device could be a protective sheath 71 attachable to the outside of connected trocar sleeves 7, tube 28 or endoscopic device 66, 103 (FIGS. 12/A and B). The protective sheath 71 is advantageously cone shaped and is made of a strong clingfilm-like material, that on the outer end has a connecting ring 73 or tube 97—able to connect airtight to the outer end 53 of a tube 28 or an endoscopic device 66, 103—, and on the inner end it has a self-expandable ring 72. The protective sheath 71 covers the tube 28 or the endoscopic device 66, 103. The protective sheath 71 is inserted via a natural orifice into the abdominal cavity through the wound 40 on the wall of a hollow organ 39 advantageously in a rolled position over the tube 28 or the endoscopic device 66, 103. When the protective sheath 71 enters the abdominal cavity, the expanding cone shaped inner end with the self-expandable ring 72 and the contracting wound 40 around the protective sheath 71 prevent to escape the gas from the insufflated abdominal cavity (e.g. FIG. 24/A). In addition the protective sheath 71 protects the wall of the hollow organs 39 and the adjacent area against the injuries caused by the moving instruments 6, and prevents the contact with the contaminated secretions, or with the diseased tissues or organs. The cone shaped inner end (i.e. the inner end has a larger circumference) allows to remove the tissues or organs easier. Of course any other shape of the protective sheath 71 could be among the possible solutions.

Figure 19:
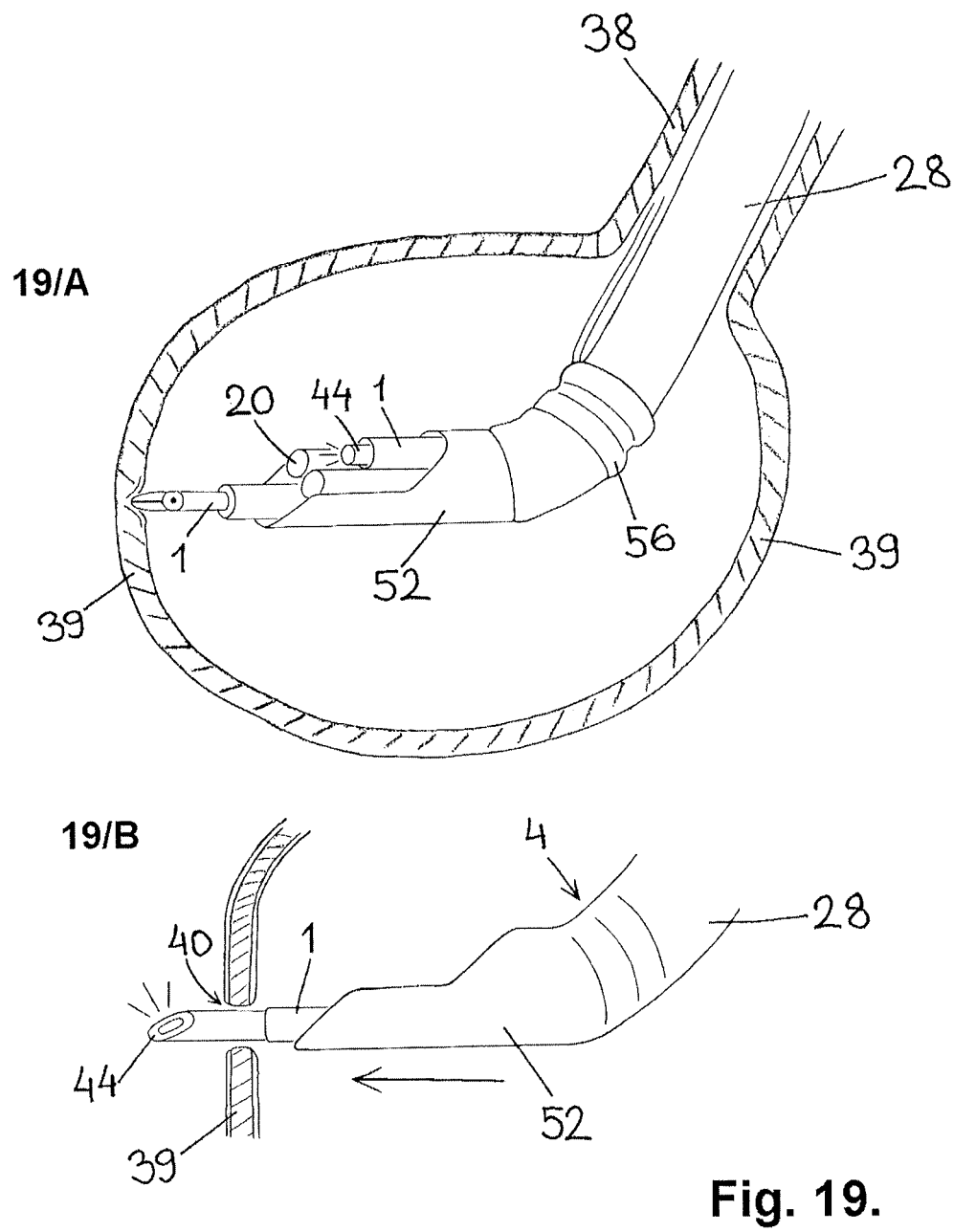
FIG. 19/A shows the instruments according to the present invention within a step-form opened tube just penetrating through the stomach, FIG. 19/B shows a camera introduced through the small wound, FIGS. 20/A, 20/B 20/C and 20/D show another advantageous method with an access catheter to penetrate through the wall of a hollow organ.

The second such accessory device could be an endoscopic balloon tube 56 with independently inflatable balloons 45, which could be placed advantageously on the inner end region of the connected trocar sleeves 7, tube 28 or endoscopic device 66, 103 (FIGS. 9 and 19/A). This device 56 is placed into the wound 40 on the wall of a hollow organ 39 (similar to FIG. 22), in order to prevent gas leakage. When the endoscopic balloon tube 56 is already inserted, the air ducts 57 of the balloons 45 extend over the natural orifice.

The third such accessory device could be an access catheter 104, that enables to create a wound opening 40 on the wall of a hollow organ 39 (e.g. the stomach) during the access phase (FIGS. 20/A, B and C). The catheter 104 could be inserted into any suitable working channels 27, 70. There is an electric unit 76—that is able to cut or coagulate tissues—mounted on the inner end advantageously on the tip of the catheter 104, said electric unit 76 has an electrical wiring extending along the catheter 104, and said electrical wiring is connectable to an electric power supply. The electric unit 76 is slightly recessed within the tip of the catheter 104 in order to avoid the direct contact with extended tissue areas. There are two consecutive balloons 77, 78 on the catheter 104. The one 77 closer to the inner end has advantageously an umbrella-like shape characteristically with a diameter—that is perpendicular to the longitudinal axis—larger than that of the tube 28 or the endoscopic device 66, 103. The next one is the dilating balloon 78 that has advantageously a cylinder-like shape and its diameter is smaller than that of the tube 28 or the endoscopic device 66, 103. The balloons 77, 78 are independently inflatable or deflatable, and their air ducts extend over the outer end of the tube 28 or the endoscopic device 66, 103.

Figure 18:
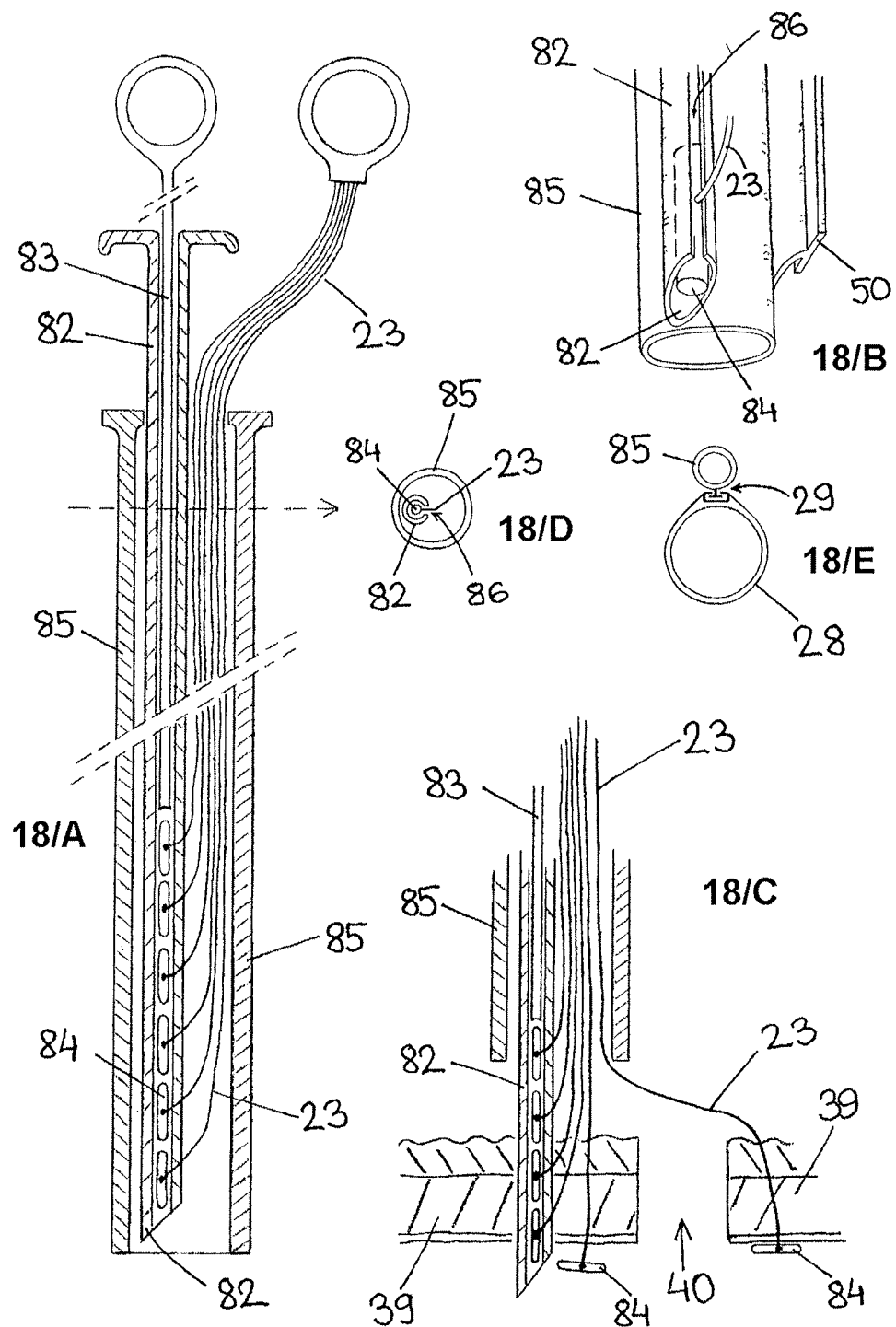

The fourth such accessory device could be a wound closure device allowing the closure of a wound 40 created on the wall of a hollow organ 39 (FIG. 18). According to an advantageous embodiment the wound closure device consists of an implanting tube 85, an implanting sheath 82, locking elements 84, threads 23 and an implanting rod 83. The groove 11 or rail 50 on the outer surface of the implanting tube 85 could be connected with sliding connection 29 to the rail 50 or groove 11 on the outer surface of the trocar sleeve 7, tube 28 or endoscopic device 66, 103. There are locking elements 84 on the inner end of each thread 23 and there is one fixing knob on their outer ends. The locking elements 84 are inside the implanting sheath 82, and the sheath 82 with the threads 23 are inside the implanting tube 85. The inner end of the implanting sheath 82 is sharp and there is a longitudinal split 86 on the side of the sheath 82, and there is an implanting rod 83 located above the locking elements 84. The locking elements 84, the implanting rod 83, the implanting sheath 82, the threads 23 and the implanting tube 85 are moveable to each other or to a trocar sleeve 7, tube 28 or endoscopic device 66, 103, respectively. The implanting rod 83, the implanting sheath 82 and the implanting tube 85 are advantageously flexible.

The fifth such accessory device could be assembled advantageously by rigid components, and allows the optional fixation of the outer and the inner ends of a trocar sleeve 7, tube 28 or endoscopic device 66, 103 (e.g. FIGS. 21, 23 and 25). One end of this fixateur device 42 is fixed independently from the patient, e.g. to the operating table. One type of the external fixateur device 42 could be suitable to fix the thread 23, or stick 51 or rod 61 connected to the outer surface of the inner ends, while another type of the device 42 is suitable to fix the outer ends. The shape, the angle and the position of the fixateur device 42 could be secured or changed optionally. The fixation of the inner end makes possible to simultaneously lift the abdominal wall 41. In addition, the fixation of the inner end to the abdominal wall 41 could be executed by the help of a magnetic device 107 (FIG. 23).

Figure 30:
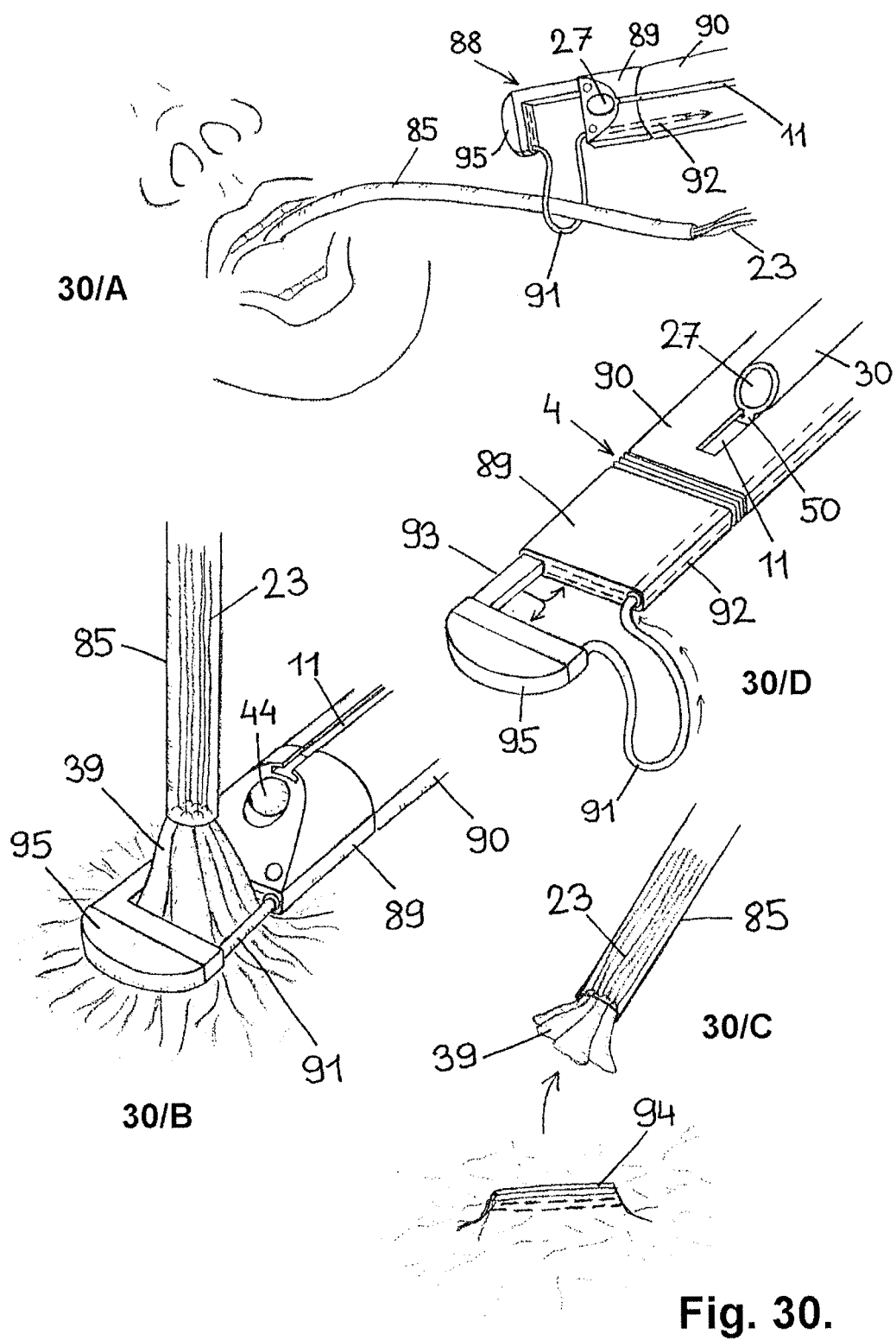
Figure 32:
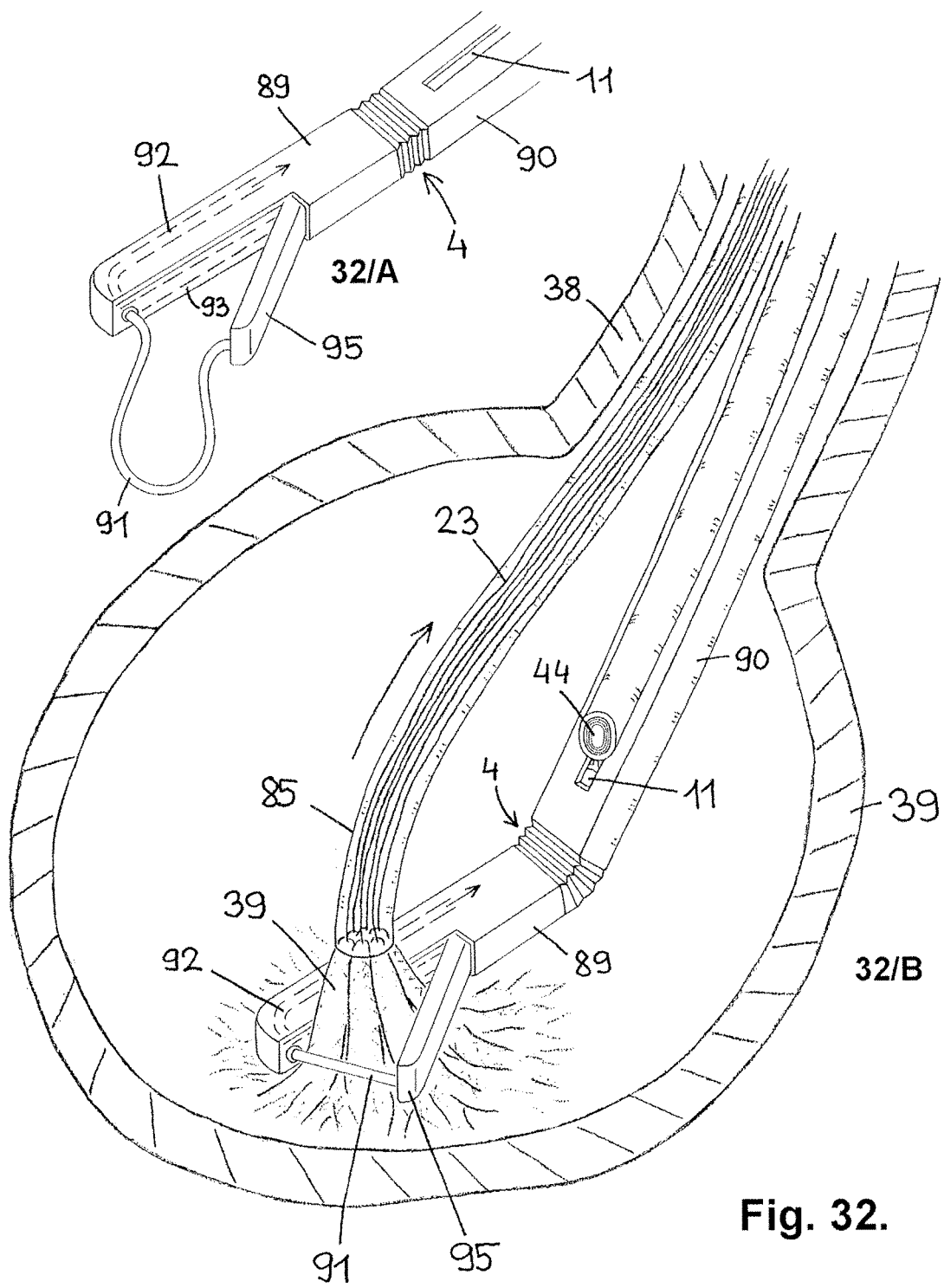

The sixth such accessory device could be a modified endoscopic stapler 88 (FIG. 30-32). Advantageously the head 89 of the stapler 88 is rigid and the body 90 is partially or totally flexible. The head 89 and the body 90 are connected together advantageously by an articulation 4. The stapling surface 93 of the head 89 is advantageously perpendicular or parallel to the longitudinal axis of the device 88, but any other inclination angle is possible. There is a control thread 91 located between the free ends of the stapling surfaces 93, and said control thread 91 could be optionally tensioned or relaxed. The thread 91 is situated within the channel 92 that extends throughout the head 89 and the body 90 of the device 88. The end of the thread 91 extends over the outer end of the stapler 88. When the control thread 91 is tensioned the desired part of the tissue is directed among the stapling surfaces 93. Under full tension the thread 91 supports the parallel closure of the adjustable jaw 95 of the stapler head 89. Advantageously there may be a working channel 27 inside, or a groove 11 or rail 50 on the outer surface of the body 90 of the stapler 88 and said groove 11 or rail 50 allows the connection of an accessory device 30 (e.g. a trocar sleeve 7, a camera 44, a forceps, etc.). The stapling surfaces 93 may have straight, curved, wavy or any other recently known shape. The diameter of the stapler 88 is preferably smaller than the inner diameter of the tube 28 (e.g. FIG. 26/A).

The functions of the laparo-endoscopic system which according to the present invention is developed to accomplish all steps of the new surgical interventions (access, surgical intervention, and closure) of NOTES (Natural Orifice Transluminal Endoscopic Surgery), SPLS (Single Port Laparoscopic Surgery) and IE (Interventional Endoscopy) are as follows:

1. Access

Before starting the operation the laparo-endoscopic device is assembled.

Figure 24:
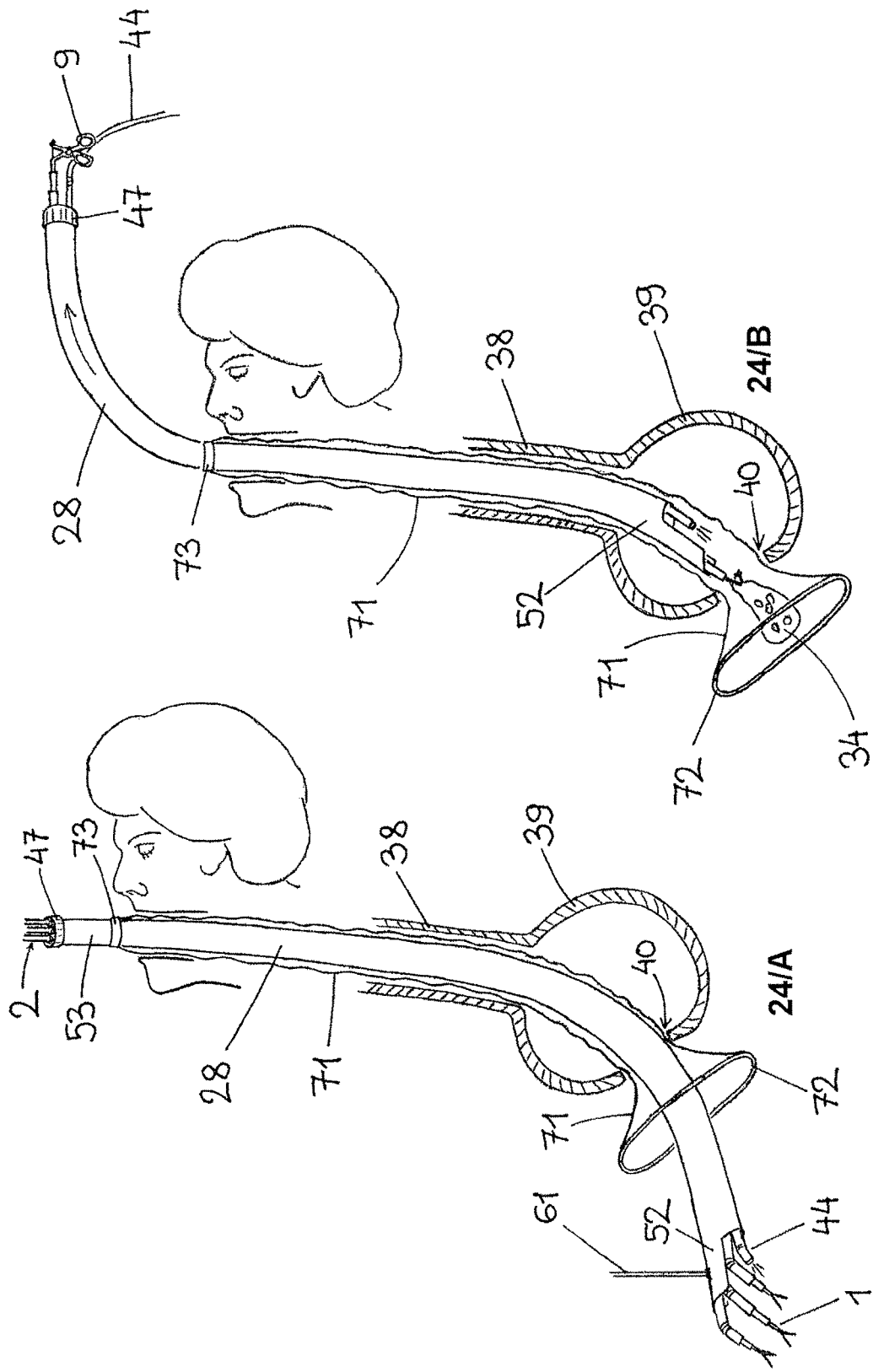

According to an advantageous solution, the protective sheath 71 is placed over the tube 28 and first it is attached to the outer surface of the tube 28 (e.g. FIG. 9/A), then it is rolled over the body of the tube 28, finally a part of the expandable ring 72 is pulled into the inner opening 31 of the tube 28 by the help of an inserted instrument 6. The trocar sleeves 7 are introduced into the tube 28 by the help of sliding connections 29. A camera 44 is placed into the working channel 27 of the lower trocar sleeve 7 (FIGS. 19 and 20), and the access catheter 104 into the upper trocar sleeve 7. Thereafter the appropriately assembled flexible device system is introduced through the patient's natural orifice, actually through the mouth and the esophagus 38 into the stomach 39. It is advantageous to create the opening 40 on the anterior wall of the stomach 39. For this reason it is advantageous to use a tube 28 with a step-form opened 100 rigid inner end 52, and said inner end 52 could be bent at the articulation 4 perpendicularly toward the wall of the stomach 39 by the help of an articulating device 54 and wires 5. The tip of the inner end 52 is pushed against the stomach wall 39, and then the access catheter 104 is pushed forward within the upper trocar sleeve 7 (FIG. 20). By activating the electric unit 76 within the tip of the access catheter 104, the forward moving catheter 104 passes through the stomach wall 39 at the desired point due to the developing thermal effect. Then the catheter 104 is pushed forward until the umbrella-like protective balloon 77 enters the abdominal cavity. At this point the protective balloon 77 is inflated, and it is pulled against the outer surface of the stomach wall 39 by pulling the whole catheter 104 outward. In this position the dilating balloon 78 is just in the stomach wall 39. Now the dilating balloon 78 is insufflated to reach a diameter that is less than the diameter of the tube 28, then the balloon 78 is desufflated, thereafter the step-form opened 100 inner end 52 of the tube 28 with gradually increasing diameter is pushed through the dilated wound 40 into the abdominal cavity until the expandable ring 72 of the rolled protective sheath 71 enters the abdominal cavity. Then the expandable ring 72 is expelled out of the inner end 52 of the tube 28 into the abdominal cavity with an instrument 6, and so the inner opening of the advantageously cone-shaped protective sheath 71 expands, and the protective sheath 71 is compressed to the tube 28 by the wound (FIG. 24/A). These two effects prevent gas leakage through the wound opening 40. The expandable ring 72 prevents the inadvertent removal of the protective sheath 71. The airtight connecting ring 73 or tube 97 situated on the outer end of the protective sheath 71 prevents gas leakage at the outer end of the device system. The outer ends of the trocar sleeves 7, tubes 28 or endoscopic devices 66, 103 are sealed hermetically.

After the inner end of the device system is inserted into the abdominal cavity the protective balloon 77 is also desufflated, and the access catheter 104 is removed out of the trocar sleeve 7. The insufflated protective balloon 77 that is pulled toward the inner end 52 of the tube 28 during the access procedure protects the adjacent organs and tissues against inadvertent injuries.

According to another version of the access procedure, the head 8 of an instrument 6 is first passed through the stomach wall 39. Through the small created opening 40 a camera 44 is inserted to check the abdominal cavity (FIG. 19). Once the wound 40 area is controlled, the oblique 101 and step-form 100 opened inner end 52 is passed gently through the stomach wall 39 following the camera 44, thus the wound 40 is dilated gradually.

The access procedure is the same if an endoscopic device 66, 103 is used (e.g. FIGS. 12, 15 and 17).

When connected trocar sleeves 7 are introduced into the stomach 39, the system is directed toward the anterior stomach wall 39. Only one telescopic inner end 1 is passed through the stomach wall 39 by the help of an access catheter 104 or a camera 44, and then the procedure follows the previously described steps.

An endoscopic balloon tube 56 could be attached to the system instead of a protective sheath 71 as well (FIG. 19/A). As soon as the inner end enters the abdominal cavity, the outer balloon 45 is insufflated through the air duct 57 and then the system is pushed inward until the outer balloon 45 hits inside the stomach wall. At this point the inner balloon 45 is also insufflated through an additional air duct 57. The two balloons 45 fix the stomach wall 39 at the wound opening 40. The endoscopic balloon tube 56 is slidable.

Figure 22:
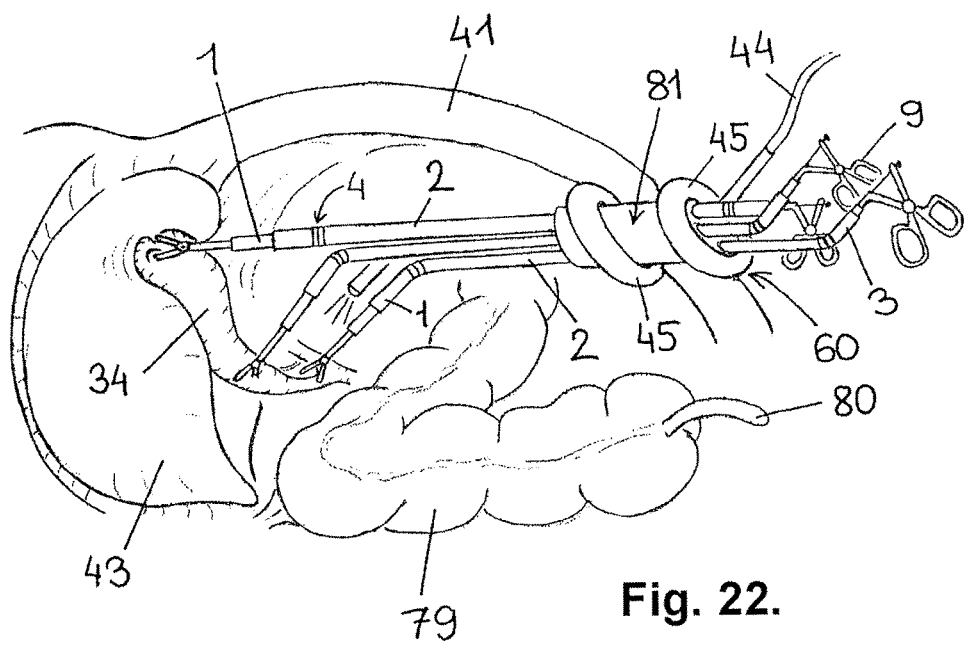
FIG. 22 shows a SPLS (Single Port Laparoscopic Surgery) gall bladder operation through an abdominal port by the surgical instruments according to the invention with rigid ends and middle parts.

In case of an SPLS intervention the access procedure is performed via the navel, advantageously similarly to the laparoscopic technique. A small umbilical incision is made and under direct eye-control a laparo-endoscopic system is inserted into the abdominal cavity. This system consists of advantageously rigid trocar sleeves 7, rigid tube 28 or endoscopic device 66, 103, and is also provided with a protective sheath 71 or an abdominal port 81 (FIGS. 22 and 23). It is enough to fix the outer end of the rigid system to an external fixateur 42.

2. Operation

This is the most important part of the whole intervention: to remove or to cure the diseased organs or tissues. The procedure performed with the laparo-endoscopic system is similar to the well developed laparoscopic technique. The inner end 52 of the device system is fixed above the operation field through the abdominal wall 41 to an external fixateur 42 (FIGS. 21 and 25) by the help of a thread 23 (FIG. 2/D), a stick 51 (FIGS. 4/A and B) or a control rod 61 (FIG. 11). The abdominal wall 41 could be lifted with the fixed inner end 52, thereby preventing the collapse of the abdominal cavity over the operation field in case of a gas leakage, and that makes the intervention much safer. The outer end 53 of the system is fixed to another external fixateur 42. It is advantageous, if the appropriately flexible middle part 2 of the system is bent only slightly. The positions of the instruments 6, which are inserted through the working channels 27, are adjusted by the help of the articulations 4, the telescopic ends 1, 3, the sliding connections 29 or the control rod 61. The inner 1 and the outer 3 ends of the instrument 6 inside the tube 28 are moving similarly as the inner and outer components of a traditional laparoscopic instrument (with the only difference that they are separated by the middle 2 part), thus the intervention could be performed similar to the laparoscopic technique, where one single instrument 6 is controlled by only one hand (e.g. gall bladder operation 34 or appendectomy 80—FIGS. 21 and 25). If the size of the operation field is changed during the procedure, the position of the inner end 52 could be also adjusted, depending on the type of the fixation. In case of a thread 23 or a stick 51 the position could be changed by stitching through the abdominal wall 41 at another point. It is easier to use a control rod 61 (FIG. 11) because it is strong and rigid enough to simply move the inner end 52 of the device system from an earlier position to a newer one. The advantage of the control rod 61 could be increased, if it is inserted into the abdominal cavity through the umbilicus 60 (advantageously by the visual control of the camera 44 of the device system) and is attached to the inner end 52 of the tube 28. With this method it is possible to deliver the inner end 52 of the system to any area of the abdominal cavity and to fix it in the new position, thereby even the extending operations could be performed without creating any additional wounds. This technique makes it possible to perform any kind of interventions within the body cavities.

Figure 26:
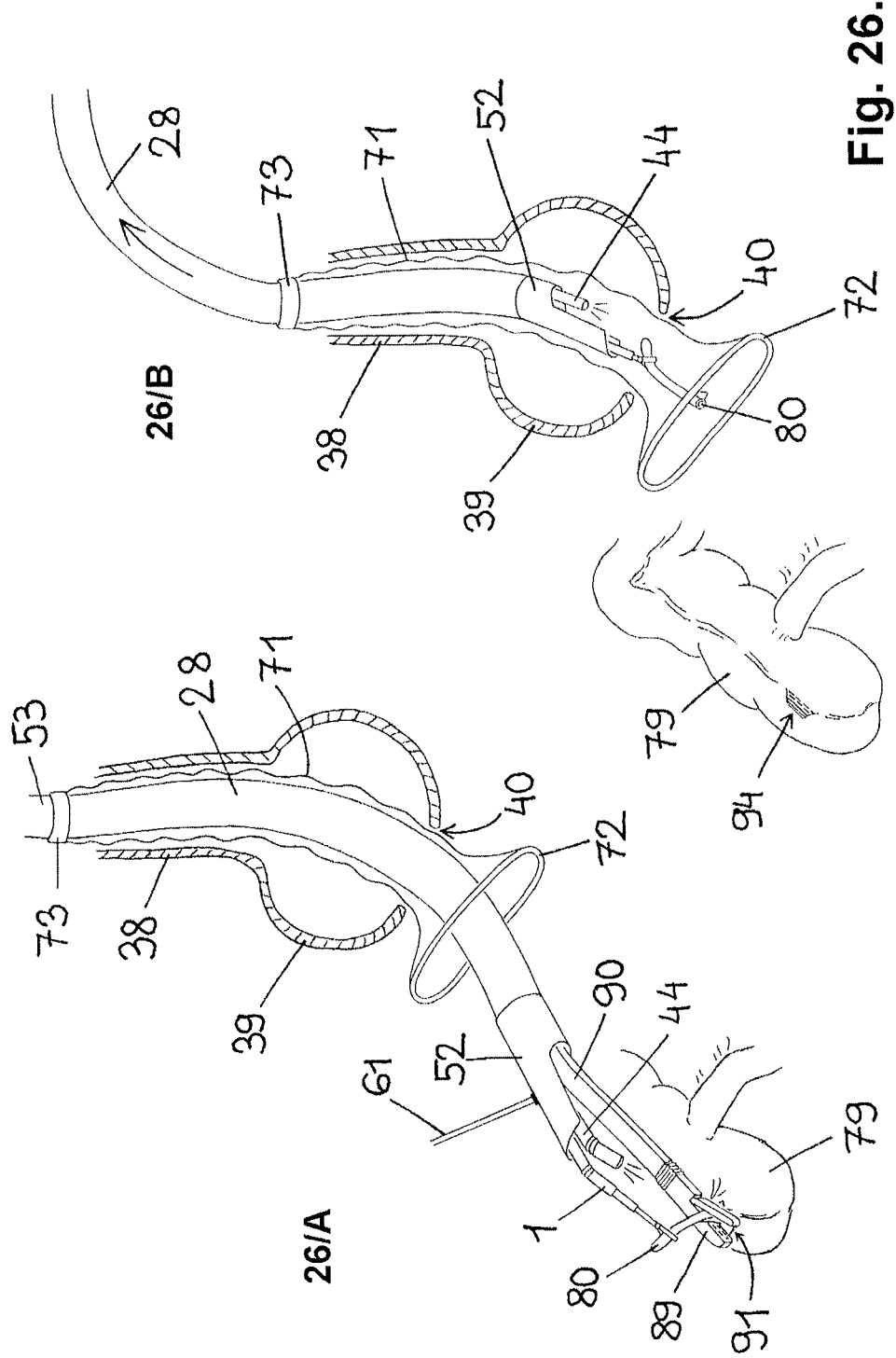

In case of appendectomy, the appendix 80 could be removed by the help of an endoscopic stapler 88 (FIG. 26/A). The endoscopic stapler 88 could be inserted through the empty space of the tube 28 created by the previous removal of two adjacent trocar sleeves 7. The stapler head 89 is opened and the appendix 80 is pulled between the stapling surfaces 93 and the still loose control thread 91 by the help of a forceps 6. Thereafter the control thread 91 is tensioned along with the closure of the adjustable jaw 95 and the stapler 88 is closed at the origin of the appendix 80. After firing the stapler 88 the appendix 80 is removed.

The gall bladder 34 or the appendix 80 are removed from the abdominal cavity advantageously through the tube 28, and if the tube has a cap 47 on the outer end 53, the cap 47 should be removed (e.g. FIG. 9/E). If the tissue or organ is larger than the inner diameter of the tube 28, they are removed through the protective sheath 71 by pulling them into the sheath 71 with an instrument 6 inside the tube 28 (FIGS. 24/B and 26/B). The protective sheath 71 makes it possible to easily insert the previously removed laparo-endoscopic system back into the abdominal cavity.

In case of a non-divided endoscopic device 103 (FIG. 17/A) the steps of the procedure is similar to the previously described methods, except that the endoscopic stapler 88 is inserted into the abdominal cavity outside the laparo-endoscopic system.

If one part of the divided endoscopic device 66 (e.g. FIG. 15) is removed, the endoscopic stapler 88 could be inserted through the emptied space. The size of the step-form opened 100 inner end of the divided device 66 could be adjusted to various operation fields by longitudinally shifting back and forth the divided parts relative to each other without creating additional wounds.

When performing SPLS interventions, the rigid instruments 6, trocar sleeves 7, tube 28 or endoscopic device 66, 103 are inserted through the umbilicus 60, and their inner ends are directed toward the operation field (FIGS. 22 and 23). The outer end of the device system could be fixed in the right position by an external fixateur 42. The further steps of the intervention are similar to the laparoscopic technique. In case of a rigid device system there is no need to fix the inner end, however on request it is executable with a thread 23, a stick 51 or a control rod 61, as discussed earlier.

In case of a procedure performed inside a hollow organ 39 (e.g. the excision of a pathological lesion 87 on the wall), the fixation of the inner end of the laparo-endoscopic device is achieved by a balloon 45 that is slidable along the device (FIGS. 34/A and B). If the balloon 45 is insufflated to an appropriate size, it becomes secured within the hollow organ, so the laparo-endoscopic system is able to lean on the balloon 45, and in addition the inner end is diverged from the stomach wall 39 to an appropriate distance. The advantageously multiple vacuum fixation would have similar effectiveness.

3. Closure

Figure 28:
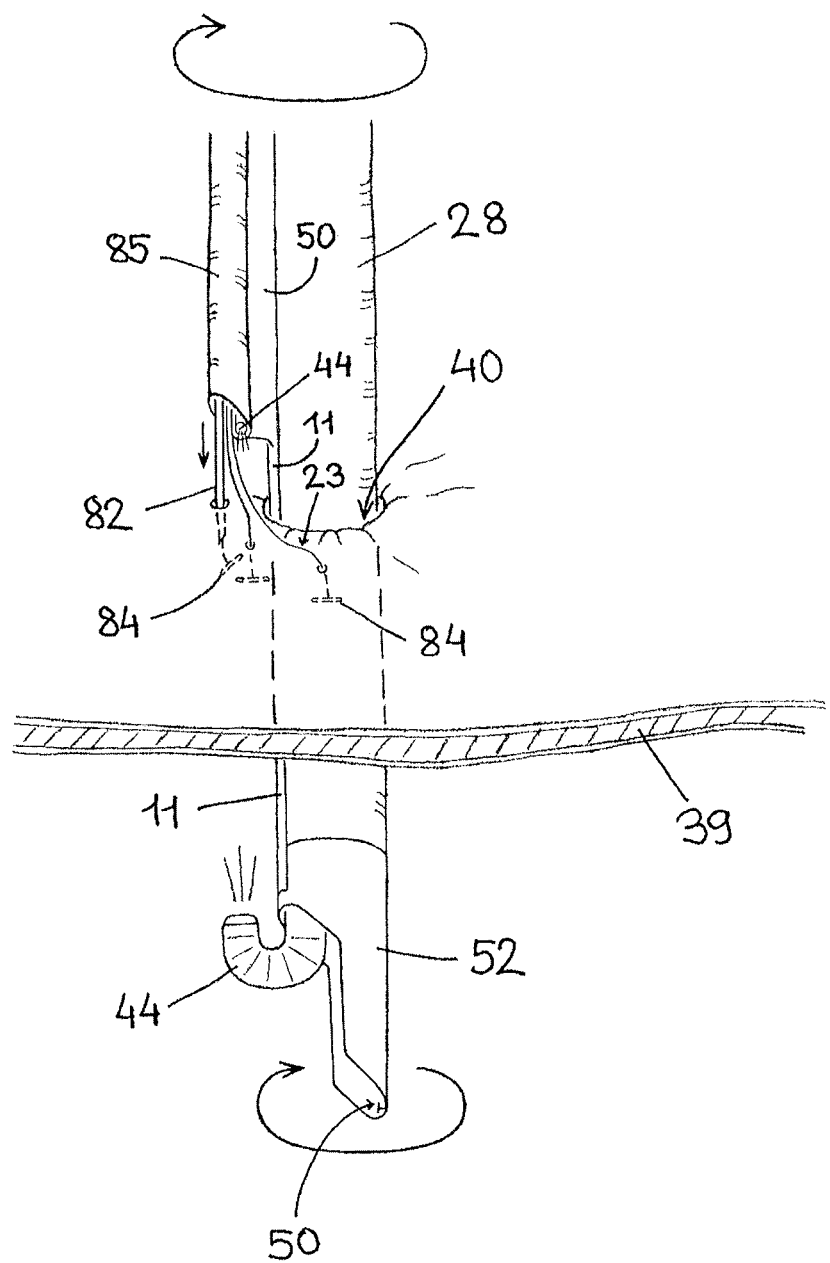
FIG. 28 shows the wound closure device according to the invention with a camera attached to the tube that is turned around within the wound of a hollow organ during the closure process, FIG. 29/A shows threads with locking elements that are inserted circumferentially into the wound edges of the hollow organ, and the implanting tube according to the invention, FIG. 29/B shows the threads with locking elements that are inserted around a pathological lesion of a hollow organ, and the implanting tube according to the invention, FIG. 29/C shows the contracted wound edges pulled up into the tube by the threads, and the elevated wound edges, FIG. 30/A shows a laterally opening straight endoscopic stapler according to the invention advantageously with a control thread and a camera that is inserted through the mouth along the implanting tube, FIG. 30/B shows the contracted and elevated wound edges or the elevated pathologic lesion of the bowel wall that are pulled among the stapling surfaces by the threads and the implanting tube, and also the control thread under tension, FIG. 30/C shows the closed wound of the hollow organ by the stapler according to the invention, and also the implanting tube and the removed tissue, FIG. 30/D shows another possible embodiment of the endoscopic stapler according to the invention with a control thread and a connecting groove, FIGS. 31/A, B and C show a wound closure process with a laterally opening curved endoscopic stapler according to the invention, FIG. 32/A shows a front opening straight endoscopic stapler according to the invention bent at the articulation and having a control thread and a connecting groove, FIG. 32/B shows the contracted and elevated wound edges or the elevated pathologic lesion of the bowel wall that are pulled by the threads and the implanting tube among the stapling surfaces of a front opening endoscopic stapler according to the invention, that is bent at its articulation, and also has a control thread and a camera attached by sliding connection, FIGS. 33/A and B show the excision of the tissue pulled into the stapler according to the invention and also the stapled closure of the wall of the hollow organ, and finally FIGS. 34/A and B show the full excision of the pathological lesion located on the wall of a hollow organ and also the closure of the wound with sutures by the help of a laparo-endoscopic system according to the invention.
Figure 29:
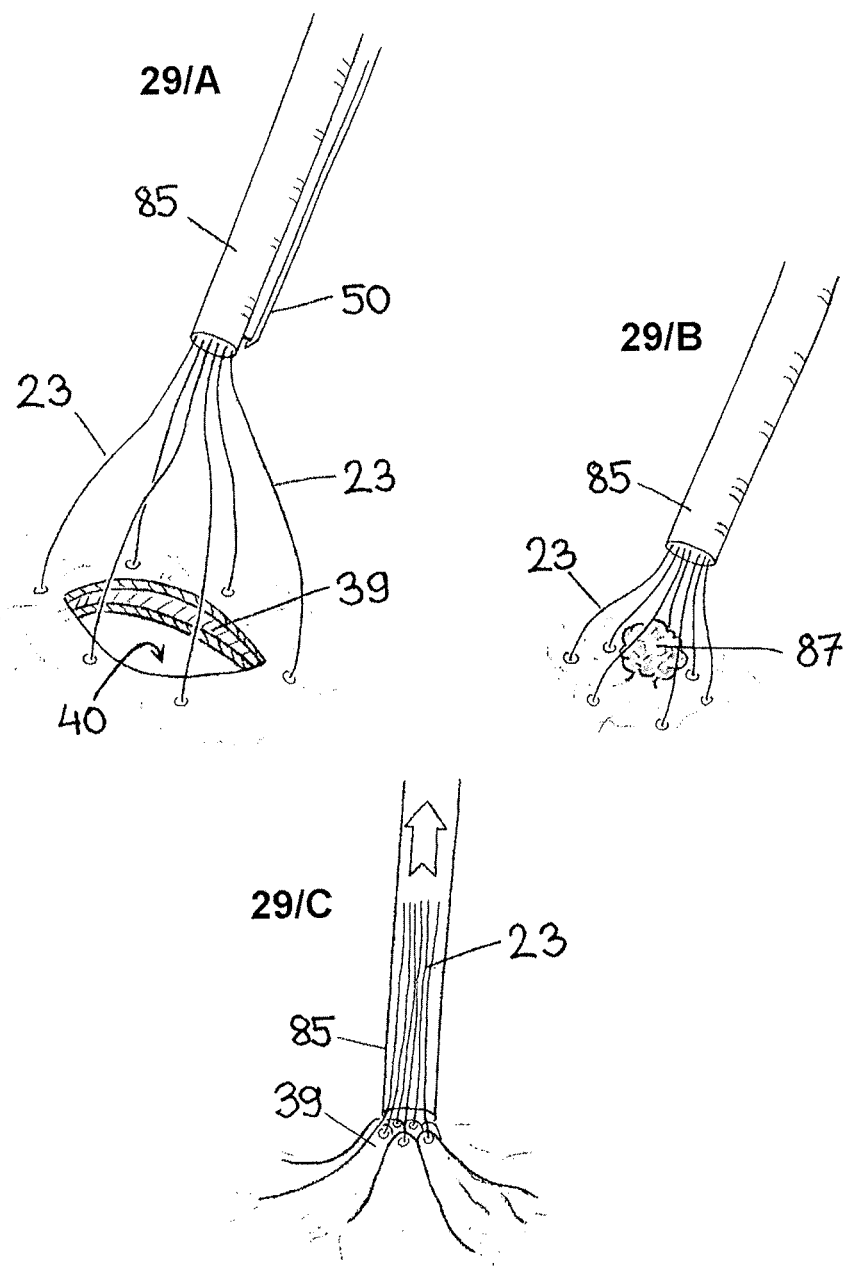

The closure means primarily the reliable closure of a wound opening 40 on the wall of a hollow organ 39. As soon as the surgical intervention is completed, and the diseased organ or tissues are removed, and the operation field is checked again, the protective sheath 71 or the endoscopic balloon tube 56 are removed through the mouth, while the inner ends of the connected trocar sleeves 7, or the inner end of the tube 28 or the endoscopic device 66, 103 remain within the abdominal cavity. Within the inner end opening there is advantageously a single camera 44 in a curved position, which makes the visual control in the adjacent region of the wound 40 possible. A wound closure system is attached with sliding connection 29 (advantageously through a connecting groove 11 or rail 50) to the outer surface of the connected trocar sleeves 7, or the tube 28 or the endoscopic device 66, 103. The implanting tube 85 with the implanting sheath 82, locking elements 84, threads 23 and camera 44 inside is pushed against the stomach wall 39. The appropriate distance between the laparo-endoscopic system and the connected implanting tube 85 allows to the locking elements 84 and the threads 23 to reliably hold the lifted wound edges 40. Controlled by the camera 44 of the implanting tube 85 the pointed shaped inner end of the implanting sheath 82 is pushed through the wall of the hollow organ 39, and by pushing the implanting rod 83 a locking element 84 with thread 23 is discharged (FIG. 18/C). The movement of the implanting sheath 82 through the stomach wall 39 and the correct position of the locking elements 84 are controlled by a curved (retroflexed) camera 44 inside the abdominal cavity. This implanting maneuver should be repeated—by following the full rotation of the laparo-endoscopic system within the wound 40—to implant the locking elements 84 into the wound edges 40 around its whole circumference (FIG. 28). Then the laparo-endoscopic system is pulled back and removed from the patient, while the implanting tube 85 is dislodged from the laparo-endoscopic system by the help of the sliding connection 29 and remains in place. As a consequence, the locking elements 84 within the wound edges 40, the threads 23 and the tube 85 containing the threads 23 remain inside the stomach 39. By simultaneously lifting the threads upward and by pushing the implanting tube 85 downward, the edges of the wound 40 are pulled up into the inner end of the implanting tube (FIG. 29/C). The outer end of the implanting tube 85 is introduced between the stapling surfaces 93 and the control thread 91 of the stapler 88, and then the stapler 88 is pushed down along the implanting tube 85 to the wound 40 through the mouth (FIG. 30). Advantageously the stapler 88 has a camera 44.

Figure 33:
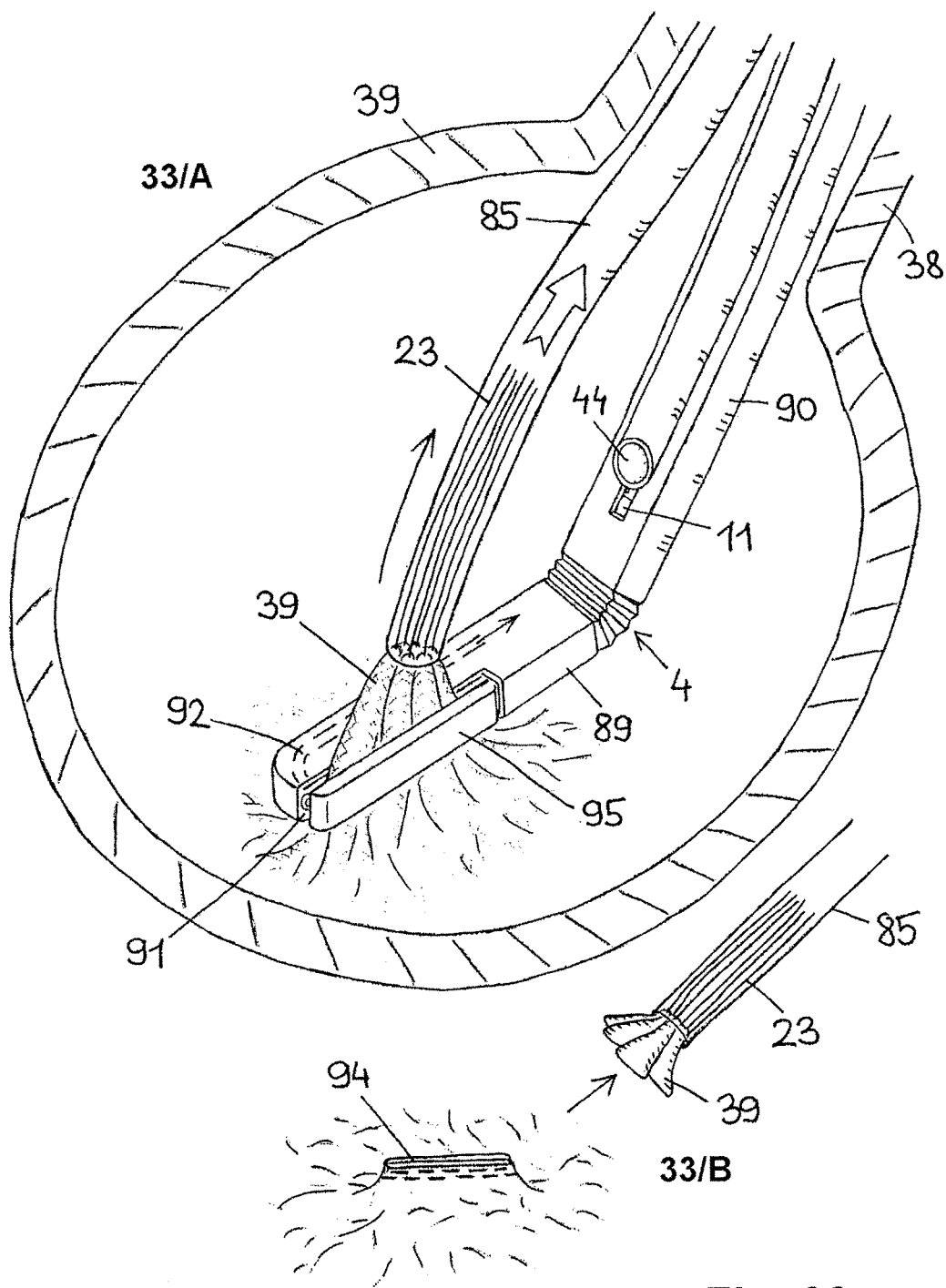

In order to achieve better control over the process the endoscopic stapler 88 is bent at the articulation 4. After the control thread 91 is slightly tensioned the stomach 39 wound 40 is pulled between the opened stapling surfaces 93 and the control thread 91. After the adjustable jaw 95 is closed while the control thread 91 is continuously tensioned, the situation is checked again with the camera 44. Then the stapler 88 is fired and the wound 40 is closed and the stapled wound 94 is checked with the camera 44. This procedure could be performed with different type of staplers (FIGS. 31, 32 and 33).

The closure process after SPLS intervention means the traditional closure of the abdominal 41 or umbilical 61 incisions.

The closure of the wound 40 inside the hollow organ could be performed with the wound closure system (discussed above) and the stapler 88, or with the laparo-endoscopic system secured with a balloon 45 (FIG. 34/B). In the later case the wound 40 is closed from inside with sutures 96 similarly to the laparoscopic suture technique.

The most important advantages of the solutions according to this invention shall be that they ensure to reliably accomplish all steps (access, surgical intervention, closure) of NOTES (Natural Orifice Transluminal Endoscopic Surgery), SPLS (Single Port Laparoscopic Surgery) and IE (Interventional Endoscopy) procedures through the natural orifices, similarly to the reliable and well developed laparoscopic techniques and maneuvers.

The invention claimed is:

1. Surgical device for surgical intervention, comprising a surgical instrument having an elongate instrument body having (i) a rigid instrument inner end guidable/steerable to an operation field in a human or animal body, (ii) a rigid instrument outer end operable by a user, (iii) a flexible instrument middle part resisting compression along a longitudinal axis and adapted to resist torsion around a longitudinal axis which connects said instrument outer end to said instrument inner end; the surgical device further comprising a sleeve having an elongate tubular body having a telescopic sleeve inner end, a telescopic sleeve outer end and a tubular sleeve middle part, the tubular sleeve middle part having an outer diameter adapted to be inserted into a human or animal body to access the operation field, the sleeve further having a first articulation provided between the sleeve outer end and the sleeve middle part and a second articulation provided between the sleeve inner end and the sleeve middle part; the surgical instrument being arranged in the trocar sleeve such that the instrument middle part is located in the sleeve middle part and extends through the first articulation and the second articulation into the sleeve outer end and the sleeve inner end respectively; the sleeve inner end surrounds at least partly the instrument inner end, and the sleeve outer end surrounds at least partly the instrument outer end;

the sleeve comprising a force transmission unit for maintaining same articulation angle at the first articulation and at the second articulation by rotating the sleeve inner end with respect to the sleeve middle part by the same rotational angle and in the same rotational direction as the sleeve outer end is rotated relative to the sleeve middle part; and the flexible instrument middle part being formed as a slidable flexible sheath and being dimensioned to transfer axial movement of the sleeve outer end to the sleeve inner end relative to the sleeve middle part by the same extent but in the opposite direction upon displacement within the sleeve tubular body by elongating the telescopic sleeve inner end when the telescopic sleeve outer end is compressed, and by contracting the telescopic sleeve inner end when the telescopic sleeve outer end is elongated.

2. The surgical device according to claim 1 characterized in that it comprises more than one sleeve each having a sleeve inner end, and the sleeve inner ends of at least two sleeves terminate in planes that are spaced from each other.

3. The surgical device according to claim 2 characterized in that at least one of said more than one sleeve defines at least one working channel therein being connected with sliding connection to at least one other sleeve.

4. The surgical device according to claim 1 characterized in that it has a tube comprising (i) a cylindrical body, (ii) an inner end and an outer end, and (iii) a gas connection and a suction-irrigation connection, and said tube is adapted to house at least two sleeves.

5. The surgical device according to claim 4 characterized in that on an outer surface of the inner end the tube has a connecting point formed as a member of the group consisting of a groove and a rail designed to connect to a control rod for fixation to an abdominal wall.

6. The surgical device according to claim 4 characterized in that on an outer surface of the tube's inner end the tube has a thread with a member of the group consisting of a needle and a stick which can be passed through the abdominal wall and can be fixed to an external fixateur.

7. The surgical device according to claim 1 wherein the first force transmission unit comprises at least one pair of antagonistic wires extending from the sleeve inner end throughout the first and second articulations and the sleeve middle part to the sleeve outer end opposite to one another.

8. The surgical device according to claim 7 wherein the surgical device comprises more than one sleeve, each sleeve receiving a surgical instrument, and wherein the surgical device is formed as an endoscopic device comprising a cylindrical body with an inner end and an outer end, and more than one working channel each adapted to receive one of said sleeves, the cylindrical body being at least partially separable into divided parts at a plane parallel with the longitudinal axis of the cylindrical body, said divided parts being connected by sliding connections shiftable relative to each other, and at the outer end of the cylindrical body one of the divided parts has a full cylinder shape into which another of the divided parts extends.

* * * * *